United States Patent
Howarth et al.

(10) Patent No.: US 11,873,323 B2
(45) Date of Patent: *Jan. 16, 2024

(54) PROTEINS AND PEPTIDE TAGS WITH ENHANCED RATE OF SPONTANEOUS ISOPEPTIDE BOND FORMATION AND USES THEREOF

(71) Applicant: Oxford University Innovation Limited, Oxford (GB)

(72) Inventors: Mark Howarth, Oxford (GB); Anthony Keeble, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 140 days.

This patent is subject to a terminal disclaimer.

(21) Appl. No.: 17/372,652

(22) Filed: Jul. 12, 2021

(65) Prior Publication Data

US 2022/0119459 A1   Apr. 21, 2022

Related U.S. Application Data

(63) Continuation of application No. 16/606,818, filed as application No. PCT/GB2018/051065 on Apr. 24, 2018, now Pat. No. 11,059,867.

(30) Foreign Application Priority Data

Apr. 24, 2017   (GB) ..................... 1706430

(51) Int. Cl.
 *C07K 14/315*   (2006.01)
(52) U.S. Cl.
 CPC ........ *C07K 14/315* (2013.01); *C07K 2319/02* (2013.01); *C07K 2319/21* (2013.01); *C07K 2319/24* (2013.01); *C07K 2319/50* (2013.01)
(58) Field of Classification Search
 CPC .............. C07K 14/315; C07K 2319/02; C07K 2319/21; C07K 2319/24; C07K 2319/50; C07K 2319/20
 See application file for complete search history.

(56) References Cited

U.S. PATENT DOCUMENTS

| | | | |
|---|---|---|---|
| 9,547,003 B2 | 1/2017 | Howarth | |
| 10,247,727 B2 | 4/2019 | Howarth | |
| 10,526,379 B2 | 1/2020 | Howarth | |
| 11,059,867 B2 * | 7/2021 | Howarth | .............. C07K 14/315 |
| 2013/0053544 A1 | 2/2013 | Howarth | |

FOREIGN PATENT DOCUMENTS

| | | |
|---|---|---|
| CN | 108026145 A | 5/2018 |
| WO | 2011/098772 A1 | 8/2011 |
| WO | 2016/112921 A1 | 7/2016 |
| WO | 2016/193746 A1 | 12/2016 |

(Continued)

OTHER PUBLICATIONS

Chinese Office Action for Application No. 201880027190.2, dated Feb. 22, 2023, pp. 1-13 (Translation Included).

(Continued)

*Primary Examiner* — Marcela M Cordero Garcia
(74) *Attorney, Agent, or Firm* — Thomas|Horstemeyer, LLP

(57) ABSTRACT

The present invention relates to a two-part linker comprising a peptide tag (peptide) and a polypeptide (protein) that is capable of spontaneously forming an isopeptide bond, particularly wherein: a) said peptide comprises an amino acid sequence as set forth in SEQ ID NO: 1, wherein: (i) X at position 1 is arginine or no amino acid; (ii) X at position 2 is glycine or no amino acid; (iii) X at position 5 is histidine or threonine; (iv) X at position 11 is alanine, glycine or valine; and (v) X at position 14 is arginine or lysine, wherein when X at position 1 is no amino acid, X at position 2 is no amino acid; and b) said polypeptide comprises: i) an amino acid sequence as set forth in SEQ ID NO: 2; ii) a portion of (i) comprising an amino acid sequence as set forth in SEQ ID NO: 101; iii) an amino acid sequence with at least 80% sequence identity to a sequence as set forth in SEQ ID NO: 2, wherein said amino acid sequence comprises a lysine at position 34, a glutamic acid at position 80 and one or more of the following: 1) threonine at position 5; 2) proline at position 16; 3) arginine at position 40; 4) histidine at position 65; 5) proline at position 92; 6) aspartic acid at position 100: 7) glutamic acid at position 108; and 8) threonine at position 116, wherein the specified amino acid residues are at positions equivalent to the positions in SEQ ID NO: 2; or iv) a portion of (iii) comprising an amino acid sequence with at least 80% sequence identity to a sequence as set forth in SEQ ID NO: 101, wherein the amino acid sequence comprises a lysine at position 10, a glutamic acid at position 56 and one or more of the following: 1) arginine at position 16; 2) histidine at position 41; 3) proline at position 68; and 4) aspartic acid at position 76, wherein the specified amino acid residues are at positions equivalent to the positions in SEQ ID NO: 101, and wherein said peptide and polypeptide are capable of spontaneously forming an isopeptide bond between the aspartic acid residue at position 10 of SEQ ID NO: 1 and the lysine residue at position 34 of SEQ ID NO: 2 or position 10 of SEQ ID NO: 101.

20 Claims, 16 Drawing Sheets
Specification includes a Sequence Listing.

(56) References Cited

FOREIGN PATENT DOCUMENTS

WO 2017/049094 A1 3/2017

OTHER PUBLICATIONS

International Research Report & Written Opinion for PCT/GB2018/051065, dated Jun. 29, 2018, pp. 1-10.
Anthony H. Keeble et al: "Protein-Protein Interactions Evolving Accelerated valving Accelerated Amidation by SpyTag/SpyCatcher to Analyze Membrane Dynamics", Ang Ewan Dte Chemie International Edition, vol. 56, No. 52, Dec. 22, 2017 (Dec. 22, 2017), pp. 16521-16525.
Zakeri Bijan et al: "Spontaneous Intermolecular Amide Bond Formation between Side Chains for Irreversible Peptide Targeting", Journal of the American Chemical Society, American Chemical Society, US, vol. 132, No. 13, Apr. 7, 2010 (Apr. 7, 2010), pp. 4526-4527.
B. Zakeri et al: "Peptide tag forming a rapid covalent bond to a protein, through engineering a bacterial adhesin", Proceedings of the National Academy of Sciences, vol. 109, No. 12, Mar. 20, 2012 (Mar. 20, 2012), pp. E690-E697.
Botyanszki et al., 2015, Biotechnology and Bioengineering 112, 2016-2024.
Chen et al., 2011, Proc Natl Acad Sci U S A 108, 11399-11404.
Stranges et al., 2016, Proc Natl Acad Sci U S A 113, E6749-E6756.
Schoene et al., 2016, Scientific Reports 6, 21151.
Brune et al., 2016, Scientific Reports 6, 19234.
Thrane et al., 2016, Journal of Nanobiotechnology 14, 30.
Veggiani et al., 2016 Proc Natl Acad Sci U S A 113, 1202-1207.
Siegmund et al., Sci Rep. Dec. 16, 2016;6:39291.
Alves NJ et al., J Vis Exp. Nov. 16, 2016;(117).
Liu X et al., Sci Rep. Nov. 29, 2016,6:38019.
Hyojin Moon et al., Chem Commun (Camb). Nov. 29, 2016;52(97):14051-14054.
Janitzek CM et al., Malar J. Nov. 8, 2016;15(1):545.
Xiong et al., Chinese Journal of Biochemistry and Molecular Biology (2016), 32 (10): 1141-1149.
Schmid-Burgk et al., Nat Commun. Jul. 28, 2016;7:12338.
Dorval Courchesne et al., ACS Biomater. Sci. Eng. 2017, 3, 5, 733-741.
Pardee K et al., Cell. Sep. 22, 2016;167(1):248-259.
Schloss et al., ACS Biomater. Sci. Eng. 2016, 2, 11, 1856-1861.
Si M et al., PLoS One. Sep. 22, 2016;11(9):e0162318.
Lakshmanan A et al., ACS Nano. Aug. 23, 2016;10(8):7314-22.
Giessen TW, Silver P., Chembiochem. Oct. 17, 2016;17(20):1931-1935.
Gao X et al., Biomacromolecules. Sep. 12, 2016;17(9):2812-9.
Min D et al., Protein Sci. Aug. 2016;25(8):1535-44.
Fuller CW et al., Proc Natl Acad Sci U S A. May 10, 2016;113(19):5233-8.
Alves NJ et al., Sci Rep. Apr. 27, 2016;6:24866.
Wang J et al., Biotechnol Biofuels. Mar. 31, 2016;9:79.
Liu Z et al., Oncoimmunology. Mar. 10, 2016;5(6):e1147641.
Wang XW, Zhang WB., Angew Chem Int Ed Engl. Mar. 1, 2016;55(10):3442-6.
Dovala D et al., Protein Expr Purif. Jan. 2016;117:44-51.
Alves NJ et al., ACS Appl Mater Interfaces. Nov. 11, 2015;7(44):24963-72.
Bedbrook CN et al., Chem Biol. Aug. 20, 2015;22(8):1108-21.
Walden M et al., Elife. Jun. 2, 2015;4.
Leonard JD, Narlikar GJ., Mol Cell. Mar. 5, 2015;57(5):850-9.
Liu Z et al., Sci Rep. Dec. 1, 2014;4:7266.
Nguyen PQ et al., Nat Commun. Sep. 17, 2014;5:4945.
Sun F et al., Proc Natl Acad Sci U S A. Aug. 5, 2014;111(31):11269-74.
Chen AY et al., Nat Mater. May 2014;13(5):515-23.
Zhang WB et al., J Am Chem Soc. Sep. 18, 2013;135(37):13988-97.
Gilbert et al., ACS Synth. Biol. 2017, 6, 6, 957-967.
Fairhead M et al., Journal of the American Chemical Society Sep. 3, 2014;136(35):12355-63.
Schoene C et al., Angewandte Chemie. Jun. 10, 2014;53(24):6101-4. Fierer JO et al, Proc Natl.
Fierer et al., Proc. Nat'l, Acad Sci U S A. Apr. 1, 2014;111(13):E1176-81.
Li L et al., Journal of Molecular Biology. Jan. 23, 2014;426(2):309-17.
Reddington and Howarth, Current Opinion in Chemical Biology (2015); 29, 94-99.
Jaffe et al. Protein F2, a novel fibronecting-binding protein from Streptococcus pyogenes, possesses two binding domains. Molecular Microbiology, 1999, vol. 21, No. 2, pp. 373-384. (Year: 1999).
Kou S, Yang Z, Luo J, Sun F. Entirely recombinant protein-based hydrogels for selective heavy metal sequestration. Polym. Chem., 2017; 8, 6158-6164.

\* cited by examiner

Figure 2

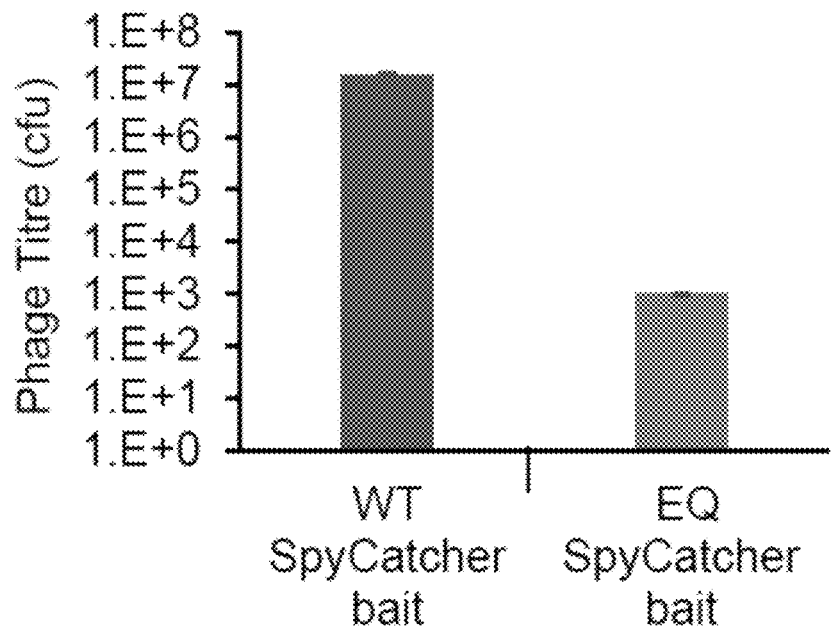

| Clone | Sequence | |
|---|---|---|
| WT | AHIVMVDAYKPTK | (SEQ ID NO: 6) |
| NLib1 | PPVPTIVMVDAYKPTK | (SEQ ID NO: 15) |
| NLib2 | RPCYVIVMVDAYKPTK | (SEQ ID NO: 16) |
| NLib3 | GRYAWIVMVDAYKPTK | (SEQ ID NO: 17) |
| CLib1 | VPTIVMVDCYKRY | (SEQ ID NO: 18) |
| CLib2 | VPTIVMVDCCLFC | (SEQ ID NO: 19) |
| CLib3 | VPTIVMVDFWMRC | (SEQ ID NO: 20) |
| CLib4 | VPTIVMVDCRLDS | (SEQ ID NO: 21) |
| CLib5 | VPTIVMVDCQLAS | (SEQ ID NO: 22) |
| CLib6 | VPTIVMVDCSLSP | (SEQ ID NO: 23) |
| CLib7 | VPTIVMVDPYQGT | (SEQ ID NO: 24) |
| CLib8 | VPTIVMVDYPSRC | (SEQ ID NO: 25) |
| CLib9 | VPTIVMVDCYKRY | (SEQ ID NO: 26) |
| CLib10 | VPTIVMVDFILAN | (SEQ ID NO: 27) |
| SpyTag002 | VPTIVMVDAYKRYK | (SEQ ID NO: 3) |

Figure 4
A
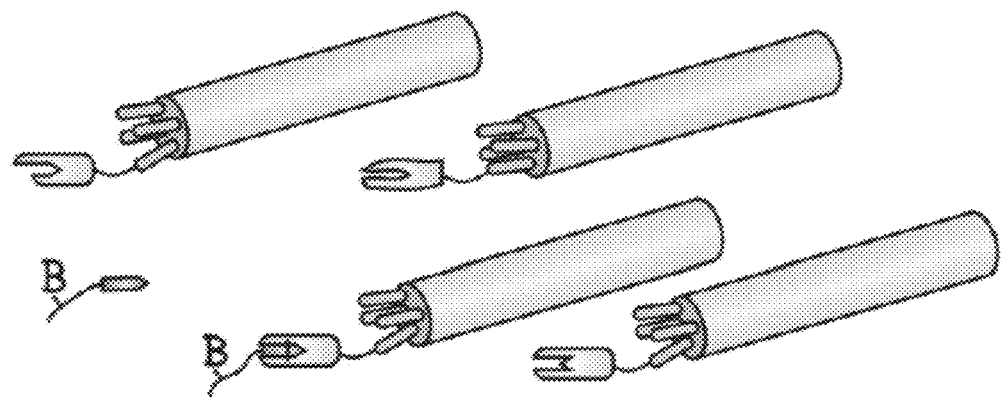
React SpyCatcher-phage library with biotin (B)-SpyTag bait and proceed as before.
B
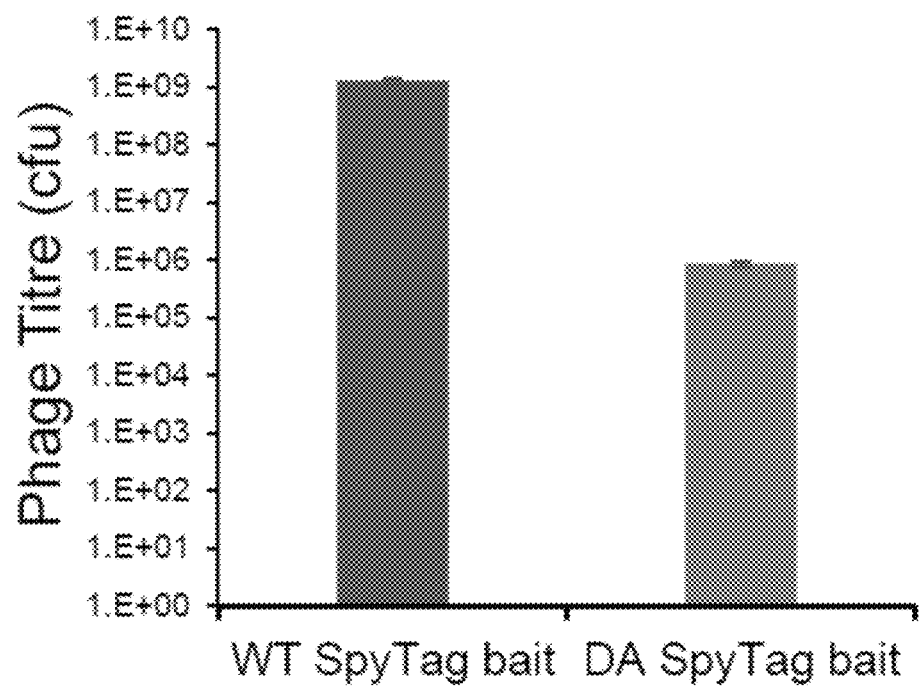

Figure 5

```
            1         10        20        30        40        50        60
      WT  GAMVDTLSGLSSEQGQSGDMTIEEDSATHIKFSKRDEDGKELAGATMELRDSSGKTISTW
     L1C1 GAMVDTLSGLSSDQGQSCDMTTEEDSATHVKFSKRDEDGRELAGAAMELRDPSGETISTW
     L1C4 GAMVDTFSGLSGEQGRSGDMTTEEDSATHIKFSKRDEDGRELAGATMELRDSSGKTISTW
     L1C2 GAMVDTLSGLSSEQGRSGDMTSEEDSATHIKFSKRDEDGRELAGATMELRDSSGKTISTW
     L2C1 GAMVDTLSGLSSEQCQSGDMTTEEDSATHIKFSKRDEDGRELAGATMELRDSSGKTISTW
     L1C3 GAMVDTLSGLSSEQGQSGDMTTEEDSATHIKFSKRDEDGRELAGATMELRDSSGKTISTW
     L1C6 GAMVDTLSGLSGEQGPSGDMTTEEDSATHIKFSKRDEDGRELAGATMELRDSSGKTISTW
     L2C8 GAMVDTLSGLSSEQGQSGDMTTEEDSATHIKFSKRDEDGRELAGATMELRDSSGKTISTW
    SC002 GAMVTTLSGLSGEQGPSGDMTTEEDSATHIKFSKRDEDGRELAGATMELRDSSGKTISTW
          ****.*:****.:*  *  *** *******:**********:*****:***** **:*****

70        80        90       100       110
      WT  ISDGQVKDFYLYPGKYTFVETAAPDGYEVATAITFTVNEQGQVTVNGKATKGDAHI (SEQ ID NO:7)
     L1C1 ISDGHVKDFYLYPGKYTFVETAAPDGYEVASAITFTVNEQGQVTVYGKATKGDAHT (SEQ ID NO:33)
     L1C4 ISDGHVKDFYLYPGKYTFVETAAPDGYEVATAITFTVNERGQVTVNGKATKGDAHT (SEQ ID NO:34)
     L1C2 ISDGHVKDFYLYPGEYTFVETAAPDGYEVATAITFTVNEQGQVTVNGKATKGDAHT (SEQ ID NO:35)
     L2C1 ISDGRVKDFYLYPGKYTFVETAAPDGYEVATAITFTVNEQGQVTVNGKATKGDAHT (SEQ ID NO:36)
     L1C3 TSDGHVKDFYLYPGKYTFVETAAPDGYEVAAITFTVNEQGQVTVNGKATKGDAHT (SEQ ID NO:37)
     L1C6 ISDGHVKDFYLYPGKYTFVETAAPDGYEVATAITFTVNEQGQVTVNGEATKGDAHT (SEQ ID NO:38)
     L2C8 ISDGHVKDFYLYPGKYTFVETAAPDGYEVATAITFTVNEQGQVTVNGEATKGDAHT (SEQ ID NO:39)
    SC002 ISDGHVKDFYLYPGKYTFVETAAPDGYEVATAITFTVNEQGQVTVNGEATKGDAHT (SEQ ID NO:40)
          ***:********:*****************:*******:***** *:*******
```

A

B

SpyTag: IVMVDA (SEQ ID NO: 41)
SpyCatcher L1C6: GAMVDT (SEQ ID NO: 42)
SpyCatcher002: GAMVTT (SEQ ID NO: 43)

| Protein | $T_m$ (°C) |
|---|---|
| SpyCatcher002 | 49.9 |
| SpyCatcher | 48.5 |

Figure 9
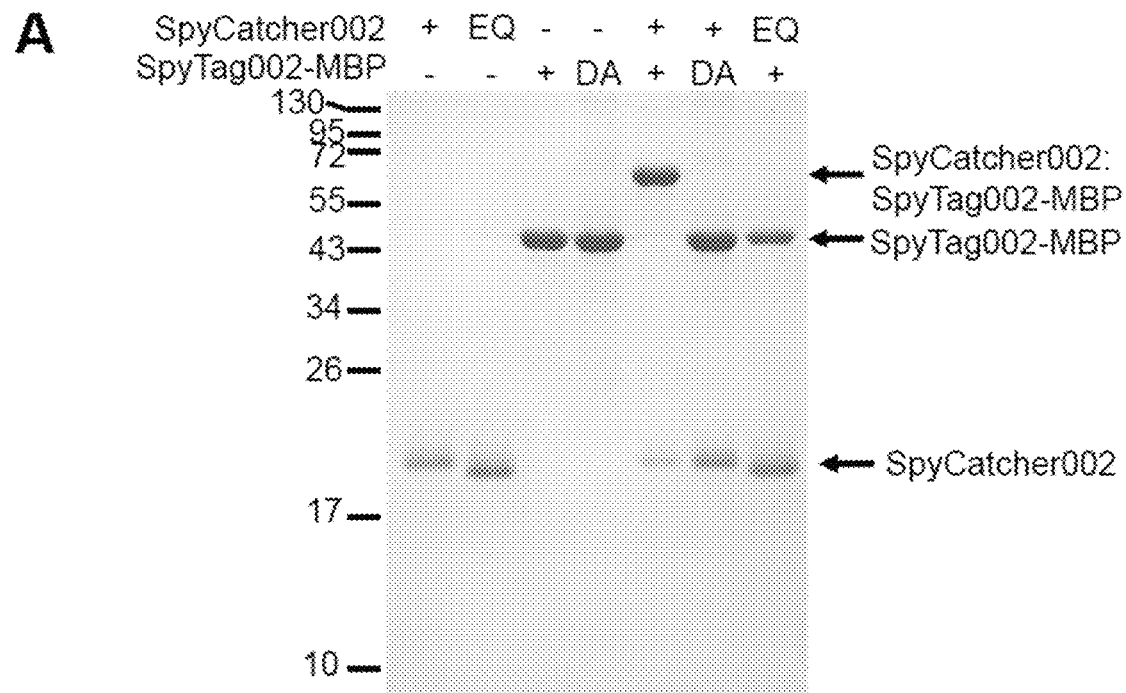
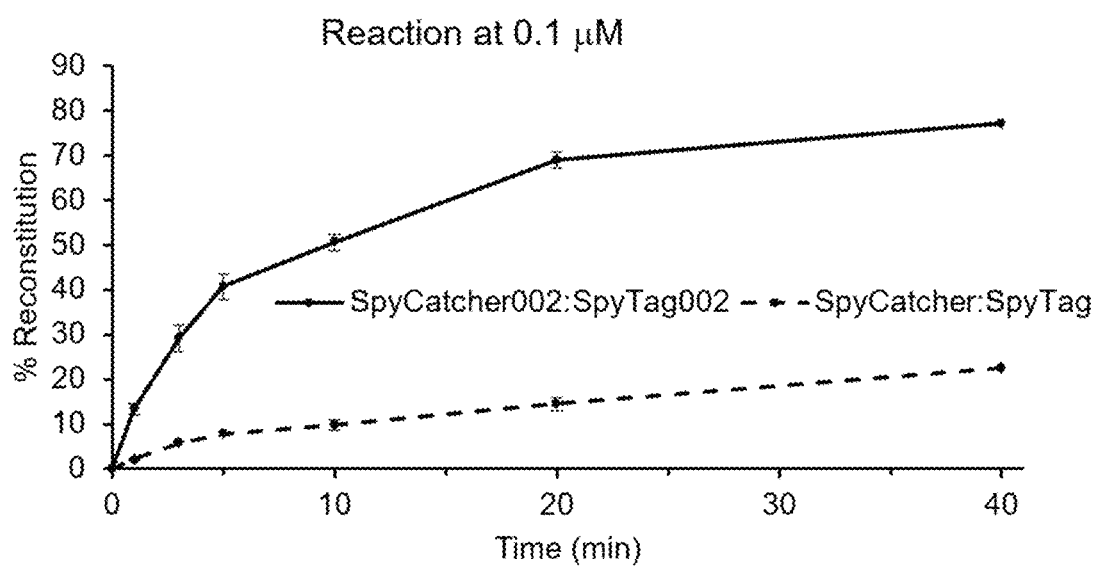

Figure 10
A
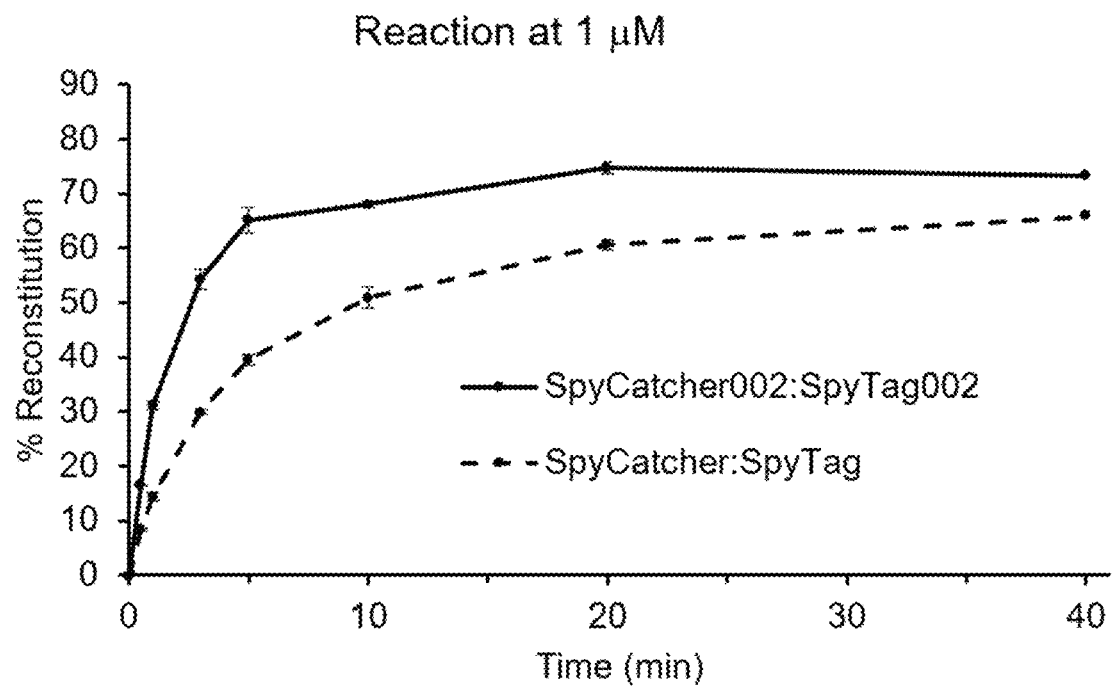
B
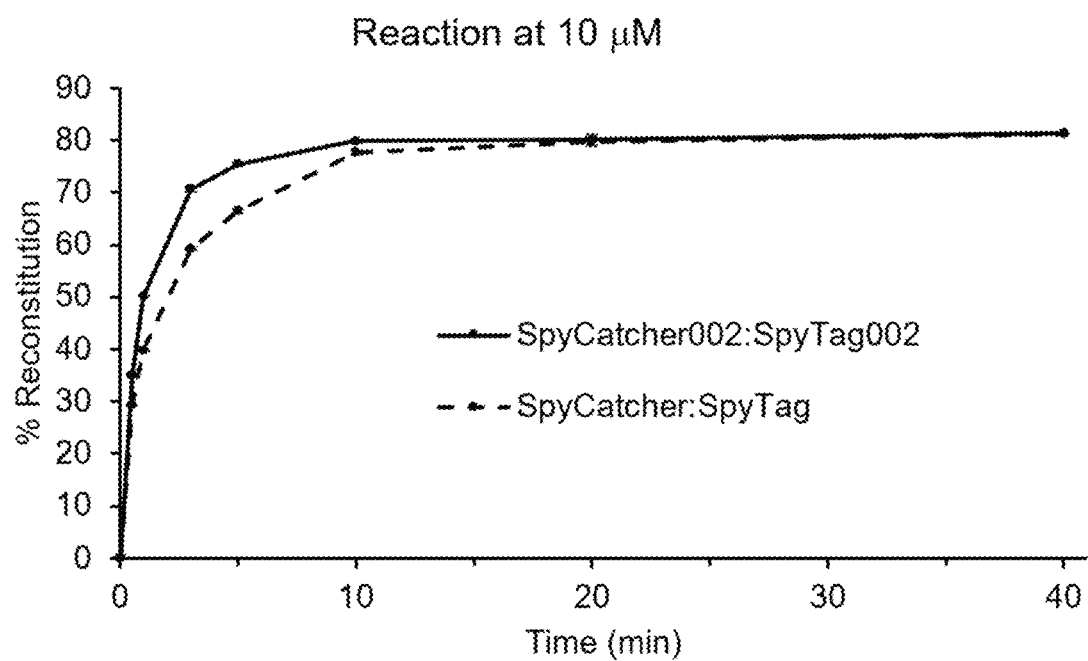

Figure 15
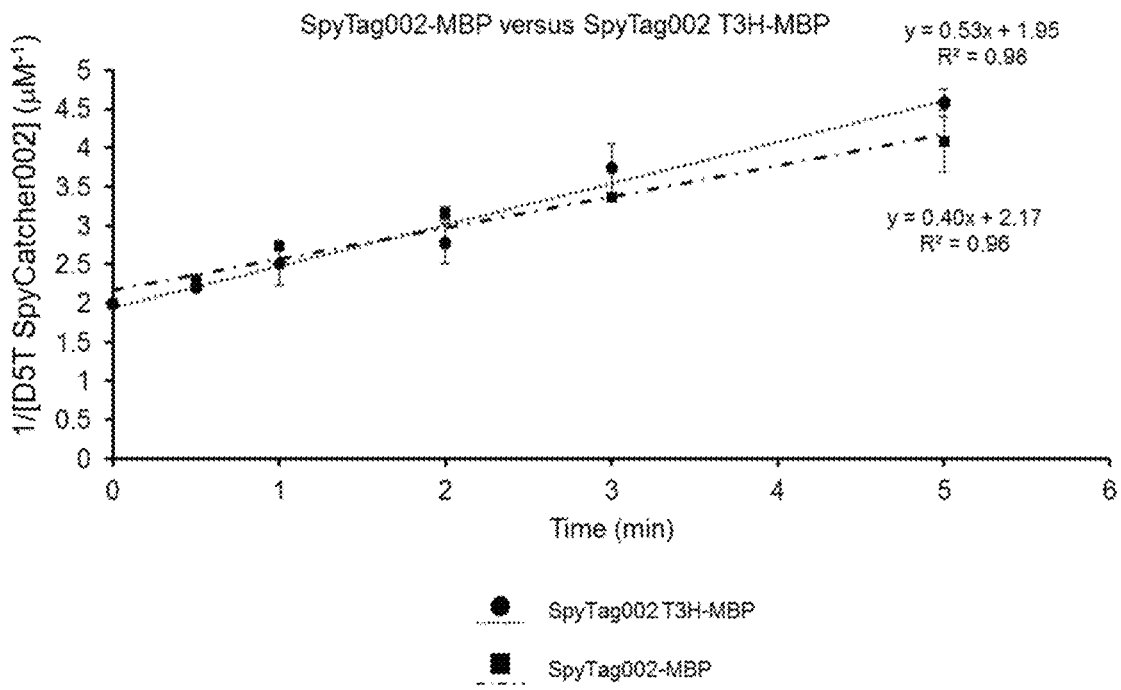
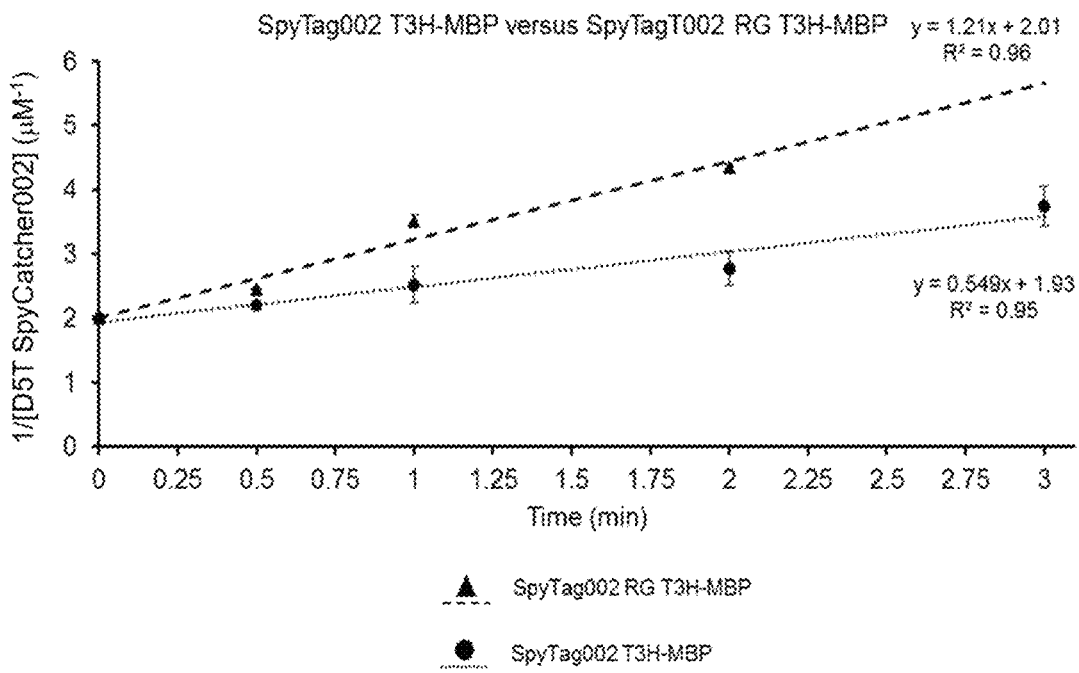

SEQUENCE LISTING

<160> NUMBER OF SEQ ID NOS: 101

<210> SEQ ID NO 1
<211> LENGTH: 16
<212> TYPE: PRT
<213> ORGANISM: Artificial Sequence
<220> FEATURE:

```
<223> OTHER INFORMATION: SpyTag002 consensus
<220> FEATURE:
<221> NAME/KEY: MISC_FEATURE
<222> LOCATION: (1)..(1)
<223> OTHER INFORMATION: X is arginine or no amino acid
<220> FEATURE:
<221> NAME/KEY: MISC_FEATURE
<222> LOCATION: (2)..(2)
<223> OTHER INFORMATION: X is glycine or no amino acid
<220> FEATURE:
<221> NAME/KEY: MISC_FEATURE
<222> LOCATION: (5)..(5)
<223> OTHER INFORMATION: X is threonine or histidine, preferably
     histidine
<220> FEATURE:
<221> NAME/KEY: MISC_FEATURE
<222> LOCATION: (11)..(11)
<223> OTHER INFORMATION: X is alanine, glycine or valine, preferably
     alanine
<220> FEATURE:
<221> NAME/KEY: MISC_FEATURE
<222> LOCATION: (14)..(14)
<223> OTHER INFORMATION: X is arginine or lysine, preferably arginine

<400> SEQUENCE: 1

Xaa Xaa Val Pro Xaa Ile Val Met Val Asp Xaa Tyr Lys Xaa Tyr Lys
1               5                   10                  15

<210> SEQ ID NO 2
<211> LENGTH: 116
<212> TYPE: PRT
<213> ORGANISM: Artificial Sequence
<220> FEATURE:
<223> OTHER INFORMATION: SpyCatcher002 A92P Q100D

<400> SEQUENCE: 2

Gly Ala Met Val Thr Thr Leu Ser Gly Leu Ser Gly Glu Gln Gly Pro
1               5                   10                  15

Ser Gly Asp Met Thr Thr Glu Glu Asp Ser Ala Thr His Ile Lys Phe
                20                  25                  30

Ser Lys Arg Asp Glu Asp Gly Arg Glu Leu Ala Gly Ala Thr Met Glu
            35                  40                  45

Leu Arg Asp Ser Ser Gly Lys Thr Ile Ser Thr Trp Ile Ser Asp Gly
50                  55                  60

His Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Pro Ile Thr Phe Thr
                85                  90                  95

Val Asn Glu Asp Gly Gln Val Thr Val Asn Gly Glu Ala Thr Lys Gly
            100                 105                 110

Asp Ala His Thr
        115

<210> SEQ ID NO 3
<211> LENGTH: 14
<212> TYPE: PRT
<213> ORGANISM: Artificial Sequence
<220> FEATURE:
<223> OTHER INFORMATION: SpyTag002

<400> SEQUENCE: 3

Val Pro Thr Ile Val Met Val Asp Ala Tyr Lys Arg Tyr Lys
1               5                   10

<210> SEQ ID NO 4
<211> LENGTH: 14
```

```
<212> TYPE: PRT
<213> ORGANISM: Artificial Sequence
<220> FEATURE:
<223> OTHER INFORMATION: SpyTag002 T3H

<400> SEQUENCE: 4

Val Pro His Ile Val Met Val Asp Ala Tyr Lys Arg Tyr Lys
1               5                   10

<210> SEQ ID NO 5
<211> LENGTH: 16
<212> TYPE: PRT
<213> ORGANISM: Artificial Sequence
<220> FEATURE:
<223> OTHER INFORMATION: SpyTag002 RG-T3H

<400> SEQUENCE: 5

Arg Gly Val Pro His Ile Val Met Val Asp Ala Tyr Lys Arg Tyr Lys
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: SpyTag

<400> SEQUENCE: 6

Ala His Ile Val Met Val Asp Ala Tyr Lys Pro Thr Lys
1               5                   10

<210> SEQ ID NO 7
<211> LENGTH: 116
<212> TYPE: PRT
<213> ORGANISM: Artificial Sequence
<220> FEATURE:
<223> OTHER INFORMATION: SpyCatcher

<400> SEQUENCE: 7

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile
        115

<210> SEQ ID NO 8
<211> LENGTH: 14
<212> TYPE: PRT
<213> ORGANISM: Artificial Sequence
<220> FEATURE:
<223> OTHER INFORMATION: Truncated SpyTag002 consensus
<220> FEATURE:
<221> NAME/KEY: MISC_FEATURE
```

```
<222> LOCATION: (3)..(3)
<223> OTHER INFORMATION: X is threonine or histidine, preferably
      histidine
<220> FEATURE:
<221> NAME/KEY: MISC_FEATURE
<222> LOCATION: (9)..(9)
<223> OTHER INFORMATION: X is alanine, glycine or valine, preferably
      alanine
<220> FEATURE:
<221> NAME/KEY: MISC_FEATURE
<222> LOCATION: (12)..(12)
<223> OTHER INFORMATION: X is arginine or lysine, preferably arginine

<400> SEQUENCE: 8

Val Pro Xaa Ile Val Met Val Asp Xaa Tyr Lys Xaa Tyr Lys
1               5                   10

<210> SEQ ID NO 9
<211> LENGTH: 16
<212> TYPE: PRT
<213> ORGANISM: Artificial Sequence
<220> FEATURE:
<223> OTHER INFORMATION: SpyTag002 RG variant
<220> FEATURE:
<221> NAME/KEY: MISC_FEATURE
<222> LOCATION: (5)..(5)
<223> OTHER INFORMATION: X is threonine or histidine, preferably
      histidine
<220> FEATURE:
<221> NAME/KEY: MISC_FEATURE
<222> LOCATION: (11)..(11)
<223> OTHER INFORMATION: X is alanine, glycine or valine, preferably
      alanine
<220> FEATURE:
<221> NAME/KEY: MISC_FEATURE
<222> LOCATION: (14)..(14)
<223> OTHER INFORMATION: X is arginine or lysine, preferably arginine

<400> SEQUENCE: 9

Arg Gly Val Pro Xaa Ile Val Met Val Asp Xaa Tyr Lys Xaa Tyr Lys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: SpyTag002 RG H5 variant
<220> FEATURE:
<221> NAME/KEY: MISC_FEATURE
<222> LOCATION: (11)..(11)
<223> OTHER INFORMATION: X is alanine, glycine or valine, preferably
      alanine
<220> FEATURE:
<221> NAME/KEY: MISC_FEATURE
<222> LOCATION: (14)..(14)
<223> OTHER INFORMATION: X is arginine or lysine, preferably arginine

<400> SEQUENCE: 10

Arg Gly Val Pro His Ile Val Met Val Asp Xaa Tyr Lys Xaa Tyr Lys
1               5                   10                  15

<210> SEQ ID NO 11
<211> LENGTH: 42
<212> TYPE: DNA
<213> ORGANISM: Artificial Sequence
<220> FEATURE:
<223> OTHER INFORMATION: nucleotide sequence of SEQ ID NO: 3

<400> SEQUENCE: 11
gtgccgacca tcgtgatggt ggacgcctac aagcgttaca ag                42
```

<210> SEQ ID NO 12
<211> LENGTH: 42
<212> TYPE: DNA
<213> ORGANISM: Artificial Sequence
<220> FEATURE:
<223> OTHER INFORMATION: nucleotide sequence of SEQ ID NO: 4

<400> SEQUENCE: 12
gtgcctcata tcgtgatggt ggacgcctac aagcgttaca ag         42

<210> SEQ ID NO 13
<211> LENGTH: 48
<212> TYPE: DNA
<213> ORGANISM: Artificial Sequence
<220> FEATURE:
<223> OTHER INFORMATION: nucleotide sequence of SEQ ID NO: 5

<400> SEQUENCE: 13
cgtggcgtgc ctcatatcgt gatggtggac gcctacaagc gttacaag         48

<210> SEQ ID NO 14
<211> LENGTH: 348
<212> TYPE: DNA
<213> ORGANISM: Artificial Sequence
<220> FEATURE:
<223> OTHER INFORMATION: nucleotide sequence of SEQ ID NO: 2

<400> SEQUENCE: 14
ggcgccatgg taaccacctt atcaggttta tcaggtgagc aaggtccgtc cggtgatatg         60
acaactgaag aagatagtgc tacccatatt aaattctcaa aacgtgatga ggacggccgt        120
gagttagctg gtgcaactat ggagttgcgt gattcatctg gtaaaactat tagtacatgg        180
atttcagatg gacatgtgaa ggatttctac ctgtatccag aaaatatac atttgtcgaa         240 accgcagcac cagacggtta tgaggtagca actccaatta cctttacagt taatgaggac        300
ggtcaggtta ctgtaaatgg cgaagcaact aaaggtgacg ctcatact                     348

<210> SEQ ID NO 15
<211> LENGTH: 16
<212> TYPE: PRT
<213> ORGANISM: Artificial Sequence
<220> FEATURE:
<223> OTHER INFORMATION: NLib1

<400> SEQUENCE: 15

Pro Pro Val Pro Thr Ile Val Met Val Asp Ala Tyr Lys Pro Thr Lys
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: NLib2

<400> SEQUENCE: 16

Arg Pro Cys Tyr Val Ile Val Met Val Asp Ala Tyr Lys Pro Thr Lys
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: NLib3

<400> SEQUENCE: 17

Gly Arg Tyr Ala Trp Ile Val Met Val Asp Ala Tyr Lys Pro Thr Lys
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: CLib1

<400> SEQUENCE: 18

Val Pro Thr Ile Val Met Val Asp Cys Tyr Lys Arg Tyr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: CLib2

<400> SEQUENCE: 19

Val Pro Thr Ile Val Met Val Asp Cys Cys Leu Phe Cys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: CLib3

<400> SEQUENCE: 20

Val Pro Thr Ile Val Met Val Asp Phe Trp Met Arg Cys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: CLib4

<400> SEQUENCE: 21

Val Pro Thr Ile Val Met Val Asp Cys Arg Leu Asp Ser
1               5                   10

<210> SEQ ID NO 22
<211> LENGTH: 13
<212> TYPE: PRT
<213> ORGANISM: Artificial Sequence
<220> FEATURE:
<223> OTHER INFORMATION: CLib5

<400> SEQUENCE: 22

Val Pro Thr Ile Val Met Val Asp Cys Gln Leu Ala Ser
1               5                   10

<210> SEQ ID NO 23
<211> LENGTH: 13
<212> TYPE: PRT
<213> ORGANISM: Artificial Sequence
<220> FEATURE:
<223> OTHER INFORMATION: CLib6

```
<400> SEQUENCE: 23

Val Pro Thr Ile Val Met Val Asp Cys Ser Leu Ser Pro
1               5                   10

<210> SEQ ID NO 24
<211> LENGTH: 13
<212> TYPE: PRT
<213> ORGANISM: Artificial Sequence
<220> FEATURE:
<223> OTHER INFORMATION: CLib7

<400> SEQUENCE: 24

Val Pro Thr Ile Val Met Val Asp Pro Tyr Gln Gly Thr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: CLib8

<400> SEQUENCE: 25

Val Pro Thr Ile Val Met Val Asp Tyr Pro Ser Arg Cys
1               5                   10

<210> SEQ ID NO 26
<211> LENGTH: 13
<212> TYPE: PRT
<213> ORGANISM: Artificial Sequence
<220> FEATURE:
<223> OTHER INFORMATION: CLib9

<400> SEQUENCE: 26

Val Pro Thr Ile Val Met Val Asp Cys Tyr Lys Arg Tyr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: CLib10

<400> SEQUENCE: 27

Val Pro Thr Ile Val Met Val Asp Phe Ile Leu Ala Asn
1               5                   10

<210> SEQ ID NO 28
<211> LENGTH: 5
<212> TYPE: PRT
<213> ORGANISM: Artificial Sequence
<220> FEATURE:
<223> OTHER INFORMATION: N-terminus of NLib1

<400> SEQUENCE: 28

Pro Pro Val Pro Thr
1               5

<210> SEQ ID NO 29
<211> LENGTH: 4
<212> TYPE: PRT
<213> ORGANISM: Artificial Sequence
<220> FEATURE:
<223> OTHER INFORMATION: N-terminus of NLib1-1

<400> SEQUENCE: 29
```

```
Pro Val Pro Thr
1

<210> SEQ ID NO 30
<211> LENGTH: 15
<212> TYPE: PRT
<213> ORGANISM: Artificial Sequence
<220> FEATURE:
<223> OTHER INFORMATION: NLib1-1

<400> SEQUENCE: 30

Pro Val Pro Thr Ile Val Met Val Asp Ala Tyr Lys Pro Thr Lys
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: NLib1-2

<400> SEQUENCE: 31

Val Pro Thr Ile Val Met Val Asp Ala Tyr Lys Pro Thr Lys
1               5                   10

<210> SEQ ID NO 32
<211> LENGTH: 13
<212> TYPE: PRT
<213> ORGANISM: Artificial Sequence
<220> FEATURE:
<223> OTHER INFORMATION: NLib1-3

<400> SEQUENCE: 32

Pro Thr Ile Val Met Val Asp Ala Tyr Lys Pro Thr Lys
1               5                   10

<210> SEQ ID NO 33
<211> LENGTH: 116
<212> TYPE: PRT
<213> ORGANISM: Artificial Sequence
<220> FEATURE:
<223> OTHER INFORMATION: L1C1

<400> SEQUENCE: 33

Gly Ala Met Val Asp Thr Leu Ser Gly Leu Ser Ser Asp Gln Gly Gln
1               5                   10                  15

Ser Cys Asp Met Thr Thr Glu Glu Asp Ser Ala Thr His Val Lys Phe
                20                  25                  30

Ser Lys Arg Asp Glu Asp Gly Arg Glu Leu Ala Gly Ala Ala Met Glu
            35                  40                  45

Leu Arg Asp Pro Ser Gly Glu Thr Ile Ser Thr Trp Ile Ser Asp Gly
        50                  55                  60

His Val Lys Asp Phe Tyr Leu Tyr Pro Gly Lys Tyr Thr Phe Val Glu
65                  70                  75                  80

Thr Ala Ala Pro Asp Gly Tyr Glu Val Ala Ser Ala Ile Thr Phe Thr
                85                  90                  95

Val Asn Glu Gln Gly Gln Val Thr Val Tyr Gly Lys Ala Thr Lys Gly
                100                 105                 110

Asp Ala His Thr
        115

<210> SEQ ID NO 34
```

<211> LENGTH: 116
<212> TYPE: PRT
<213> ORGANISM: Artificial Sequence
<220> FEATURE:
<223> OTHER INFORMATION: L1C4

<400> SEQUENCE: 34

Gly Ala Met Val Asp Thr Phe Ser Gly Leu Ser Gly Glu Gln Gly Arg
1               5                   10                  15

Ser Gly Asp Met Thr Thr Glu Glu Asp Ser Ala Thr His Ile Lys Phe
            20                  25                  30

Ser Lys Arg Asp Glu Asp Gly Arg Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

His Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Arg Gly Gln Val Thr Val Asn Gly Lys Ala Thr Lys Gly
            100                 105                 110

Asp Ala His Thr
        115

<210> SEQ ID NO 35
<211> LENGTH: 116
<212> TYPE: PRT
<213> ORGANISM: Artificial Sequence
<220> FEATURE:
<223> OTHER INFORMATION: L1C2

<400> SEQUENCE: 35

Gly Ala Met Val Asp Thr Leu Ser Gly Leu Ser Ser Glu Gln Gly Arg
1               5                   10                  15

Ser Gly Asp Met Thr Ser Glu Glu Asp Ser Ala Thr His Ile Lys Phe
            20                  25                  30

Ser Lys Arg Asp Glu Asp Gly Arg Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

His Val Lys Asp Phe Tyr Leu Tyr Pro Gly Glu Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Thr
        115

<210> SEQ ID NO 36
<211> LENGTH: 116
<212> TYPE: PRT
<213> ORGANISM: Artificial Sequence
<220> FEATURE:
<223> OTHER INFORMATION: L2C1

<400> SEQUENCE: 36

Gly Ala Met Val Asp Thr Leu Ser Gly Leu Ser Ser Glu Gln Cys Gln
1               5                   10                  15

Ser Gly Asp Met Thr Thr Glu Glu Asp Ser Ala Thr His Ile Lys Phe
            20                  25                  30

Ser Lys Arg Asp Glu Asp Gly Arg Glu Leu Ala Gly Ala Thr Met Glu
        35                  40                  45

Leu Arg Asp Ser Ser Gly Lys Thr Ile Ser Thr Trp Ile Ser Asp Gly
 50                  55                  60

Arg Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Thr
        115

<210> SEQ ID NO 37
<211> LENGTH: 116
<212> TYPE: PRT
<213> ORGANISM: Artificial Sequence
<220> FEATURE:
<223> OTHER INFORMATION: L1C3

<400> SEQUENCE: 37

Gly Ala Met Val Asp Thr Leu Ser Gly Leu Ser Ser Glu Gln Gly Gln
1               5                   10                  15

Ser Gly Asp Met Thr Thr Glu Glu Asp Ser Ala Thr His Ile Lys Phe
            20                  25                  30

Ser Lys Arg Asp Glu Asp Gly Arg Glu Leu Ala Gly Ala Thr Met Glu
        35                  40                  45

Leu Arg Asp Ser Ser Gly Lys Thr Ile Ser Thr Trp Thr Ser Asp Gly
 50                  55                  60

His Val Lys Asp Phe Tyr Leu Tyr Pro Gly Lys Tyr Thr Phe Val Glu
65                  70                  75                  80

Thr Ala Ala Pro Asp Gly Tyr Glu Val Ala Ala Ile Thr Phe Thr
                85                  90                  95

Val Asn Glu Gln Gly Gln Val Thr Val Asn Gly Lys Ala Thr Lys Gly
            100                 105                 110

Asp Ala His Thr
        115

<210> SEQ ID NO 38
<211> LENGTH: 116
<212> TYPE: PRT
<213> ORGANISM: Artificial Sequence
<220> FEATURE:
<223> OTHER INFORMATION: L1C6

<400> SEQUENCE: 38

Gly Ala Met Val Asp Thr Leu Ser Gly Leu Ser Gly Glu Gln Gly Pro
1               5                   10                  15

Ser Gly Asp Met Thr Thr Glu Glu Asp Ser Ala Thr His Ile Lys Phe
            20                  25                  30

Ser Lys Arg Asp Glu Asp Gly Arg Glu Leu Ala Gly Ala Thr Met Glu
        35                  40                  45

Leu Arg Asp Ser Ser Gly Lys Thr Ile Ser Thr Trp Ile Ser Asp Gly
 50                  55                  60

His Val Lys Asp Phe Tyr Leu Tyr Pro Gly Lys Tyr Thr Phe Val Glu
65                  70                  75                  80

```
Thr Ala Ala Pro Asp Gly Tyr Glu Val Ala Thr Ala Ile Thr Phe Thr
                85                  90                  95

Val Asn Glu Gln Gly Gln Val Thr Val Asn Gly Glu Ala Thr Lys Gly
            100                 105                 110

Asp Ala His Thr
        115

<210> SEQ ID NO 39
<211> LENGTH: 116
<212> TYPE: PRT
<213> ORGANISM: Artificial Sequence
<220> FEATURE:
<223> OTHER INFORMATION: L2C8

<400> SEQUENCE: 39

Gly Ala Met Val Asp Thr Leu Ser Gly Leu Ser Ser Glu Gln Gly Gln
1               5                   10                  15

Ser Gly Asp Met Thr Thr Glu Glu Asp Ser Ala Thr His Ile Lys Phe
            20                  25                  30

Ser Lys Arg Asp Glu Asp Gly Arg Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

His Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Glu Ala Thr Lys Gly
            100                 105                 110

Asp Ala His Thr
        115

<210> SEQ ID NO 40
<211> LENGTH: 116
<212> TYPE: PRT
<213> ORGANISM: Artificial Sequence
<220> FEATURE:
<223> OTHER INFORMATION: SpyCatcher002 (SC002)

<400> SEQUENCE: 40

Gly Ala Met Val Thr Thr Leu Ser Gly Leu Ser Gly Glu Gln Gly Pro
1               5                   10                  15

Ser Gly Asp Met Thr Thr Glu Glu Asp Ser Ala Thr His Ile Lys Phe
            20                  25                  30

Ser Lys Arg Asp Glu Asp Gly Arg Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

His Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Glu Ala Thr Lys Gly
            100                 105                 110

Asp Ala His Thr
        115
```

```
<210> SEQ ID NO 41
<211> LENGTH: 6
<212> TYPE: PRT
<213> ORGANISM: Artificial Sequence
<220> FEATURE:
<223> OTHER INFORMATION: Portion of SpyTag

<400> SEQUENCE: 41

Ile Val Met Val Asp Ala
1               5

<210> SEQ ID NO 42
<211> LENGTH: 6
<212> TYPE: PRT
<213> ORGANISM: Artificial Sequence
<220> FEATURE:
<223> OTHER INFORMATION: N-terminus of SpyCatcher L1C6

<400> SEQUENCE: 42

Gly Ala Met Val Asp Thr
1               5

<210> SEQ ID NO 43
<211> LENGTH: 6
<212> TYPE: PRT
<213> ORGANISM: Artificial Sequence
<220> FEATURE:
<223> OTHER INFORMATION: N-terminus of L1C6 D5T

<400> SEQUENCE: 43

Gly Ala Met Val Thr Thr
1               5

<210> SEQ ID NO 44
<211> LENGTH: 116
<212> TYPE: PRT
<213> ORGANISM: Artificial Sequence
<220> FEATURE:
<223> OTHER INFORMATION: SpyCatcher002 D5A

<400> SEQUENCE: 44

Gly Ala Met Val Ala Thr Leu Ser Gly Leu Ser Gly Glu Gln Gly Pro
1               5                   10                  15

Ser Gly Asp Met Thr Thr Glu Glu Asp Ser Ala Thr His Ile Lys Phe
                20                  25                  30

Ser Lys Arg Asp Glu Asp Gly Arg Glu Leu Ala Gly Ala Thr Met Glu
            35                  40                  45

Leu Arg Asp Ser Ser Gly Lys Thr Ile Ser Thr Trp Ile Ser Asp Gly
        50                  55                  60

His Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Glu Ala Thr Lys Gly
                100                 105                 110

Asp Ala His Thr
        115

<210> SEQ ID NO 45
<211> LENGTH: 116
<212> TYPE: PRT
<213> ORGANISM: Artificial Sequence
<220> FEATURE:
<223> OTHER INFORMATION: SpyCatcher002 D5A A92P
```

<400> SEQUENCE: 45

Gly Ala Met Val Ala Thr Leu Ser Gly Leu Ser Gly Glu Gln Gly Pro
1               5                   10                  15

Ser Gly Asp Met Thr Thr Glu Glu Asp Ser Ala Thr His Ile Lys Phe
            20                  25                  30

Ser Lys Arg Asp Glu Asp Gly Arg Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

His Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Pro Ile Thr Phe Thr
                85                  90                  95

Val Asn Glu Gln Gly Gln Val Thr Val Asn Gly Glu Ala Thr Lys Gly
                100                 105                 110

Asp Ala His Thr
        115

<210> SEQ ID NO 46
<211> LENGTH: 116
<212> TYPE: PRT
<213> ORGANISM: Artificial Sequence
<220> FEATURE:
<223> OTHER INFORMATION: SpyCatcher002 D5A Q100D

<400> SEQUENCE: 46

Gly Ala Met Val Ala Thr Leu Ser Gly Leu Ser Gly Glu Gln Gly Pro
1               5                   10                  15

Ser Gly Asp Met Thr Thr Glu Glu Asp Ser Ala Thr His Ile Lys Phe
            20                  25                  30

Ser Lys Arg Asp Glu Asp Gly Arg Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

His Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Asp Gly Gln Val Thr Val Asn Gly Glu Ala Thr Lys Gly
                100                 105                 110

Asp Ala His Thr
        115

<210> SEQ ID NO 47
<211> LENGTH: 116
<212> TYPE: PRT
<213> ORGANISM: Artificial Sequence
<220> FEATURE:
<223> OTHER INFORMATION: SpyCatcher002 D5A A92P Q100D

<400> SEQUENCE: 47

Gly Ala Met Val Ala Thr Leu Ser Gly Leu Ser Gly Glu Gln Gly Pro
1               5                   10                  15

Ser Gly Asp Met Thr Thr Glu Glu Asp Ser Ala Thr His Ile Lys Phe
            20                  25                  30

Ser Lys Arg Asp Glu Asp Gly Arg Glu Leu Ala Gly Ala Thr Met Glu
        35                  40                  45

```
Leu Arg Asp Ser Ser Gly Lys Thr Ile Ser Thr Trp Ile Ser Asp Gly
 50                  55                  60

His Val Lys Asp Phe Tyr Leu Tyr Pro Gly Lys Tyr Thr Phe Val Glu
 65                  70                  75                  80

Thr Ala Ala Pro Asp Gly Tyr Glu Val Ala Thr Pro Ile Thr Phe Thr
                 85                  90                  95

Val Asn Glu Asp Gly Gln Val Thr Val Asn Gly Glu Ala Thr Lys Gly
            100                 105                 110

Asp Ala His Thr
        115

<210> SEQ ID NO 48
<211> LENGTH: 30
<212> TYPE: DNA
<213> ORGANISM: Artificial Sequence
<220> FEATURE:
<223> OTHER INFORMATION: Primer

<400> SEQUENCE: 48
gattacgaca tcccaacgac cgaaaacctg                                       30

<210> SEQ ID NO 49
<211> LENGTH: 77
<212> TYPE: DNA
<213> ORGANISM: Artificial Sequence
<220> FEATURE:
<223> OTHER INFORMATION: Primer

<400> SEQUENCE: 49
gcctgaacga tattttgaa gcgcagaaaa ttgaatggca tgaaggcgat tacgacatcc       60
caacgaccga aaacctg                                                    77

<210> SEQ ID NO 50
<211> LENGTH: 33
<212> TYPE: DNA
<213> ORGANISM: Artificial Sequence
<220> FEATURE:
<223> OTHER INFORMATION: Primer

<400> SEQUENCE: 50
gtgatggtga tggtgatggt agtacgacat atg                                   33

<210> SEQ ID NO 51
<211> LENGTH: 80
<212> TYPE: DNA
<213> ORGANISM: Artificial Sequence
<220> FEATURE:
<223> OTHER INFORMATION: Primer

<400> SEQUENCE: 51
tgccattcaa ttttctgcgc ttcaaaaata tcgttcaggc cgctgccgtg atggtgatgg      60
tgatggtagt acgacatatg                                                 80

<210> SEQ ID NO 52
<211> LENGTH: 82
<212> TYPE: DNA
<213> ORGANISM: Artificial Sequence
<220> FEATURE:
<223> OTHER INFORMATION: Primer

<400> SEQUENCE: 52
attacatatg ggtctgaatg atattttcga agcgcagaaa attgaatggc atgaaggtag      60
```
cggagcccac atcgtgatgg tg                                              82

<210> SEQ ID NO 53
<211> LENGTH: 31
<212> TYPE: DNA
<213> ORGANISM: Artificial Sequence
<220> FEATURE:
<223> OTHER INFORMATION: Primer

<400> SEQUENCE: 53
ggggaagctt ttacgagctc gaattagtct g                                    31

<210> SEQ ID NO 54
<211> LENGTH: 29
<212> TYPE: DNA
<213> ORGANISM: Artificial Sequence
<220> FEATURE:
<223> OTHER INFORMATION: Primer

<400> SEQUENCE: 54
ccgaaaacct gtattttcag ggcgccatg                                       29

<210> SEQ ID NO 55
<211> LENGTH: 29
<212> TYPE: DNA
<213> ORGANISM: Artificial Sequence
<220> FEATURE:
<223> OTHER INFORMATION: Primer

<400> SEQUENCE: 55
gcatcaacca tttagctacc actggatcc                                       29

<210> SEQ ID NO 56
<211> LENGTH: 51
<212> TYPE: DNA
<213> ORGANISM: Artificial Sequence
<220> FEATURE:
<223> OTHER INFORMATION: Primer

<400> SEQUENCE: 56
gtttaacttt aataaggaga tataccatgt cgtactacca tcaccatcac c              51

<210> SEQ ID NO 57
<211> LENGTH: 43
<212> TYPE: DNA
<213> ORGANISM: Artificial Sequence
<220> FEATURE:
<223> OTHER INFORMATION: Primer

<400> SEQUENCE: 57
ctttacggcc tgaaccacca atatgagcgt cacctttagt tgc                       43

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
ggtggttcag gccgtaaagg                                                 20

<210> SEQ ID NO 59
<211> LENGTH: 45
<212> TYPE: DNA

```
<213> ORGANISM: Artificial Sequence
<220> FEATURE:
<223> OTHER INFORMATION: Primer

<400> SEQUENCE: 59
ccttggggct cgagttatca tttgtacagt tcatccatac catgc              45

<210> SEQ ID NO 60
<211> LENGTH: 47
<212> TYPE: DNA
<213> ORGANISM: Artificial Sequence
<220> FEATURE:
<223> OTHER INFORMATION: Primer

<400> SEQUENCE: 60
catggtatat ctccttatta aagttaaaca aaattatttc tacaggg            47

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
tgataactcg agccccaagg                                          20

<210> SEQ ID NO 62
<211> LENGTH: 47
<212> TYPE: DNA
<213> ORGANISM: Artificial Sequence
<220> FEATURE:
<223> OTHER INFORMATION: Primer

<400> SEQUENCE: 62
catggtatat ctccttatta aagttaaaca aaattatttc tacaggg            47

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
tgataactcg agccccaagg                                          20

<210> SEQ ID NO 64
<211> LENGTH: 30
<212> TYPE: DNA
<213> ORGANISM: Artificial Sequence
<220> FEATURE:
<223> OTHER INFORMATION: Primer

<400> SEQUENCE: 64
ggtggttcag gccgtaaagg cgaagagctg                               30

<210> SEQ ID NO 65
<211> LENGTH: 60
<212> TYPE: DNA
<213> ORGANISM: Artificial Sequence
<220> FEATURE:
<223> OTHER INFORMATION: Primer

<400> SEQUENCE: 65
cgcgatttgc tggtgaccca atgcgaccag atgctccacg cccagtcgcg taccgtcctc    60
```

<210> SEQ ID NO 66
<211> LENGTH: 31
<212> TYPE: DNA
<213> ORGANISM: Artificial Sequence
<220> FEATURE:
<223> OTHER INFORMATION: Primer

<400> SEQUENCE: 66
gccctgaaaa tacaggtttt cggtcgttgg g                            31

<210> SEQ ID NO 67
<211> LENGTH: 60
<212> TYPE: DNA
<213> ORGANISM: Artificial Sequence
<220> FEATURE:
<223> OTHER INFORMATION: Primer

<400> SEQUENCE: 67
gaggacggta cgcgactggg cgtggagcat ctggtcgcat tgggtcacca gcaaatcgcg      60

<210> SEQ ID NO 68
<211> LENGTH: 60
<212> TYPE: DNA
<213> ORGANISM: Artificial Sequence
<220> FEATURE:
<223> OTHER INFORMATION: Primer

<400> SEQUENCE: 68
cgagctcggg ttcgggcggt agtggtgcca tggtaaccac cttatcaggt ttatcaggtg      60

<210> SEQ ID NO 69
<211> LENGTH: 60
<212> TYPE: DNA
<213> ORGANISM: Artificial Sequence
<220> FEATURE:
<223> OTHER INFORMATION: Primer

<400> SEQUENCE: 69
gtggtggtgc tcgagtgcgg ccgcaagctt ctattaagta tgagcgtcac ctttagttgc      60

<210> SEQ ID NO 70
<211> LENGTH: 28
<212> TYPE: DNA
<213> ORGANISM: Artificial Sequence
<220> FEATURE:
<223> OTHER INFORMATION: Primer

<400> SEQUENCE: 70
ggtttcgcca cctctgactt gagcgtcg                                28

<210> SEQ ID NO 71
<211> LENGTH: 32
<212> TYPE: DNA
<213> ORGANISM: Artificial Sequence
<220> FEATURE:
<223> OTHER INFORMATION: Primer

<400> SEQUENCE: 71
catggcacca ctaccgcccg aacccgagct cg                           32

<210> SEQ ID NO 72
<211> LENGTH: 50
<212> TYPE: DNA
<213> ORGANISM: Artificial Sequence
<220> FEATURE:

<223> OTHER INFORMATION: Primer

<400> SEQUENCE: 72
aagcttgcgg ccgcactcga gcaccaccac caccaccact gagatccggc    50

<210> SEQ ID NO 73
<211> LENGTH: 28
<212> TYPE: DNA
<213> ORGANISM: Artificial Sequence
<220> FEATURE:
<223> OTHER INFORMATION: Primer

<400> SEQUENCE: 73
cgacgctcaa gtcagaggtg gcgaaacc    28

<210> SEQ ID NO 74
<211> LENGTH: 60
<212> TYPE: DNA
<213> ORGANISM: Artificial Sequence
<220> FEATURE:
<223> OTHER INFORMATION: Primer

<400> SEQUENCE: 74
ggcagcattg aatttattaa agtgaacaaa ggcagtggtg agtcgggatc cggagctagc    60

<210> SEQ ID NO 75
<211> LENGTH: 80
<212> TYPE: DNA
<213> ORGANISM: Artificial Sequence
<220> FEATURE:
<223> OTHER INFORMATION: Primer

<400> SEQUENCE: 75
gtttattatt tatagcgttt gtaggcgtcc accataacaa tagtaggaac accggaacct    60
tccccggatc cctcgaggcc    80

<210> SEQ ID NO 76
<211> LENGTH: 59
<212> TYPE: DNA
<213> ORGANISM: Artificial Sequence
<220> FEATURE:
<223> OTHER INFORMATION: Primer

<400> SEQUENCE: 76
ggacgcctac aaacgctata ataataaac tctagcacca ctgagatccg gctgctaac    59

<210> SEQ ID NO 77
<211> LENGTH: 60
<212> TYPE: DNA
<213> ORGANISM: Artificial Sequence
<220> FEATURE:
<223> OTHER INFORMATION: Primer

<400> SEQUENCE: 77
actgcctttg ttcactttaa taaattcaat gctgcccagt ttccccatat ggctgccgcg    60

<210> SEQ ID NO 78
<211> LENGTH: 55
<212> TYPE: DNA
<213> ORGANISM: Artificial Sequence
<220> FEATURE:
<223> OTHER INFORMATION: Primer

<400> SEQUENCE: 78
tcgagggcgg cgcccacatc gtgatggtgg acgcctacaa gccgacgaag ggcgc    55

<210> SEQ ID NO 79
<211> LENGTH: 52
<212> TYPE: DNA
<213> ORGANISM: Artificial Sequence
<220> FEATURE:
<223> OTHER INFORMATION: Primer

<400> SEQUENCE: 79
ggccgccttc gtcggcttgt aggcgtccac catcacgatg tgggcgccgc cc    52

<210> SEQ ID NO 80
<211> LENGTH: 55
<212> TYPE: DNA
<213> ORGANISM: Artificial Sequence
<220> FEATURE:
<223> OTHER INFORMATION: Primer

<400> SEQUENCE: 80
tcgagggcgg cgcccacatc gtgatggtgg ccgcctacaa gccgacgaag ggcgc    55

<210> SEQ ID NO 81
<211> LENGTH: 51
<212> TYPE: DNA
<213> ORGANISM: Artificial Sequence
<220> FEATURE:
<223> OTHER INFORMATION: Primer

<400> SEQUENCE: 81
ggccgccttc gtcggcttgt agcggccacc atcacgatgt gggcgccgcc c    51

<210> SEQ ID NO 82
<211> LENGTH: 38
<212> TYPE: DNA
<213> ORGANISM: Artificial Sequence
<220> FEATURE:
<223> OTHER INFORMATION: Primer

<400> SEQUENCE: 82
taatctcgag atcagggcgc catggttgat accttatc    38

<210> SEQ ID NO 83
<211> LENGTH: 39
<212> TYPE: DNA
<213> ORGANISM: Artificial Sequence
<220> FEATURE:
<223> OTHER INFORMATION: Primer

<400> SEQUENCE: 83
atatgcggcc gctccactcc cctggaagta gaggttttc    39

<210> SEQ ID NO 84
<211> LENGTH: 68
<212> TYPE: DNA
<213> ORGANISM: Artificial Sequence
<220> FEATURE:
<223> OTHER INFORMATION: Primer

<400> SEQUENCE: 84
gcgtttagcg catcggcggg cagctaccca tacgatgttc cagattacgc tggtgcagct    60
gcaggtcg    68

<210> SEQ ID NO 85
<211> LENGTH: 79
<212> TYPE: DNA

<213> ORGANISM: Artificial Sequence
<220> FEATURE:
<223> OTHER INFORMATION: Primer

<400> SEQUENCE: 85
cgccgatgcg ctaaacgcta aaactaaacc agccagcgcc agccaaatct ttttcatagc    60
tgtttcctgt gtgaaattg                                                 79

<210> SEQ ID NO 86
<211> LENGTH: 17
<212> TYPE: DNA
<213> ORGANISM: Artificial Sequence
<220> FEATURE:
<223> OTHER INFORMATION: Primer

<400> SEQUENCE: 86
ggtgcagctg caggtcg                                                   17

<210> SEQ ID NO 87
<211> LENGTH: 28
<212> TYPE: DNA
<213> ORGANISM: Artificial Sequence
<220> FEATURE:
<223> OTHER INFORMATION: Primer

<400> SEQUENCE: 87
tttcatagct gtttcctgtg tgaaattg                                       28

<210> SEQ ID NO 88
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (13)..(13)
<223> OTHER INFORMATION: k is g or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (16)..(16)
<223> OTHER INFORMATION: k is g or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(19)
<223> OTHER INFORMATION: k is g or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: k is g or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature

```
<222> LOCATION: (25)..(25)
<223> OTHER INFORMATION: k is g or t

<400> SEQUENCE: 88
acctcgagat nnknnknnkn nknnkatcgt gatggtggac gcctacaagc c         51

<210> SEQ ID NO 89
<211> LENGTH: 35
<212> TYPE: DNA
<213> ORGANISM: Artificial Sequence
<220> FEATURE:
<223> OTHER INFORMATION: Primer

<400> SEQUENCE: 89
attcatatgg tttaccagcg ccaaagacaa aaggg                           35

<210> SEQ ID NO 90
<211> LENGTH: 80
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (39)..(39)
<223> OTHER INFORMATION: k is g or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: k is g or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: k is g or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (51)..(51)
<223> OTHER INFORMATION: k is g or t

<400> SEQUENCE: 90
cgacctcgag atgtgcctac tatcgtgatg gtggacnnkn nknnknnknn kgcggccgca    60
ggctctaaag atatcagacc                                               80

<210> SEQ ID NO 91
<211> LENGTH: 25
<212> TYPE: DNA
<213> ORGANISM: Artificial Sequence
<220> FEATURE:
```

<223> OTHER INFORMATION: Primer

<400> SEQUENCE: 91
gatcgttgtc agaagtaagt tggcc                                   25

<210> SEQ ID NO 92
<211> LENGTH: 25
<212> TYPE: DNA
<213> ORGANISM: Artificial Sequence
<220> FEATURE:
<223> OTHER INFORMATION: Primer

<400> SEQUENCE: 92
ggccaactta cttctgacaa cgatc                                   25

<210> SEQ ID NO 93
<211> LENGTH: 42
<212> TYPE: DNA
<213> ORGANISM: Artificial Sequence
<220> FEATURE:
<223> OTHER INFORMATION: Primer

<400> SEQUENCE: 93
gtccaccatc acgatagtag gcacatctcg aggtcgacct gc                42

<210> SEQ ID NO 94
<211> LENGTH: 22
<212> TYPE: DNA
<213> ORGANISM: Artificial Sequence
<220> FEATURE:
<223> OTHER INFORMATION: Primer

<400> SEQUENCE: 94
ggatccagtg gtagcgaaaa cc                                      22

<210> SEQ ID NO 95
<211> LENGTH: 21
<212> TYPE: DNA
<213> ORGANISM: Artificial Sequence
<220> FEATURE:
<223> OTHER INFORMATION: Primer

<400> SEQUENCE: 95
aaccatggcg ccctgatctc g                                       21

<210> SEQ ID NO 96
<211> LENGTH: 22
<212> TYPE: DNA
<213> ORGANISM: Artificial Sequence
<220> FEATURE:
<223> OTHER INFORMATION: Primer

<400> SEQUENCE: 96
cctcgagatc agggcgccat gg                                      22

<210> SEQ ID NO 97
<211> LENGTH: 29
<212> TYPE: DNA
<213> ORGANISM: Artificial Sequence
<220> FEATURE:
<223> OTHER INFORMATION: Primer

<400> SEQUENCE: 97
gaagtagagg ttttcgctac cactggatc                               29

```
<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
gtctgacctg cctcaacctc                                               20

<210> SEQ ID NO 99
<211> LENGTH: 19
<212> TYPE: DNA
<213> ORGANISM: Artificial Sequence
<220> FEATURE:
<223> OTHER INFORMATION: Primer

<400> SEQUENCE: 99
tcaccggaac cagagccac                                                19

<210> SEQ ID NO 100
<211> LENGTH: 16
<212> TYPE: PRT
<213> ORGANISM: Artificial Sequence
<220> FEATURE:
<223> OTHER INFORMATION: SpyTag002 containing peptide

<400> SEQUENCE: 100

Lys Gly Val Pro Thr Ile Val Met Val Asp Ala Tyr Lys Arg Tyr Lys
1               5                   10                  15

<210> SEQ ID NO 101
<211> LENGTH: 83
<212> TYPE: PRT
<213> ORGANISM: Artificial Sequence
<220> FEATURE:
<223> OTHER INFORMATION: Truncated SpyCatcher002 variant

<400> SEQUENCE: 101

Asp Ser Ala Thr His Ile Lys Phe Ser Lys Arg Asp Glu Asp Gly Arg
1               5                   10                  15

Glu Leu Ala Gly Ala Thr Met Glu Leu Arg Asp Ser Ser Gly Lys Thr
            20                  25                  30

Ile Ser Thr Trp Ile Ser Asp Gly His Val Lys Asp Phe Tyr Leu Tyr
        35                  40                  45

Pro Gly Lys Tyr Thr Phe Val Glu Thr Ala Ala Pro Asp Gly Tyr Glu
    50                  55                  60

Val Ala Thr Pro Ile Thr Phe Thr Val Asn Glu Asp Gly Gln Val Thr
65                  70                  75                  80

Val Asn Gly
```

PROTEINS AND PEPTIDE TAGS WITH ENHANCED RATE OF SPONTANEOUS ISOPEPTIDE BOND FORMATION AND USES THEREOF

CROSS-REFERENCE TO RELATED APPLICATIONS

This application is a continuation of U.S. patent application Ser. No. 16/606,818, filed Oct. 21, 2019, now U.S. Pat. No. 11,059,867, issued Jul. 13, 2021, which is the National Stage of International Application No. PCT/GB2018/051065, filed Apr. 24, 2018, which claims the benefit of and priority to GB 1706430.4, filed Apr. 24, 2017, which are entirely incorporated herein by reference.

SEQUENCE LISTING

This application contains a sequence listing filed in electronic form as an ASCII.txt file entitled "131607-01 2018-04-24—Seq listing_ST25.txt", created on Sep. 16, 2021 and having a size of 36 kb. The content of the sequence listing is incorporated herein in its entirety.

DISCUSSION

The present invention relates to a two-part linker comprising a peptide tag and a polypeptide (protein) that is capable of spontaneously forming an isopeptide bond. In particular, the two-part linker of invention may be viewed as a peptide tag and polypeptide binding partner cognate pair that can be conjugated via a covalent bond when contacted under conditions that allow the spontaneous formation of an isopeptide bond between the peptide tag and its polypeptide binding partner. Nucleic acid molecules encoding said each part of said two-part linker (i.e. peptide tag and polypeptide binding partner), vectors comprising said nucleic acid molecules, and host cells comprising said vectors and nucleic acid molecules are also provided. A kit comprising said two-part linker (i.e. peptide tag and polypeptide binding partner), and/or nucleic acid molecules/vectors is also provided. A method of producing said two-part linker (i.e. peptide tag and polypeptide binding partner) and the uses of the two-part linker of the invention are also provided.

Cellular function depends on enormous numbers of reversible non-covalent protein-protein interactions and the precise arrangement of proteins in complexes influences and determines their function. Thus, the ability to engineer covalent protein-protein interactions can bring a range of new opportunities for basic research, synthetic biology and biotechnology. In particular, the conjugation of two or more proteins to form a so-called "fusion protein" can result in molecules with useful characteristics. For instance, clustering a single kind of protein often greatly enhances biological signals, e.g. the repeating antigen structures on vaccines. Clustering proteins with different activities can also result in complexes with improved activities, e.g. substrate channeling by enzymes.

Typically covalent protein interactions are mediated through disulfide bonds, but disulfides are reversible, inapplicable in reducing cellular compartments, and can interfere with protein folding. Peptide tags are convenient tools for protein analysis and modification because their small size minimises the perturbation to protein function. Peptide tags are simple to genetically encode and their small size reduces disruption from interfering with other interactions, cost of biosynthesis and introduction of immunogenicity. However, interactions between peptide tags and their peptide or polypeptide binding partners are rarely of high affinity, which limits their utility in the formation of stable complexes.

Proteins that are capable of spontaneous isopeptide bond formation (so-called "isopeptide proteins") have been advantageously used to develop peptide tag/polypeptide binding partner pairs (i.e. two-part linkers) which covalently bind to each other and provide irreversible interactions (see e.g. WO2011/098772 and WO 2016/193746 both herein incorporated by reference). In this respect, proteins which are capable of spontaneous isopeptide bond formation may be expressed as separate fragments, to give a peptide tag and a polypeptide binding partner for the peptide tag, where the two fragments are capable of covalently reconstituting by isopeptide bond formation, thereby linking molecules or components fused to the peptide tag and its polypeptide binding partner. The isopeptide bond formed by the peptide tag and its polypeptide binding partner is stable under conditions where non-covalent interactions would rapidly dissociate, e.g. over long periods of time (e.g. weeks), at high temperature (to at least 95° C.), at high force, or with harsh chemical treatment (e.g. pH 2-11, organic solvent, detergents or denaturants).

Isopeptide bonds are amide bonds formed between carboxyl/carboxamide and amino groups, where at least one of the carboxyl or amino groups is outside of the protein main-chain (the backbone of the protein). Such bonds are chemically irreversible under typical biological conditions and they are resistant to most proteases. As isopeptide bonds are covalent in nature, they result in the some of the strongest measured protein interactions.

In brief, a two-part linker, i.e. a peptide tag and its polypeptide binding partner (a so-called peptide tag/binding partner pair) may be derived from a protein capable of spontaneously forming an isopeptide bond (an isopeptide protein), wherein the domains of the protein are expressed separately to produce a peptide tag that comprises one of the residues involved in the isopeptide bond (e.g. an aspartate or asparagine) and a peptide or polypeptide binding partner (or "catcher") that comprises the other residue involved in the isopeptide bond (e.g. a lysine) and at least one other residue required to form the isopeptide bond (e.g. a glutamate). Mixing the peptide tag and binding partner results in the spontaneous formation of an isopeptide bond between the tag and binding partner. Thus, by separately fusing the peptide tag and binding partner to different molecules or components, e.g. proteins, it is possible to covalently link said molecules or components together via an isopeptide bond formed between the peptide tag and binding partner, i.e. to form a linker between the molecules or components fused to the peptide tag and binding partner.

A peptide tag/binding partner pair (two-part linker), termed SpyTag/SpyCatcher, has been derived from the CnaB2 domain of the *Streptococcus pyogenes* FbaB protein (Zakeri et al., 2012, Proc Natl Acad Sci USA 109, E690-697) and used in diverse applications, including biomaterials (Botyanszki et al., 2015, Biotechnology and bioengineering 112, 2016-2024; Chen et al., 2014, Proc Natl Acad Sci USA 108, 11399-11404), next generation sequencing (Stranges et al., 2016, Proc Natl Acad Sci USA 113, E6749-E6756), enzyme stabilization (Schoene et al., 2016, Scientific reports 6, 21151) and vaccine development (Brune et al., 2016, Scientific reports 6, 19234; Thrane et al., 2016, Journal of nanobiotechnology 14, 30). However, whilst the speed of the formation of the isopeptide bond between SpyTag and SpyCatcher is satisfactory with purified components, the speed is limiting at cellular expression levels.

Accordingly, there is a desire to develop linkers, e.g. peptide tag ("tag") and polypeptide binding partner ("catcher") pairs with the advantageous properties associated with tag/catcher systems derived from isopeptide proteins, i.e. a peptide tag and polypeptide binding partner, that form a stable and robust covalent bond as discussed above, with reaction rates that are sufficiently high to enable efficient reaction at low concentrations, particularly at cellular expression levels.

The present inventors have surprisingly determined that the reaction rate of the SpyTag and SpyCatcher peptides can be increased significantly by modifying (i.e. mutating) the amino acid sequences of the SpyTag peptide and SpyCatcher polypeptide (SEQ ID NOs: 6 and 7, respectively). As discussed in detail in the Examples, a number of steps were required to determine if the reaction rate of SpyTag and SpyCatcher could be improved and, if so, which modifications of the SpyTag peptide and SpyCatcher polypeptide would increase the reaction rate without adversely affecting other desirable properties of the peptide tag and binding partner pair.

Firstly, the inventors had to identify the parameters of the screen that could successfully identify modifications that improve the activity of SpyTag and SpyCatcher, i.e. the extent to which residues in the SpyTag peptide (SEQ ID NO: 6) and SpyCatcher polypeptide (SEQ ID NO: 7) could be modified without substantially reducing the reaction rate. It was hypothesised that the activity of the SpyTag peptide is predominantly determined by a few "anchor" residues. As mutation of the anchor residues is likely to mask the effects of mutations at other positions that have only a moderately positive effect on reaction rate it was postulated that generating a mutant library of peptide tags in which mutations are permitted anywhere in the sequence actually reduces the possibility of identifying peptides with improved activity. Thus, the inventors selected the two N-terminal residues of SpyTag and six C-terminal residues of SpyTag for modification and determined that the addition of residues at the N- and/or C-terminus was permissible. A library of randomly mutated SpyCatcher polypeptides was developed for use in the screening method. In this respect, it is difficult to design mutations based on the crystal structure of SpyCatcher because not all of the residues are visible in the crystal structure.

Secondly, the inventors determined that the N-terminal and C-terminal SpyTag mutants should be screened separately and designed a suitable screening process to identify mutant SpyTag peptides and SpyCatcher polypeptides with improved activity. Accordingly, two subsets of libraries with mutations at either the N- or C-terminus of SpyTag were produced and screened for improved activity in a phage display system using SpyCatcher as bait. A separate screen was performed using a library of SpyCatcher mutants using SpyTag as bait.

The design of the selection parameters in the phage display system was not straightforward. In this respect, it was hypothesised that the rate at which the SpyTag peptide and SpyCatcher polypeptide interact may be limiting on the reaction rate. Accordingly, the development of a suitable screening system required the selection of reaction conditions at which the rate of reaction between the SpyTag peptide and SpyCatcher polypeptide is not optimal. The use of reaction conditions (e.g. pH, temperature etc.) at which the rate of reaction between SpyTag and SpyCatcher is fastest would hinder the detection of differences in the reactivity of the mutant peptides and polypeptides relative to SpyTag and SpyCatcher, respectively.

A further key to the identification of mutant peptides and polypeptides arose from the design of the conditions used to separate unreacted mutant tag-catcher complexes associated via non-covalent bonds from complexes linked by an isopeptide bond. As discussed in the Examples, a combination of low pH buffer and protease treatment was used to separate non-covalent and covalent complexes thereby ensuring that only mutant peptides and polypeptides capable of spontaneously forming an isopeptide bond with their respective partner were selected for analysis and further modification.

In this respect, the development of the mutant "tag" and "catcher" with improved reaction rates relative to SpyTag and SpyCatcher required the design and introduction of various additional modifications (i.e. mutations) to the mutant peptides and polypeptides identified from the screening process. Not only did the modifications result in mutant "tag" peptides and "catcher" polypeptides with improved reaction rates when reacted with their unmutated partners (e.g. >6-fold increase for the mutated tag reacted with unmutated SpyCatcher and >3-fold increase for the mutated catcher reacted with unmutated SpyTag), but it was surprisingly determined that the effect of the mutations on the reaction rate of the mutant "tag" and "catcher" is cumulative when used together (i.e. a mutant tag and catcher pair show a >10-fold increase in speed of reaction relative to reaction of the SpyTag and SpyCatcher pair). Thus, advantageously, the mutant tag and catcher of the invention (i.e. the two-part linker) are particularly useful at low concentrations. As discussed further below, the improved rate constant of the mutant tag and catcher of the invention is also advantageous in reactions in which the tag and/or catcher are fused to molecules or components that may slow the reaction (e.g. large proteins) and in reactions where molecules or components fused to the mutant tag and/or catcher of the invention cause steric hindrance. Moreover, the modifications required to improve the speed of reaction do not affect the other useful properties associated with SpyTag and SpyCatcher, i.e. thermal stability, reaction over a range of pH values and temperatures and in a wide range of buffers, including in the presence of detergent, and efficient expression in *Escherichia coli*.

Thus, in one aspect, the present invention therefore provides a peptide, i.e. a peptide tag, comprising an amino acid sequence as set forth in SEQ ID NO: 1, wherein:
(i) X at position 1 is arginine or no amino acid;
(ii) X at position 2 is glycine or no amino acid;
(iii) X at position 5 is threonine or histidine, preferably histidine;
(iv) X at position 11 is alanine, glycine or valine, preferably alanine; and
(v) X at position 14 is arginine or lysine, preferably arginine,
wherein when X at position 1 is no amino acid, X at position 2 is no amino acid,
and wherein said peptide (peptide tag) is capable of spontaneously forming an isopeptide bond with a polypeptide (i.e. a polypeptide binding partner) comprising an amino acid sequence as set forth in SEQ ID NO: 2, wherein said isopeptide bond forms between the aspartic acid residue at position 10 of SEQ ID NO: 1 and the lysine residue at position 34 of SEQ ID NO: 2.

Thus, the peptide tag of the invention comprises at least four (e.g. five or six) modifications (e.g. additions and substitutions) relative to the original SpyTag peptide.

As discussed in the Examples below, the lead mutant peptide tag (SpyTag variant peptide) identified in the N-terminal screen contained three N-terminal amino acids relative to SpyTag and it was determined that two of these residues could be removed without significantly affecting the reaction rate of the peptide. Thus, in some embodiments, the peptide tag of the invention does not contain amino acids at positions 1 and 2 of SEQ ID NO: 1, i.e. when X at position 1 is no amino acid, X at position 2 is no amino acid and when at position 2 is no amino acid, X at position 1 is no amino acid. Alternatively viewed, in some embodiments, the peptide tag comprises or consists of an amino acid sequence as set forth in SEQ ID NO: 8, wherein:
- (i) X at position 3 is threonine or histidine, preferably histidine;
- (ii) X at position 9 is alanine, glycine or valine, preferably alanine; and
- (iii) X at position 12 is arginine or lysine, preferably arginine.

However, the inventors have determined that the inclusion of arginine and glycine residues at the N-terminus further improves the reaction rate of the SpyTag variant. Accordingly, in preferred embodiments, the peptide tag of the invention comprises an amino acid sequence as set forth in SEQ ID NO: 1, wherein:
- (i) X at position 1 is arginine;
- (ii) X at position 2 is glycine;
- (iii) X at position 5 is threonine or histidine, preferably histidine;
- (iv) X at position 11 is alanine, glycine or valine, preferably alanine; and
- (v) X at position 14 is arginine or lysine, preferably arginine.

Alternatively viewed, in some embodiments, the peptide tag comprises or consists of an amino acid sequence as set forth in SEQ ID NO: 9, wherein:
- (i) X at position 5 is threonine or histidine, preferably histidine;
- (ii) X at position 11 is alanine, glycine or valine, preferably alanine; and
- (iii) X at position 14 is arginine or lysine, preferably arginine.

It is contemplated that conservative substitutions at positions 11 and 14 of SEQ ID NOs: 1 and 9 (equivalent to positions 9 and 12 of SEQ ID NO: 8) may be tolerated without significantly affecting the activity of the peptide tag. Nevertheless, in some embodiments, it is preferred that position 11 of SEQ ID NOs: 1 and 9 (equivalent to position 9 of SEQ ID NO: 8) is alanine and/or position 14 of SEQ ID NOs: 1 and 9 (equivalent to position 12 of SEQ ID NO: 8) is arginine.

The lead mutant peptide tag (SpyTag variant peptide) identified in the N-terminal screen described in the Examples contained a valine residue at position 3 and a threonine residue at position 5 (using the numbering of SEQ ID NO: 1), which corresponds to positions −1 and 2 in SpyTag (SEQ ID NO: 6), respectively. Whilst it was hypothesised that each amino acid mutation identified from the screening process contributed to the improved activity of the SpyTag variant peptide, the inventors interrogated the non-conservative mutations in the SpyTag variant peptide. In this respect, the valine residue at position 3 of SEQ ID NO: 1 represents a non-conservative mutation relative to the aspartic acid residue at the equivalent position in the CnaB2 domain of the *Streptococcus pyogenes* FbaB protein from which SpyTag is derived. Moreover, the threonine residue at position 5 of SEQ ID NO: 1 represents a non-conservative substitution relative to the histidine residue at the equivalent position in SpyTag. Surprisingly, the inventors determined that the valine residue is essential for the improved activity of the SpyTag variant as its deletion dramatically reduced activity. Furthermore, substitution of the threonine residue with histidine at position 5 of SEQ ID NO: 1 (i.e. reversion to the SpyTag sequence) unexpectedly improved activity.

Accordingly, in preferred embodiments, the peptide tag of the invention comprises an amino acid sequence as set forth in SEQ ID NO: 1, wherein:
- (i) X at position 1 is arginine;
- (ii) X at position 2 is glycine;
- (iii) X at position 5 is histidine;
- (iv) X at position 11 is alanine, glycine or valine, preferably alanine; and
- (v) X at position 14 is arginine or lysine, preferably arginine.

Alternatively viewed, in some embodiments, the peptide tag of the invention comprises an amino acid sequence as set forth in SEQ ID NO: 10, wherein:
- (i) X at position 11 is alanine, glycine or valine, preferably alanine; and
- (ii) X at position 14 is arginine or lysine, preferably arginine.

Thus, in some embodiments, the peptide tag of the invention comprises an amino acid sequence as set forth in SEQ ID NO: 3, 4 or 5, preferably SEQ ID NO: 4 or 5, most preferably SEQ ID NO: 5.

As discussed above, the phage display screen identified a variant (i.e. mutant) polypeptide (a peptide tag binding partner or catcher) with improved activity relative to SpyCatcher. It is contemplated that each substitution in the polypeptide (peptide tag binding partner) of the invention (SEQ ID NO: 2, i.e. SpyCatcher polypeptide variant) relative to the amino acid sequence of SpyCatcher (SEQ ID NO: 7) may separately improve the activity of the polypeptide (peptide tag binding partner).

Furthermore, in view of the fact that the SpyCatcher polypeptide can be truncated at its N-terminus and C-terminus without significantly affecting its activity (Li et al., 2014, J Mol Biol.; 426(2): 309-317) it is contemplated that the polypeptide exemplified herein (i.e. SEQ ID NO: 2) may be truncated at the N-terminus and/or C-terminus without significantly reducing the activity of the polypeptide. In particular, the SEQ ID NO: 2 may be truncated by up to 24 amino acids at the N-terminus (e.g. 5, 10, 15 or 20 amino acids) and/or by up to 9 amino acids at the C-terminus (e.g. 1, 2, 3, 4, 5, 6, 7, 8 or 9 amino acids).

Thus, in another aspect, the invention provides a polypeptide (peptide tag binding partner) comprising:
- i) an amino acid sequence as set forth in SEQ ID NO: 2;
- ii) a portion of (i) comprising an amino acid sequence as set forth in SEQ ID NO: 101;
- iii) an amino acid sequence with at least 80% sequence identity to a sequence as set forth in SEQ ID NO: 2, wherein said amino acid sequence comprises a lysine at position 34, glutamic acid at position 80 and one or more of the following:
  1) threonine at position 5;
  2) proline at position 16;
  3) arginine at position 40;
  4) histidine at position 65;
  5) proline at position 92;
  6) aspartic acid at position 100:
  7) glutamic acid at position 108; and
  8) threonine at position 116 wherein the specified amino acid residues are at positions equivalent to the positions in SEQ ID NO: 2 and; or
- iv) a portion of (iii) comprising an amino acid sequence with at least 80% sequence identity to a sequence as set forth in SEQ ID NO: 101 (e.g. at least 85, 90, 95, 96, 97, 98 or 99% identical to a sequence as set forth in SEQ ID NO: 101), wherein the amino acid sequence comprises a lysine at position 10 (or a position equivalent to position 34 in SEQ ID NO: 2), a glutamic acid at position 56 (or a position equivalent to position 80 in SEQ ID NO: 2) and one or more of the following:
1) arginine at position 16 (or a position equivalent to position 40 in SEQ ID NO: 2);
2) histidine at position 41 (or a position equivalent to position 65 in SEQ ID NO: 2);
3) proline at position 68 (or a position equivalent to position 92 in SEQ ID NO: 2); and
4) aspartic acid at position 76 (or a position equivalent to position 100 in SEQ ID NO: 2),
wherein the specified amino acid residues are at positions equivalent to the positions in SEQ ID NO: 101 (or SEQ ID NO: 2),
and wherein said polypeptide is capable of spontaneously forming an isopeptide bond with a peptide (peptide tag) comprising an amino acid sequence as set forth in SEQ ID NO: 5, wherein said isopeptide bond forms between the aspartic acid residue at position 10 of SEQ ID NO: 5 and the lysine residue at position 34 of SEQ ID NO: 2 or position 10 of SEQ ID NO: 101.

In embodiments in which the polypeptide (peptide tag binding partner) variants (i.e. sequence identity related polypeptides and portions thereof) of the invention do not contain all of the residues specified above, it is preferred that, with the exception of position 5 (discussed below), in the specified positions the variants contain the amino acid residues at the equivalent positions in the SpyCatcher peptide (SEQ ID NO: 7). The equivalent positions can readily be determined by comparing the amino acid sequence of the polypeptide (peptide tag binding partner) variant with SEQ ID NO: 7, e.g. using the BLASTP algorithm.

Thus, by way of example, in embodiments where the polypeptide (peptide tag binding partner) of the invention comprises an amino acid sequence with at least 80% sequence identity to a sequence as set forth in SEQ ID NO: 2, if the residue at position 16 (or the equivalent position) is not proline, it is preferred that the residue is glutamine. Similarly, if the residue at position 40 (or the equivalent position) is not arginine, it is preferred that the residue is lysine. If the residue at position 65 (or the equivalent position) is not histidine, it is preferred that the residue is glutamine. If the residue at position 92 (or the equivalent position) is not proline, it is preferred that the residue is alanine. If the residue at position 100 (or the equivalent position) is not aspartic acid, it is preferred that the residue is glutamine. If the residue at position 108 (or the equivalent position) is not glutamic acid, it is preferred that the residue is lysine. If the residue at position 116 (or the equivalent position) is not threonine, it is preferred that the residue is isoleucine.

In some embodiments, a polypeptide (peptide tag binding partner) variant of the present invention may differ from SEQ ID NO: 2 by, for example, 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, e.g. 1, 2 or 3 amino acid substitutions, insertions and/or deletions, preferably 1 to 23, 1 to 20, 1 to 15, 1 to 10, 1 to 8, 1 to 6, 1 to 5, 1 to 4, e.g. 1, 2 to 3 amino acid substitutions and/or 1 to 33, 1 to 30, 1 to 25, 1 to 20, 1 to 15, 1 to 10, 1 to 8, 1 to 6, 1 to 5, 1 to 4, e.g. 1, 2 or 3 amino acid deletions. As discussed below, in some embodiments, it is preferred that deletions are at the N- and/or C-terminus, i.e. truncations, thereby generating polypeptide portions of SEQ ID NO: 2 as defined above.

In some embodiments, any mutations that are present in the polypeptide (peptide tag binding partner) of the present invention relative to the exemplified polypeptide (SEQ ID NO: 2) may be conservative amino acid substitutions. A conservative amino acid substitution refers to the replacement of an amino acid by another which preserves the physicochemical character of the polypeptide (e.g. D may be replaced by E or vice versa, N by Q, or L or I by V or vice versa). Thus, generally the substituting amino acid has similar properties, e.g. hydrophobicity, hydrophilicity, electronegativity, bulky side chains etc. to the amino acid being replaced. Isomers of the native L-amino acid e.g. D-amino acids may be incorporated.

Thus, in some embodiments in which the polypeptide (peptide tag binding partner) variants of the invention do not contain all of the residues specified above (i.e. all of the mutations in SEQ ID NO: 2 relative to SEQ ID NO: 7), with the exception of position 5, in the specified positions the variant may contain a conservative substitution of the amino acid residues at the equivalent positions in the SpyCatcher peptide (SEQ ID NO: 7). Thus, for example, if the residue at position 16 (or the equivalent position) is not proline or glutamine it is preferred that the residue is asparagine.

Accordingly, in some embodiments, the polypeptide (peptide tag binding partner) of the invention may comprise an amino acid sequence with at least 80% sequence identity to a sequence as set forth in SEQ ID NO: 2, wherein said amino acid sequence comprises a lysine at position 34, a glutamic acid at position 80 and any two, three, four, five, six, seven or eight of the following:
1) threonine at position 5;
2) proline at position 16;
3) arginine at position 40;
4) histidine at position 65;
5) proline at position 92;
6) aspartic acid at position 100:
7) glutamic acid at position 108; and
8) threonine at position 116,
wherein the specified amino acid residues are at positions equivalent to the positions in SEQ ID NO: 2.

As discussed in the Examples below, the inventors have unexpectedly determined that the presence of an aspartic acid residue at position 5 (based on the numbering of SEQ ID NO: 2 and SEQ ID NO: 7) of the polypeptide (peptide tag binding partner) mutants (i.e. variants) identified in the phage display screen results in the formation of an unwanted side-reaction—a polypeptide (peptide tag binding partner) dimer wherein the polypeptides are conjugated via an isopeptide bond. Mutation of the aspartic acid residue at position 5 to threonine or alanine was shown to eliminate the unwanted side-reaction and further improved the rate of the polypeptide (peptide tag binding partner) activity. Thus, in some embodiments, the polypeptide (peptide tag binding partner) of the invention may comprise an amino acid sequence with at least 80% sequence identity to a sequence as set forth in SEQ ID NO: 2, wherein said amino acid sequence comprises a threonine at position 5, a lysine at position 34, a glutamic acid at position 80 and one or more of the following:
1) proline at position 16;
2) arginine at position 40;
3) histidine at position 65;
4) proline at position 92;
5) aspartic acid at position 100:
6) glutamic acid at position 108; and
7) threonine at position 116, wherein the specified amino acid residues are at positions equivalent to the positions in SEQ ID NO: 2.

It is contemplated that the polypeptide (peptide tag binding partner) of the invention may comprise any one or any combination of the specified amino acid residues defined above (e.g. any combination of two, three, four, five, six or seven of the amino acid residues specified above), e.g. 1) and 2), 1) and 3), 1 and 4), 1) and 5), 1) and 6), 1) and 7), 1) and 8), 2) and 3), 2) and 4) etc., 1), 2) and 3), 1), 3) and 4), 1), 3) and 5) etc. However, some particularly preferred combinations include:

a) 1) threonine at position 5;
2) proline at position 16;
3) lysine at position 34;
4) arginine at position 40;
5) histidine at position 65;
6) glutamic acid at position 80;
7) glutamic acid at position 108; and
8) threonine at position 116;
b) 1) threonine at position 5;
2) proline at position 16;
3) lysine at position 34;
4) arginine at position 40;
5) histidine at position 65;
6) glutamic acid at position 80;
7) proline at position 92;
8) glutamic acid at position 108; and
9) threonine at position 116; and
c) 1) threonine at position 5;
2) proline at position 16;
3) lysine at position 34;
4) arginine at position 40;
5) histidine at position 65;
6) glutamic acid at position 80;
7) proline at position 92;
8) aspartic acid at position 100:
9) glutamic acid at position 108; and
10) threonine at position 116, wherein the specified amino acid residues are at positions equivalent to the positions in SEQ ID NO: 2.

In some further embodiments, the polypeptide (peptide tag binding partner) variants defined above may also comprise a glycine at position 12 and/or a threonine at position 22.

Thus, the polypeptide (peptide tag binding partner) of the present invention particularly may be at least 80% identical to the exemplified sequence as set forth in SEQ ID NO: 2 and more particularly is at least 85, 90, 95, 96, 97, 98 or 99% identical to SEQ ID NO: 2, wherein the polypeptide variant comprises a lysine at position 34 (or an equivalent position), a glutamic acid at position 80 (or an equivalent position) and one or more of the following:

1) threonine at position 5;
2) proline at position 16;
3) arginine at position 40;
4) histidine at position 65;
5) proline at position 92;
6) aspartic acid at position 100:
7) glutamic acid at position 108; and
8) threonine at position 116, wherein the specified amino acid residues are at positions equivalent to the positions in SEQ ID NO: 2.

The term "linker" as used herein refers to molecules that function to link, i.e. conjugate or join, two molecules or components together, preferably by a covalent bond, e.g. an isopeptide bond. Thus, the peptide tag and polypeptide of the invention may be viewed as a two-part linker, wherein formation of the isopeptide bond between the first part, i.e. peptide tag, and second part, i.e. polypeptide, reconstitutes the linker, thereby joining molecules or components fused or conjugated to said first and second parts of the linker. Alternatively stated, the peptide tag and polypeptide of the invention may be viewed as a cognate pair that functions as a linker, i.e. a peptide tag and polypeptide cognate pair or a peptide tag and binding partner cognate pair. These terms are used interchangeably throughout the description.

The term "cognate" refers to components that function together. Thus, in the context of the present invention, a cognate pair refers to a peptide tag and polypeptide of the invention that react together spontaneously to form an isopeptide bond. Thus, a two-part linker comprising a peptide tag and polypeptide that react together efficiently to form an isopeptide bond under conditions that enable the spontaneous formation of said isopeptide bond can also be referred to as being a "complementary pair", i.e. a peptide tag and polypeptide complementary pair.

Thus, the invention further provides a two-part linker comprising a peptide (peptide tag) and polypeptide (a peptide tag binding partner), wherein:

a) said peptide (peptide tag) comprises an amino acid sequence as defined above; and
b) said polypeptide (peptide tag binding partner) comprises an amino acid sequence as defined above, and wherein said peptide (peptide tag) and polypeptide (peptide tag binding partner) are capable of spontaneously forming an isopeptide bond between the aspartic acid residue at position 10 of SEQ ID NO: 1 and the lysine residue at position 34 of SEQ ID NO: 2.

The peptide tag and polypeptide (peptide tag binding partner) of the invention spontaneously form an isopeptide bond between the aspartic acid residue at position 10 of SEQ ID NO: 1 and the lysine residue at position 34 of SEQ ID NO: 2 under various conditions including those explained below that are suitable for the formation of an isopeptide bond between said peptide tag and polypeptide (peptide tag binding partner). It is evident from the Examples below that the peptide tag and polypeptide (peptide tag binding partner) of the invention are active under a range of conditions.

For instance, the peptide tag and polypeptide (peptide tag binding partner) are active in a variety of buffers including phosphate buffered saline (PBS), 4-(2-hydroxyethyl)-1-piperazineethanesulfonic acid (HEPES), HEPES buffered saline (HBS), and Tris buffered saline (TBS), both with and without EDTA. The peptide tag and polypeptide (peptide tag binding partner) are active at a pH of about 3.0-8.0, e.g. 4.0-7.0, 5.0-7.0, such as about 5.5-6.5, over a wide range of temperatures, e.g. 0-40° C., e.g. 1, 2, 3, 4, 5, 10, 12, 15, 18, 20, 22, 25, 28, 30, 35 or 37° C., preferably about 25-35° C., e.g. about 25° C. The peptide tag and polypeptide (peptide tag binding partner) of the invention are also active in the presence of the commonly used detergents, such as Tween 20 and Triton X-100, e.g. up to a concentration of about 1% (v/v), and in the presence of urea, e.g. up to a concentration of about 3M. The skilled person would readily be able to determine other suitable conditions.

Thus, in some embodiments, conditions that are suitable for the formation of an isopeptide bond between said peptide tag and polypeptide (peptide tag binding partner) of the invention includes any conditions in which contacting the peptide tag and polypeptide (peptide tag binding partner) of the invention results in the spontaneous formation of an isopeptide bond between said peptide tag and polypeptide (peptide tag binding partner), particularly between the aspartic acid residue at position 10 of SEQ ID NO: 1 (or equivalent position) and the lysine residue at position 34 of SEQ ID NO: 2 (or equivalent position). For instance, contacting said peptide tag and polypeptide (peptide tag binding partner) in buffered conditions, e.g. in a buffered solution or on a solid phase (e.g. column) that has been equilibrated with a buffer, such as PBS. The step of contacting may be at any suitable pH, such as pH 3.0-8.0, e.g. 4.0-7.0, such as pH 4.2, 4.4, 4.6, 4.8, 5.0, 5.2, 5.4, 5.6, 5.8, 6.0, 6.2, 6.4, 6.6, 6.8 or 7.0. Additionally or alternatively, the step of contacting may be at any suitable temperature, such as about 0-40° C., e.g. about 1-39, 2-38, 3-37, 4-36, 5-35, 6-34, 7-33, 8-32, 9-31 or 10-30° C., e.g. about 10, 12, 15, 18, 20, 22, 25, 28, 30, 33, 35 or 37° C., preferably about 25-35° C., e.g. about 25° C.

In some embodiments, contacting said peptide tag and polypeptide (peptide tag binding partner) of the invention "under conditions that enable the spontaneous formation of an isopeptide bond" includes contacting said peptide tag and polypeptide in the presence of a chemical chaperone, e.g. a molecule that enhances or improves the reactivity of the peptide tag and polypeptide (peptide tag binding partner). In some embodiments, the chemical chaperone is TMAO (trimethylamine N-oxide). In some embodiments, the chemical chaperone, e.g. TMAO, is present in the reaction at a concentration of at least about 0.2M, e.g. at least 0.3, 0.4, 0.5, 1.0, 1.5, 2.0 or 2.5M, e.g. about 0.2-3.0M, 0.5-2.0M, 1.0-1.5M.

As noted above, the formation of the isopeptide bond between the peptide tag and polypeptide (peptide tag binding partner) of the invention is spontaneous. In this respect, the polypeptide (peptide tag binding partner) comprises a glutamic acid at position 80 (or an equivalent position, based on the numbering of SEQ ID NO: 2) that facilitates, e.g. induces, promotes or catalyses, the formation of the isopeptide bond between the aspartate and lysine residues in the peptide tag and polypeptide (peptide tag binding partner), respectively.

The term "spontaneous" as used herein refers to an isopeptide bond, which can form in a protein or between peptides or proteins (e.g. between two peptides or a peptide and a protein, i.e. the peptide tag and polypeptide (peptide tag binding partner) of the invention) without any other agent (e.g. an enzyme catalyst) being present and/or without chemical modification of the protein or peptide, e.g. without native chemical ligation or chemical coupling using 1-ethyl-3-(3-dimethylaminopropyl) carbodiimide (EDC). Thus, native chemical ligation to modify a peptide or protein having a C-terminal thioester is not carried out.

Thus, a spontaneous isopeptide bond can form between a peptide tag and polypeptide (peptide tag binding partner) of the invention when in isolation and without chemical modification of the peptide tag and/or polypeptide of the invention. A spontaneous isopeptide bond may therefore form of its own accord in the absence of enzymes or other exogenous substances and without chemical modification of the peptide tag and/or polypeptide of the invention.

A spontaneous isopeptide bond may form almost immediately after contact of the peptide tag and polypeptide (peptide tag binding partner) of the invention, e.g. within 1, 2, 3, 4, 5, 10, 15, 20, 25 or 30 minutes, or within 1, 2, 4, 8, 12, 16, 20 or 24 hours.

The peptide tag and polypeptide (peptide tag binding partner) of the invention encompass mutant forms of the peptide tag and polypeptide (peptide tag binding partner) (i.e. referred to herein as homologues, variants or derivatives), which are structurally similar to the exemplified peptide tag set forth in SEQ ID NOs: 3-5 and the polypeptide (peptide tag binding partner) set forth in SEQ ID NO: 2, respectively. The peptide tag and polypeptide (peptide tag binding partner) variants of the invention are able to function as a peptide tag and binding partner (catcher), i.e. capable of spontaneously forming an isopeptide bond between the aspartic acid at position 10 (or equivalent position) of the peptide tag variant and the lysine at position 34 (or equivalent position) of the polypeptide (peptide tag binding partner) variant under suitable conditions as defined above.

In cases where a peptide tag or polypeptide (peptide tag binding partner) variant comprises mutations, e.g. deletions or insertions, relative to SEQ ID NOs: 1 and 2, respectively, the residues specified above are present at equivalent amino acid positions in the variant peptide tag and polypeptide (peptide tag binding partner) sequences. In some embodiments, deletions in the peptide tag and polypeptide (peptide tag binding partner) variants of the invention are not N-terminal and/or C-terminal truncations.

However, as mentioned above, it is contemplated that the polypeptide exemplified herein (i.e. SEQ ID NO: 2) may be truncated at the N-terminus and/or C-terminus without significantly reducing the activity of the polypeptide. In particular, the SEQ ID NO: 2 may be truncated by up to 24 amino acids at the N-terminus (e.g. 5, 10, 15 or 20 amino acids) and/or by up to 9 amino acids at the C-terminus (e.g. 1, 2, 3, 4, 5, 6, 7, 8 or 9 amino acids). Thus, the term variant as used herein includes truncation variants of the exemplified polypeptide. Alternatively, viewed, the invention may be seen to provide a portion of the exemplified polypeptide, wherein said portion comprises an amino acid sequence as set forth in SEQ ID NO: 101 or a variant thereof, as discussed above.

As referred to herein a "portion" comprises at least an amino acid sequence as set forth in SEQ ID NO: 101, i.e. at least 83, 84, 85, 86, 87, 88, 89, 90, 95, 100, 105, 110 or more amino acids of SEQ ID NO: 2 (the sequence from which it is derived) containing an amino acid sequence as set forth in SEQ ID NO: 101. Thus, said portion may be obtained from a central or N-terminal or C-terminal portion of the sequence. Preferably said portion is obtained from the central portion, i.e. it comprises an N-terminal and/or C-terminal truncation as defined above. Notably, "portion" as described herein are polypeptides of the invention and therefore satisfy the identity (relative to a comparable region) conditions and functional equivalence conditions mentioned herein.

In some embodiments, a peptide tag variant of the present invention may differ from SEQ ID NO: 1 by for example 1 to 5, 1 to 4, e.g. 1, 2 to 3 amino acid substitutions, insertions and/or deletions, preferably substitutions, as defined above. In some embodiments, the polypeptide (peptide tag binding partner) variant of the present invention may differ from SEQ ID NO: 2 as defined above.

Sequence identity may be determined by any suitable means known in the art, e.g. using the SWISS-PROT protein sequence databank using FASTA pep-cmp with a variable pamfactor, and gap creation penalty set at 12.0 and gap extension penalty set at 4.0, and a window of 2 amino acids. Other programs for determining amino acid sequence identity include the BestFit program of the Genetics Computer Group (GCG) Version 10 Software package from the University of Wisconsin. The program uses the local homology algorithm of Smith and Waterman with the default values: Gap creation penalty −8, Gap extension penalty=2, Average match=2.912, Average mismatch=−2.003.

Preferably said comparison is made over the full length of the sequence, but may be made over a smaller window of comparison, e.g. less than 100, 80 or 50 contiguous amino acids.

Preferably the peptide tag and polypeptide (peptide tag binding partner) variants (e.g. sequence identity-related variants) are functionally equivalent to the peptide tag and polypeptide (peptide tag binding partner) having a sequence as set forth in SEQ ID NOs: 3-5 or SEQ ID NOs: 2 or 101, respectively. As referred to herein, "functional equivalence" refers to variants of the peptide tag and polypeptide (peptide tag binding partner) of the invention discussed above that may show some reduced efficacy in the spontaneous formation of an isopeptide bond with its respective partner (e.g. lower expression yield, lower reaction rate, or activity in a limited range of reaction conditions (e.g. narrower temperature range, such as 10-30° C. etc.)) relative to the parent molecule (i.e. the molecule with which it shows sequence homology), but preferably are as efficient or are more efficient.

A mutant or variant peptide tag of the invention with activity that is "equivalent" to the activity of a peptide tag comprising or consisting of an amino acid sequence as set forth in one of SEQ ID NOs: 3-5 may have activity that is similar (i.e. comparable) to the activity of a peptide tag comprising or consisting of an amino acid sequence as set forth in one of SEQ ID NOs: 3-5, i.e. such that the practical applications of the peptide tag are not significantly affected, e.g. within a margin of experimental error. Thus, an equivalent peptide tag activity means that the mutant or variant peptide tag of the invention is capable of spontaneously forming an isopeptide bond with a polypeptide (peptide tag binding partner, e.g. comprising or consisting of an amino acid sequence as set forth in SEQ ID NO: 2, 7 or 101) with a similar reaction rate (i.e. rate constant as discussed below) and/or yield to a peptide tag comprising or consisting of an amino acid sequence as set forth in one of SEQ ID NOs: 3-5 under the same conditions.

Similarly, a mutant or variant polypeptide (peptide tag binding partner) of the invention with activity that is "equivalent" to the activity of a polypeptide (peptide tag binding partner) comprising or consisting of an amino acid sequence as set forth in SEQ ID NO: 2 or 101 (preferably SEQ ID NO: 2) may have activity that is similar (i.e. comparable) to the activity of a polypeptide (peptide tag binding partner) comprising or consisting of an amino acid sequence as set forth in SEQ ID NO: 2 or 101 (preferably SEQ ID NO: 2), i.e. such that the practical applications of the polypeptide (peptide tag binding partner) are not significantly affected, e.g. within a margin of experimental error. Thus, an equivalent polypeptide (peptide tag binding partner) activity means that the mutant or variant polypeptide (peptide tag binding partner) of the invention is capable of spontaneously forming an isopeptide bond with a peptide tag (e.g. comprising or consisting of an amino acid sequence as set forth in one of SEQ ID NOs: 3-6) with a similar reaction rate (i.e. rate constant as discussed below) and/or yield to a polypeptide (peptide tag binding partner) comprising or consisting of an amino acid sequence as set forth in SEQ ID NO: 2 or 101 (preferably SEQ ID NO: 2) under the same conditions.

The activity of different peptide tag and polypeptides (e.g. SEQ ID NO: 5 versus mutant or SEQ ID NO: 2 vs mutant, respectively) measured under the same reaction conditions, e.g. temperature, substrates (i.e. peptide tag or polypeptide sequences) and their concentration, buffer, salt etc. as exemplified above, can be readily compared to determine whether the activity for each peptide tag and polypeptide is higher, lower or equivalent.

In particular, the peptide tag and polypeptide variants of the invention have an equivalent rate constant to the peptide tag and polypeptide having a sequence as set forth in SEQ ID NOs: 3-5 or SEQ ID NOs: 2 or 101, respectively. The rate constant refers to the coefficient of proportionality relating the rate of the reaction (the formation of an isopeptide bond) at a given temperature to the product of the concentrations of reactants (i.e. the product of the concentration of the peptide tag and polypeptide of the invention).

Thus, the activity, e.g. rate constant, of the variant (e.g. mutant) peptide tag may be at least 60%, e.g. at least 70, 75, 80, 85 or 90% of the activity, e.g. rate constant, of a peptide tag comprising or consisting of an amino acid sequence as set forth in one of SEQ ID NOs: 3-5, such as at least 91, 92, 93, 94, 95, 96, 97, 98 or 99% of the activity of a peptide tag comprising or consisting of an amino acid sequence as set forth in one of SEQ ID NOs: 3-5. Alternatively viewed, the activity, e.g. rate constant, of the mutant peptide tag may be no more than 40% lower than the activity, e.g. rate constant, of a peptide tag comprising or consisting of an amino acid sequence as set forth in one of SEQ ID NOs: 3-5, e.g. no more than 35, 30, 25 or 20% lower than the activity, e.g. rate constant, of a peptide tag comprising or consisting of an amino acid sequence as set forth in one of SEQ ID NOs: 3-5, such as no more than 10, 9, 8, 7, 6, 5, 4, 3, 2 or 1% lower than the activity, e.g. rate constant, of a peptide tag comprising or consisting of an amino acid sequence as set forth in one of SEQ ID NOs: 3-5.

Similarly, the activity, e.g. rate constant, of the variant (e.g. mutant) polypeptide (peptide tag binding partner) of the invention may be at least 60%, e.g. at least 70, 75, 80, 85 or 90% of the activity, e.g. rate constant, of a polypeptide comprising or consisting of an amino acid sequence as set forth in SEQ ID NO: 2 or 101, such as at least 91, 92, 93, 94, 95, 96, 97, 98 or 99% of the activity, e.g. rate constant, of a polypeptide comprising or consisting of an amino acid sequence as set forth in SEQ ID NO: 2 or 101. Alternatively viewed, the activity of the mutant polypeptide may be no more than 40% lower than the activity, e.g. rate constant, of a polypeptide comprising or consisting of an amino acid sequence as set forth in SEQ ID NO: 2 or 101, e.g. no more than 35, 30, 25 or 20% lower than the activity, e.g. rate constant, of a polypeptide comprising or consisting of an amino acid sequence as set forth in SEQ ID NO: 2 or 101, such as no more than 10, 9, 8, 7, 6, 5, 4, 3, 2 or 1% lower than the activity, e.g. rate constant, of a polypeptide comprising or consisting of an amino acid sequence as set forth in SEQ ID NO: 2 or 101.

Notably, the rate constant of the reaction of the peptide tag and polypeptide of the invention may be lower than the values described in the Examples when the peptide tag and/or polypeptide are fused to large molecules or components (e.g. proteins), which diffuse slower than the isolated peptide tag and polypeptide. Moreover, the rate constant may be reduced if the molecules or components to which the peptide tag and/or polypeptide are fused cause steric hindrance to the reaction. Accordingly, when measuring the rate constant of the reaction of the peptide tag and polypeptide variants of the invention, it is preferred that measurement is perform using isolated peptide tags and polypeptides, i.e. peptide tags and polypeptides that are not fused or conjugated to other molecules or components.

It will be evident that fusion to large molecules or components and/or steric hindrance will also affect the rate constant of other peptide tags and polypeptides, e.g. SpyTag and SpyCatcher. Thus, the enhancements in rate constant of the peptide tag and polypeptide of the invention may still be advantageous when the peptide tag and polypeptide of the invention are used at high concentrations (e.g. when fused to large molecules or components) in addition to their use at low concentrations.

The reaction rate and rate constant can be assessed by any suitable means known in the art and as described in the Examples. For instance, the reaction rate may be monitored by assessing the mobility of the reaction products on SDS-PAGE after boiling in SDS or other strong denaturing treatment that would disrupt all non-covalent interactions or by mass spectrometry.

Hence, any modification or combination of modifications may be made to SEQ ID NO: 2 to produce a variant polypeptide (peptide tag binding partner) of the invention, provided that the variant polypeptide (peptide tag binding partner) comprises a lysine residue at a position equivalent to position 34 of SEQ ID NO: 2 and a glutamic acid residue at a position equivalent to position 80 of SEQ ID NO: 2 and at least one (preferably 2, 3, 4, 5, 6, 7, 8, 9 or 10) other amino acid residue(s) at positions equivalent to positions 5, 16, 40, 65, 92, 100, 108, 116 and optionally 12 and 22 of SEQ ID NO: 2 as defined above and retains the functional characteristics defined above, i.e. it results in a polypeptide (peptide tag binding partner) capable of spontaneously forming an isopeptide bond with a peptide tag comprising or consisting of an amino acid sequence as set forth in one of SEQ ID NOs: 3-6 and optionally has an equivalent or higher yield, reaction rate, e.g. rate constant, temperature and/or buffer range relative to a polypeptide (peptide tag binding partner) having an amino acid sequence as set forth in SEQ ID NO: 2.

Alternatively viewed, any modification or combination of modifications (preferably substitutions) may be made to SEQ ID NO: 101 to produce a variant polypeptide (peptide tag binding partner) of the invention, provided that the variant polypeptide (peptide tag binding partner) comprises a lysine residue at a position equivalent to position 10 of SEQ ID NO: 101 and a glutamic acid residue at a position equivalent to position 56 of SEQ ID NO: 101 and at least one (preferably 2, 3 or 4) other amino acid residue(s) at positions equivalent to positions 16, 41, 68 and 76 of SEQ ID NO: 101 as defined above and retains the functional characteristics defined above, i.e. it results in a polypeptide (peptide tag binding partner) capable of spontaneously forming an isopeptide bond with a peptide tag comprising or consisting of an amino acid sequence as set forth in one of SEQ ID NOs: 3-6 and optionally has an equivalent or higher yield, reaction rate, e.g. rate constant, temperature and/or buffer range relative to a polypeptide (peptide tag binding partner) having an amino acid sequence as set forth in SEQ ID NO: 101.

An equivalent position in the peptide tag of the invention is preferably determined by reference to the amino acid sequence of SEQ ID NO: 1 or 5. An equivalent position in the polypeptide (peptide tag binding partner) of the invention is determined by reference to the amino acid sequence of SEQ ID NO: 2 or 101. The homologous or corresponding position can be readily deduced by lining up the sequence of the homologue (mutant, variant or derivative) peptide tag and the sequence of SEQ ID NO: 1 or 5 or the sequence of the homologue (mutant, variant or derivative) polypeptide (peptide tag binding partner) and the sequence of SEQ ID NO: 2 or 101 based on the homology or identity between the sequences, for example using a BLAST algorithm.

The terms "tag" and "peptide tag" as used herein generally refer to a peptide or oligopeptide.

The term "peptide tag binding partner", "binding partner" or "catcher" as used herein generally refers to a polypeptide or protein.

In this respect, there is no standard definition regarding the size boundaries between what is meant by peptide or oligopeptide. Typically a peptide may be viewed as comprising between 2-20 amino acids and oligopeptide between 21-39 amino acids. Accordingly, a polypeptide may be viewed as comprising at least 40 amino acids, preferably at least 50, 60, 70, 80, 90, 100 or 110 amino acids.

Thus, in preferred embodiments a peptide tag as defined herein may be viewed as comprising at least 12 amino acids, e.g. 12-39 amino acids, such as e.g. 13-35, 14-34, 15-33, 16-31, 17-30 amino acids in length, e.g. it may comprise or consist of 12, 13, 14, 15, 16, 17, 18, 19 or 20 amino acids.

A polypeptide of the invention (a peptide tag binding partner, binding partner or "catcher") as defined herein may be viewed as comprising at least 80 amino acids, e.g. 80-150 amino acids, such as e.g. 80-140, 80-130, 80-120 amino acids in length, e.g. it may comprise or consist of 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120 amino acids.

As discussed above, two-part linkers (e.g. tag and catcher systems or pair, i.e. cognate pairs) have a large number of utilities and the peptide tag and polypeptide (peptide tag binding partner) of the invention find particular utility in conjugating (i.e. joining or linking) two molecules or components via an isopeptide bond. For instance, the peptide tag and polypeptide (peptide tag binding partner) may be separately conjugated or fused to molecules or components of interest and subsequently contacted together under conditions suitable to allow the spontaneous formation of an isopeptide bond between the peptide tag and polypeptide (peptide tag binding partner), thereby joining (i.e. linking or conjugating) the molecules or components via an isopeptide bond.

Thus, in some embodiments, the invention may be seen to provide the use of a peptide (peptide tag) and polypeptide (peptide tag binding partner) pair as defined herein to conjugate two molecules or components via an isopeptide bond, wherein said molecules or components conjugated via an isopeptide bond comprise:

a) a first molecule or component comprising (e.g. conjugated or fused to) a peptide (peptide tag) of the invention; and b) a second molecule or component comprising (e.g. conjugated or fused to) a polypeptide (peptide tag binding partner) of the invention.

It will be evident that the use of the peptide tag and polypeptide (peptide tag binding partner) pair (i.e. two-part linker) described above comprises contacting said first and second molecules under conditions suitable to enable (e.g. promote or facilitate) the spontaneous formation of an isopeptide bond between said peptide tag and polypeptide (peptide tag binding partner) as described above.

Alternatively viewed, the invention provides a process for conjugating two molecules or components via an isopeptide bond comprising:

a) providing a first molecule or component comprising (e.g. conjugated or fused to) a peptide (peptide tag) of the invention;

b) providing a second molecule or component comprising (e.g. conjugated or fused to) a polypeptide (peptide tag binding partner) of the invention;

c) contacting said first and second molecules or components under conditions that enable (e.g. promote or facilitate) the spontaneous formation of an isopeptide bond between the peptide and polypeptide as described above, thereby conjugating said first molecule or component to said second molecule or component via an isopeptide bond to form a complex.

The terms "conjugating" or "linking" in the context of the present invention with respect to connecting two or more molecules or components to form a complex refers to joining or conjugating said molecules or components, e.g. proteins, via a covalent bond, particularly an isopeptide bond which forms between the peptide tag and polypeptide (peptide tag binding partner) that are incorporated in, or fused to, said molecules or components, e.g. proteins (e.g. the peptide tag and polypeptide (peptide tag binding partner) may form domains of proteins to be conjugated or linked together).

As mentioned above, in some embodiments, the peptide tag and/or polypeptide (peptide tag binding partner) of the invention are fused or conjugated to other molecules or to other components or entities. Such molecules or components (i.e. entities) may be a nucleic acid molecule, protein, peptide, small-molecule organic compound, fluorophore, metal-ligand complex, polysaccharide, nanoparticle, nanotube, polymer, cell, virus, virus-like particle or any combination of these. In some embodiments the component or entity to which the peptide tag and/or polypeptide (peptide tag binding partner) is fused or conjugated is a solid support, i.e. solid substrate or solid phase, as defined below.

Thus, alternatively viewed, the invention provides a nucleic acid molecule, protein, peptide, small-molecule organic compound, fluorophore, metal-ligand complex, polysaccharide, nanoparticle, nanotube, polymer, cell, virus, virus-like particle or any combination thereof or solid support fused or conjugated to a peptide tag and/or polypeptide (peptide tag binding partner) of the invention.

The cell may be a prokaryotic or eukaryotic cell. In some embodiments, the cell is a prokaryotic cell, e.g. a bacterial cell.

In some embodiments, the peptide tag and/or polypeptide (peptide tag binding partner) may be conjugated or fused to a compound or molecule which has a therapeutic or prophylactic effect, e.g. an antibiotic, antiviral, vaccine, antitumour agent, e.g. a radioactive compound or isotope, cytokines, toxins, oligonucleotides and nucleic acids encoding genes or nucleic acid vaccines.

In some embodiments, the peptide tag and/or polypeptide (peptide tag binding partner) may be conjugated or fused to a label, e.g. a radiolabel, a fluorescent label, luminescent label, a chromophore label as well as to substances and enzymes which generate a detectable substrate, e.g. horseradish peroxidase, luciferase or alkaline phosphatase. This detection may be applied in numerous assays where antibodies are conventionally used, including Western blotting/immunoblotting, histochemistry, enzyme-linked immunosorbent assay (ELISA), or flow cytometry (FACS) formats. Labels for magnetic resonance imaging, positron emission tomography probes and boron 10 for neutron capture therapy may also be conjugated to the peptide tag and/or polypeptide (peptide tag binding partner) of the invention. Particularly, the peptide tag and/or polypeptide (peptide tag binding partner) may be fused or produced with another peptide, for example His6 tag, and/or may be fused or produced with another protein, for example with the purpose of enhancing recombinant protein expression by fusing to Maltose Binding Protein.

In a particularly useful embodiment, the peptide tag and/or polypeptide (peptide tag binding partner) is fused or conjugated with another peptide, oligopeptide or polypeptide. For instance, the peptide tag and/or polypeptide (peptide tag binding partner) may be produced as part of another peptide, oligopeptide or polypeptide using recombinant techniques as discussed below, i.e. as a recombinant or synthetic protein or polypeptide.

It will be evident that the peptide tag and/or polypeptide (peptide tag binding partner) of the invention may be fused to any protein or polypeptide. The protein may be derived or obtained from any suitable source. For instance, the protein may be in vitro translated or purified from biological and clinical samples, e.g. any cell or tissue sample of an organism (eukaryotic, prokaryotic), or any body fluid or preparation derived therefrom, as well as samples such as cell cultures, cell preparations, cell lysates etc. Proteins may be derived or obtained, e.g. purified from environmental samples, e.g. soil and water samples or food samples are also included. The samples may be freshly prepared or they may be prior-treated in any convenient way e.g. for storage.

As noted above, in a preferred embodiment, the peptide, oligopeptide or protein fused to the peptide tag and/or polypeptide of the invention may be produced recombinantly and thus the nucleic acid molecules encoding said recombinant proteins may be derived or obtained from any suitable source, e.g. any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa, viruses etc. In some embodiments, the proteins may be synthetic proteins. For example, the peptide and polypeptide (proteins) disclosed herein may be produced by chemical synthesis, such as solid-phase peptide synthesis.

The position of the peptide tag and/or polypeptide (peptide tag binding partner) within a recombinant or synthetic protein is not particularly important. Thus, in some embodiments the peptide tag and/or polypeptide (peptide tag binding partner) may be located at the N-terminus or C-terminus of the recombinant or synthetic polypeptide. In some embodiments, the peptide tag and/or polypeptide (peptide tag binding partner) may be located internally within the recombinant or synthetic polypeptide. Thus, in some embodiments the peptide tag and/or polypeptide (peptide tag binding partner) may be viewed as an N-terminal, C-terminal or internal domain of the recombinant or synthetic polypeptide.

In some preferred embodiments, the polypeptide (peptide tag binding partner) is preferably located at the N-terminus or C-terminus of the recombinant or synthetic polypeptide. Thus, in some embodiments the polypeptide (peptide tag binding partner) may be viewed as an N-terminal or C-terminal domain of the recombinant or synthetic polypeptide.

In some embodiments, it may be useful to include one or more spacers, e.g. a peptide spacer, between the peptide, oligopeptide or polypeptide to be joined or conjugated with peptide tag and/or polypeptide (peptide tag binding partner). Thus, the peptide, oligopeptide or polypeptide and peptide tag and/or polypeptide (peptide tag binding partner) may be linked directly to each other or they may be linked indirectly by means of one or more spacer sequences. Thus, a spacer sequence may interspace or separate two or more individual parts of the recombinant or synthetic polypeptide. In some embodiments, a spacer may be N-terminal or C-terminal to the peptide tag and/or polypeptide (peptide tag binding partner). In some embodiments, spacers may be at both sides of the peptide tag and/or polypeptide (peptide tag binding partner).

The precise nature of the spacer sequence is not critical and it may be of variable length and/or sequence, for example it may have 1-40, more particularly 2-20, 1-15, 1-12, 1-10, 1-8, or 1-6 residues, e.g. 6, 7, 8, 9, 10 or more residues. By way of representative example the spacer sequence, if present, may have 1-15, 1-12, 1-10, 1-8 or 1-6 residues etc. The nature of the residues is not critical and they may for example be any amino acid, e.g. a neutral amino acid, or an aliphatic amino acid, or alternatively they may be hydrophobic, or polar or charged or structure-forming e.g. proline. In some preferred embodiments, the linker is a serine and/or glycine-rich sequence.

Exemplary spacer sequences thus include any single amino acid residue, e.g. S, G, L, V, P, R, H, M, A or E or a di-, tri- tetra- penta- or hexa-peptide composed of one or more of such residues.

Thus, in some embodiments, the invention provides a recombinant or synthetic polypeptide comprising a peptide tag and/or polypeptide (peptide tag binding partner) of the invention as defined above, i.e. a recombinant or synthetic polypeptide comprising a peptide, oligopeptide or polypeptide (e.g. a heterologous peptide, oligopeptide or polypeptide, i.e. a peptide, oligopeptide or polypeptide that is not normally associated with the peptide tag or polypeptide of the invention, e.g. from a different organism) fused to a peptide tag and/or polypeptide (peptide tag binding partner) of the invention. The recombinant or synthetic polypeptide optionally comprises a spacer as defined above.

The recombinant or synthetic polypeptide of the invention may also comprise purification moieties or tags to facilitate their purification (e.g. prior to use in the methods and uses of the invention discussed below). Any suitable purification moiety or tag may be incorporated into the polypeptide and such moieties are well known in the art. For instance, in some embodiments, the recombinant or synthetic polypeptide may comprise a peptide purification tag or moiety, e.g. a His-tag sequence. Such purification moieties or tags may be incorporated at any position within the polypeptide. In some preferred embodiments, the purification moiety is located at or towards (i.e. within 5, 10, 15, 20 amino acids of) the N- or C-terminus of the polypeptide.

As noted above, an advantage of the present invention arises from the fact that the peptide tags and/or polypeptide (peptide tag binding partner) incorporated in a peptide, oligopeptide or polypeptide (e.g. the recombinant or synthetic polypeptides of the invention) may be completely genetically encoded. Thus, in a further aspect, the invention provides a nucleic acid molecule encoding a peptide tag, polypeptide (peptide tag binding partner) or recombinant or synthetic polypeptide as defined above.

In some embodiments, the nucleic acid molecule encoding a peptide tag defined above comprises a nucleotide sequence as set forth in any one of SEQ ID NOs: 11-13 or a nucleotide sequence with at least 80% sequence identity to a sequence as set forth in any one of SEQ ID NOs: 11-13.

In some embodiments, the nucleic acid molecule encoding a binding partner defined above comprises a nucleotide sequence as set forth in SEQ ID NO: 14 or a nucleotide sequence with at least 80% sequence identity to a sequence as set forth in SEQ ID NO: 14.

Preferably, the nucleic acid molecule above is at least 85, 90, 95, 96, 97, 98, 99 or 100% identical to the sequence to which it is compared.

Nucleic acid sequence identity may be determined by, e.g. FASTA Search using GCG packages, with default values and a variable pamfactor, and gap creation penalty set at 12.0 and gap extension penalty set at 4.0 with a window of 6 nucleotides. Preferably said comparison is made over the full length of the sequence, but may be made over a smaller window of comparison, e.g. less than 600, 500, 400, 300, 200, 100 or 50 contiguous nucleotides.

The nucleic acid molecules of the invention may be made up of ribonucleotides and/or deoxyribonucleotides as well as synthetic residues, e.g. synthetic nucleotides, that are capable of participating in Watson-Crick type or analogous base pair interactions. Preferably, the nucleic acid molecule is DNA or RNA.

The nucleic acid molecules described above may be operatively linked to an expression control sequence, or a recombinant DNA cloning vehicle or vector containing such a recombinant DNA molecule. This allows cellular expression of the peptides and polypeptides of the invention as a gene product, the expression of which is directed by the gene(s) introduced into cells of interest. Gene expression is directed from a promoter active in the cells of interest and may be inserted in any form of linear or circular nucleic acid (e.g. DNA) vector for incorporation in the genome or for independent replication or transient transfection/expression. Suitable transformation or transfection techniques are well described in the literature. Alternatively, the naked nucleic acid (e.g. DNA or RNA, which may include one or more synthetic residues, e.g. base analogues) molecule may be introduced directly into the cell for the production of peptides and polypeptides of the invention. Alternatively the nucleic acid may be converted to mRNA by in vitro transcription and the relevant proteins may be generated by in vitro translation.

Appropriate expression vectors include appropriate control sequences such as for example translational (e.g. start and stop codons, ribosomal binding sites) and transcriptional control elements (e.g. promoter-operator regions, termination stop sequences) linked in matching reading frame with the nucleic acid molecules of the invention. Appropriate vectors may include plasmids and viruses (including both bacteriophage and eukaryotic viruses). Suitable viral vectors include baculovirus and also adenovirus, adeno-associated virus, herpes and vaccinia/pox viruses. Many other viral vectors are described in the art. Examples of suitable vectors include bacterial and mammalian expression vectors pGEX-KG, pEF-neo and pEF-HA.

As noted above, the recombinant or synthetic polypeptide of the invention may comprise additional sequences (e.g. peptide/polypeptides tags to facilitate purification of the polypeptide) and thus the nucleic acid molecule may conveniently be fused with DNA encoding an additional peptide or polypeptide, e.g. His-tag, maltose-binding protein, to produce a fusion protein on expression.

Thus viewed from a further aspect, the present invention provides a vector, preferably an expression vector, comprising a nucleic acid molecule as defined above.

Other aspects of the invention include methods for preparing recombinant nucleic acid molecules according to the invention, comprising inserting nucleic acid molecule of the invention encoding the peptide tag and/or polypeptide (peptide tag binding partner) of the invention into vector nucleic acid.

Nucleic acid molecules of the invention, preferably contained in a vector, may be introduced into a cell by any appropriate means. Suitable transformation or transfection techniques are well described in the literature. Numerous techniques are known and may be used to introduce such vectors into prokaryotic or eukaryotic cells for expression. Preferred host cells for this purpose include insect cell lines, yeast, mammalian cell lines or *E. coli*, such as strain BL21/DE3. The invention also extends to transformed or transfected prokaryotic or eukaryotic host cells containing a nucleic acid molecule, particularly a vector as defined above.

Thus, in another aspect, there is provided a recombinant host cell containing a nucleic acid molecule and/or vector as described above.

By "recombinant" is meant that the nucleic acid molecule and/or vector has been introduced into the host cell. The host cell may or may not naturally contain an endogenous copy of the nucleic acid molecule, but it is recombinant in that an exogenous or further endogenous copy of the nucleic acid molecule and/or vector has been introduced.

A further aspect of the invention provides a method of preparing a peptide tag and/or polypeptide (peptide tag binding partner) of the invention as hereinbefore defined, which comprises culturing a host cell containing a nucleic acid molecule as defined above, under conditions whereby said nucleic acid molecule encoding said peptide tag and/or polypeptide (peptide tag binding partner) is expressed and recovering said molecule (peptide tag and/or polypeptide (peptide tag binding partner)) thus produced. The expressed peptide tag and/or polypeptide (peptide tag binding partner) forms a further aspect of the invention.

In some embodiments, the peptide tag and/or polypeptide (peptide tag binding partner) of the invention, or for use in the method and uses of the invention, may be generated synthetically, e.g. by ligation of amino acids or smaller synthetically generated peptides, or more conveniently by recombinant expression of a nucleic acid molecule encoding said polypeptide as described hereinbefore.

Nucleic acid molecules of the invention may be generated synthetically by any suitable means known in the art.

Thus, the peptide tag and/or polypeptide (peptide tag binding partner) of the invention may be an isolated, purified, recombinant or synthesised peptide tag or polypeptide.

The term "polypeptide" is used herein interchangeably with the term "protein". As noted above, the term polypeptide or protein typically includes any amino acid sequence comprising at least 40 consecutive amino acid residues, e.g. at least 50, 60, 70, 80, 90, 100, 150 amino acids, such as 40-1000, 50-900, 60-800, 70-700, 80-600, 90-500, 100-400 amino acids.

Similarly, the nucleic acid molecules of the invention may be an isolated, purified, recombinant or synthesised nucleic acid molecule.

Thus, alternatively viewed, the peptide tag, polypeptides and nucleic acid molecules of the invention preferably are non-native, i.e. non-naturally occurring, molecules.

Standard amino acid nomenclature is used herein. Thus, the full name of an amino acid residue may be used interchangeably with one letter code or three letter abbreviations. For instance, lysine may be substituted with K or Lys, isoleucine may be substituted with I or Ile, and so on. Moreover, the terms aspartate and aspartic acid, and glutamate and glutamic acid are used interchangeably herein and may be replaced with Asp or D, or Glu or E, respectively.

Whilst it is envisaged that the peptide tag and polypeptide (peptide tag binding partner) of, and for use in, the invention may be produced recombinantly, and this is a preferred embodiment of the invention, it will be evident that the peptide tag and polypeptide (peptide tag binding partner) of the invention may be conjugated to proteins or other entities, e.g. molecules or components, as defined above by other means. In other words, the peptide tag or polypeptide (peptide tag binding partner) and other molecule, component or entity, e.g. protein, may be produced separately by any suitable means, e.g. recombinantly, and subsequently conjugated (joined) to form a peptide tag-other component conjugate or polypeptide (peptide tag binding partner)—other component conjugate that can be used in the methods and uses of the invention. For instance, the peptide tag and/or polypeptide (peptide tag binding partner) of the invention may be produced synthetically or recombinantly, as described above, and conjugated to another component, e.g. a protein via a non-peptide linker or spacer, e.g. a chemical linker or spacer.

Thus, in some embodiments, the peptide tag and/or polypeptide (peptide tag binding partner) and other component, e.g. protein, may be joined together either directly through a bond or indirectly through a linking group. Where linking groups are employed, such groups may be chosen to provide for covalent attachment of the peptide tag or polypeptide (peptide tag binding partner) and other entity, e.g. protein, through the linking group. Linking groups of interest may vary widely depending on the nature of the other entity, e.g. protein. The linking group, when present, is in many embodiments biologically inert.

Many linking groups are known to those of skill in the art and find use in the invention. In representative embodiments, the linking group is generally at least about 50 daltons, usually at least about 100 daltons and may be as large as 1000 daltons or larger, for example up to 1000000 daltons if the linking group contains a spacer, but generally will not exceed about 500 daltons and usually will not exceed about 300 daltons. Generally, such linkers will comprise a spacer group terminated at either end with a reactive functionality capable of covalently bonding to the peptide tag or binding partner and other molecule or component, e.g. protein.

Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine, oligoethylene glycol and polyethylene glycol. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject blocking reagent include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like. For instance, a spacer may be formed with an azide reacting with an alkyne or formed with a tetrazine reacting with a trans-cyclooctene or a norbornene.

In some embodiments, it may be useful to modify one or more residues in the peptide tag and/or polypeptide (peptide tag binding partner) to facilitate the conjugation of these molecules and/or to improve the stability of the peptide tag and/or polypeptide (peptide tag binding partner). Thus, in some embodiments, the peptide tag or polypeptide (peptide tag binding partner) of, or for use in, the invention may comprise unnatural or non-standard amino acids.

In some embodiments, the peptide tag or polypeptide (peptide tag binding partner) of, or for use in, the invention may comprise one or more, e.g. at least 1, 2, 3, 4, 5 non-conventional amino acids, such as 10, 15, 20 or more non-conventional, i.e. amino acids which possess a side chain that is not coded for by the standard genetic code, termed herein "non-coded amino acids" (see e.g. Table 1). These may be selected from amino acids which are formed through metabolic processes such as ornithine or taurine, and/or artificially modified amino acids such as 9H-fluoren-9-ylmethoxycarbonyl (Fmoc), (tert)-(B)utyl (o)xy (c)arbonyl (Boc), 2,2,5,7,8-pentamethylchroman-6-sulphonyl (Pmc) protected amino acids, or amino acids having the benzyloxy-carbonyl (Z) group.

Examples of non-standard or structural analogue amino acids which may be used in the peptide tag or polypeptide (peptide tag binding partner) of, and for use in, the invention are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methyl-amino acids, D-α methylamino acids, D-N-methylamino acids. Examples of non-conventional, i.e. non-coded, amino acids are listed in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| | | L-N-methylasparagine | Nmasn |
| aminocyclopropane-carboxylate | Cpro | L-N-methylaspartic acid | Nmasp |
| | | L-N-methylcysteine | Nmcys |
| aminoisobutyric acid | Aib | L-N-methylglutamine | Nmgln |
| aminonorbornyl-carboxylate | Norb | L-N-methylglutamic acid | Nmglu |
| | | L-N-methylhistidine | Nmhis |
| cyclohexylalanine | Chexa | L-N-methylisolleucine | Nmile |
| cyclopentylalanine | Cpen | L-N-methylleucine | Nmleu |
| D-alanine | Dal | L-N-methyllysine | Nmlys |
| D-arginine | Darg | L-N-methylmethionine | Nmmet |
| D-aspartic acid | Dasp | L-N-methylnorleucine | Nmnle |
| D-cysteine | Dcys | L-N-methylnorvaline | Nmnva |
| D-glutamine | Dgln | L-N-methylornithine | Nmorn |
| D-glutamic acid | Dglu | L-N-methylphenylalanine | Nmphe |
| D-histidine | Dhis | L-N-methylproline | Nmpro |
| D-isoleucine | Dile | L-N-methylserine | Nmser |
| D-leucine | Dleu | L-N-methylthreonine | Nmthr |
| D-lysine | Dlys | L-N-methyltryptophan | Nmtrp |
| D-methionine | Dmet | L-N-methyltyrosine | Nmtyr |
| D-ornithine | Dorn | L-N-methylvaline | Nmval |
| D-phenylalanine | Dphe | L-N-methylethylglycine | Nmetg |
| D-proline | Dpro | L-N-methyl-t-butylglycine | Nmtbug |
| D-serine | Dser | L-norleucine | Nle |
| D-threonine | Dthr | L-norvaline | Nva |
| D-tryptophan | Dtrp | α-methyl-aminoisobutyrate | Maib |
| D-tyrosine | Dtyr | α-methyl-γ-aminobutyrate | Mgabu |
| D-valine | Dval | α-methylcyclohexylalanine | Mchexa |
| D-α-methylalanine | Dmala | α-methylcylcopentylalanine | Mcpen |
| D-α-methylarginine | Dmarg | α-methyl-α-napthylalanine | Manap |
| D-α-methylasparagine | Dmasn | α-methylpenicillamine | Mpen |
| D-α-methylaspartate | Dmasp | N-(4-aminobutyl)glycine | Nglu |
| D-α-methylcysteine | Dmcys | N-(2-aminoethyl)glycine | Naeg |
| D-α-methylglutamine | Dmgln | N-(3-aminopropyl)glycine | Norn |
| D-α-methylhistidine | Dmhis | N-amino-α-methylbutyrate | Nmaabu |
| D-α-methylisoleucine | Dmile | α-napthylalanine | Anap |
| D-α-methylleucine | Dmleu | N-benzylglycine | Nphe |
| D-α-methyllysine | Dmlys | N-(2-carbamylethyl)glycine | Ngln |
| D-α-methylmethionine | Dmmet | N-(carbamylmethyl)glycine | Nasn |
| D-α-methylornithine | Dmorn | N-(2-carboxyethyl)glycine | Nglu |
| D-α-methylphenylalanine | Dmphe | N-(carboxymethyl)glycine | Nasp |
| | | N-cyclobutylglycine | Ncbut |
| D-α-methylproline | Dmpro | N-cycloheptylglycine | Nchep |
| D-α-methylserine | Dmser | N-cyclohexylglycine | Nchex |
| D-α-methylthreonine | Dmthr | N-cyclodecylglycine | Ncdec |
| D-α-methyltryptophan | Dmtrp | N-cylcododecylglycine | Ncdod |
| D-α-methyltyrosine | Dmty | N-cyclooctylglycine | Ncoct |
| D-α-methylvaline | Dmval | N-cyclopropylglycine | Ncpro |
| D-N-methylalanine | Dnmala | N-cycloundecylglycine | Ncund |
| D-N-methylarginine | Dnmarg | N-(2,2-diphenylethyl)glycine | Nbhm |
| D-N-methylasparagine | Dnmasn | | |
| D-N-methylaspartate | Dnmasp | N-(3,3-diphenylpropyl)glycine | Nbhe |
| D-N-methylcysteine | Dnmcys | | |
| D-N-methylglutamine | Dnmgln | N-(3-guanidinopropyl)glycine | Narg |
| D-N-methylglutamate | Dnmglu | | |
| D-N-methylhistidine | Dnmhis | N-(1-hydroxyethyl)glycine | Nthr |
| D-N-methylisoleucine | Dnmile | N-(hydroxyethyl))glycine | Nser |
| D-N-methylleucine | Dnmleu | N-(imidazolylethyl))glycine | Nhis |
| D-N-methyllysine | Dnmlys | N-(3-indolylyethyl)glycine | Nhtrp |
| N-methyl-cyclohexylalanine | Nmchexa | N-methyl-γ-aminobutyrate | Nmgabu |
| | | D-N-methylmethionine | Dnmmet |
| D-N-methylornithine | Dnmorn | N-methylcyclopentylalanine | Nmcpen |
| N-methylglycine | Nala | | |
| N-methyl-aminoisobutyrate | Nmaib | D-N-methylphenylalanine | Dnmphe |
| | | D-N-methylproline | Dnmpro |
| N-(1-methylpropyl)glycine | Nile | D-N-methylserine | Dnmser |
| | | D-N-methylthreonine | Dnmthr |
| N-(2-methylpropyl)glycine | Nleu | N-(1-methylethyl)glycine | Nval |
| | | N-methyla-napthylalanine | Nmanap |
| D-N-methyltryptophan | Dnmtrp | N-methylpenicillamine | Nmpen |
| D-N-methyltyrosine | Dnmtyr | N-(p-hydroxyphenyl)glycine | Nhtyr |
| D-N-methylvaline | Dnmval | | |
| γ-aminobutyric acid | Gabu | N-(thiomethyl)glycine | Ncys |
| L-t-butylglycine | Tbug | penicillamine | Pen |
| L-ethylglycine | Etg | L-α-methylalanine | Mala |
| L-homophenylalanine | Hphe | L-α-methylasparagine | Masn |
| L-α-methylarginine | Marg | L-α-methyl-t-butylglycine | Mtbug |
| L-α-methylaspartate | Masp | L-methylethylglycine | Metg |
| L-α-methylcysteine | Mcys | L-α-methylglutamate | Mglu |
| L-α-methylglutamine | Mgln | L-α-methylhomophenylalanine | Mhphe |
| L-α-methylhistidine | Mhis | | |
| L-α-methylisoleucine | Mile | N-(2-methylthioethyl)glycine | Nmet |
| L-α-methylleucine | Mleu | | |
| L-α-methylmethionine | Mmet | L-α-methyllysine | Mlys |
| L-α-methylnorvaline | Mnva | L-α-methylnorleucine | Mnle |
| L-α-methylphenylalanine | Mphe | L-α-methylornithine | Morn |
| | | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2- | Nmbc | L-O-methyl serine | Omser |
| | | L-O-methyl homoserine | Omhse |

TABLE 1-continued

| Non-conventional amino acid | Code | Non-conventional amino acid | Code |
|---|---|---|---|
| diphenyl-ethylamino) cyclopropane | | | |

In some embodiments, it may be useful to fuse or conjugate the peptide tag and/or polypeptide (peptide tag binding partner) of the invention to a solid substrate (i.e. a solid phase or solid support) and it will be evident that this may be achieved in any convenient way. Thus the manner or means of immobilisation and the solid support may be selected, according to choice, from any number of immobilisation means and solid supports as are widely known in the art and described in the literature. Thus, the peptide tag and/or polypeptide (peptide tag binding partner) may be directly bound to the support, for example via a domain or moiety of the peptide tag or polypeptide (peptide tag binding partner) (e.g. chemically cross-linked). In some embodiments, the peptide tag or polypeptide (peptide tag binding partner) may be bound indirectly by means of a linker group, or by an intermediary binding group(s) (e.g. by means of a biotin-streptavidin interaction). Thus, the peptide tag or polypeptide (peptide tag binding partner) may be covalently or non-covalently linked to the solid support. The linkage may be a reversible (e.g. cleavable) or irreversible linkage. Thus, in some embodiments, the linkage may be cleaved enzymatically, chemically, or with light, e.g. the linkage may be a light-sensitive linkage.

Thus, in some embodiments, a peptide tag or polypeptide (peptide tag binding partner) may be provided with means for immobilisation (e.g. an affinity binding partner, e.g. biotin or a hapten, capable of binding to its binding partner, i.e. a cognate binding partner, e.g. streptavidin or an antibody) provided on the support. In some embodiments, the interaction between the peptide tag or polypeptide (peptide tag binding partner) and the solid support must be robust enough to allow for washing steps, i.e. the interaction between the peptide tag or polypeptide (peptide tag binding partner) and solid support is not disrupted (significantly disrupted) by the washing steps. For instance, it is preferred that with each washing step, less than 5%, preferably less than 4, 3, 2, 1, 0.5 or 0.1% of the peptide tag or polypeptide (peptide tag binding partner) is removed or eluted from the solid phase.

The solid support (phase or substrate) may be any of the well-known supports or matrices which are currently widely used or proposed for immobilisation, separation etc. These may take the form of particles (e.g. beads which may be magnetic, para-magnetic or non-magnetic), sheets, gels, filters, membranes, fibres, capillaries, slides, arrays or microtitre strips, tubes, plates or wells etc.

The support may be made of glass, silica, latex or a polymeric material. Suitable are materials presenting a high surface area for binding of the fusion protein. Such supports may have an irregular surface and may be for example porous or particulate, e.g. particles, fibres, webs, sinters or sieves. Particulate materials, e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10, and e.g. not more than 6 µm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the isopeptide bond formation steps.

In some embodiments, the solid support is an amylose resin.

In a further embodiment, the invention provides a kit, particularly a kit for use in the processes and uses of the invention, i.e. for conjugating two molecules or components via an isopeptide bond, wherein two of the molecules or components in the complex are conjugated via an isopeptide bond, wherein said kit comprises:

(a) a peptide (peptide tag) as defined above, optionally conjugated or fused to a molecule or component, e.g. a protein; and (b) a polypeptide (peptide tag binding partner) as defined above, optionally conjugated or fused to a molecule or component, e.g. a protein such as a recombinant or synthetic polypeptide comprising a polypeptide (peptide tag binding partner) as defined above; and/or (c) a nucleic acid molecule, particularly a vector, encoding a peptide (peptide tag) as defined in (a); and (d) a nucleic acid molecule, particularly a vector, encoding a polypeptide (peptide tag binding partner) as defined in (b).

It will be evident that the peptide tag and polypeptide (peptide tag binding partner) of the invention have a wide range of utilities. Alternatively viewed, the peptide tag and polypeptide (peptide tag binding partner) of the invention may be employed in a variety of industries.

For instance, in some embodiments, the peptide tag and polypeptide (peptide tag binding partner) of the invention may find utility in targeting fluorescent or other biophysical probes or labels to specific proteins. In this respect, the protein of interest may be modified to incorporate a peptide tag of the invention (e.g. one of SEQ ID NOs: 3-5), as discussed above, and the fluorescent or other biophysical probe or label may be fused or conjugated to the polypeptide (peptide tag binding partner, e.g. SEQ ID NO: 2). The modified protein and probe or label may be contacted together under conditions suitable to allow the spontaneous formation of an isopeptide bond between the peptide tag and polypeptide (peptide tag binding partner), thereby labelling the protein with the label or probe via an isopeptide bond.

In some embodiments, the peptide tag and polypeptide (peptide tag binding partner) of the invention may find utility in protein immobilisation for proteomics. In this respect, the proteins of interest may be modified to incorporate a peptide tag of the invention (e.g. one of SEQ ID NOs: 3-5) and a solid substrate may be fused or conjugated to the polypeptide (peptide tag binding partner, e.g. SEQ ID NO: 2). The modified proteins and solid substrate may be contacted together under conditions suitable to allow the spontaneous formation of an isopeptide bond between the peptide tag and polypeptide (peptide tag binding partner), thereby immobilising the proteins on the solid substrate via an isopeptide bond. It will be evident that the peptide tag and polypeptide (peptide tag binding partner) of the invention may be used to simultaneously immobilise multiple proteins on a solid phase/substrate.

In still further embodiments, the peptide tag and polypeptide (peptide tag binding partner) of the invention may find utility in conjugation of antigens to virus-like particles, viruses, bacteria or multimerisation scaffolds for vaccination. For instance, the production of virus-like particles, viruses or bacteria that display the polypeptide (peptide tag binding partner) of the invention (e.g. SEQ ID NO: 2) on the surface would facilitate the conjugation of antigens comprising the peptide tag of the invention (e.g. one of SEQ ID NOs: 3-5) to their surface via an isopeptide bond. In this respect, antigen multimerisation gives rise to greatly enhanced immune responses. Thus, in some embodiments, the molecule or component fused to the polypeptide of the invention is a viral capsid protein and/or the molecule or component fused to the peptide tag of the invention is an antigen, e.g. an antigen associated with a particular disease, e.g. infection.

In other embodiments, the peptide tag and polypeptide (peptide tag binding partner) may be used to cyclise an enzyme, e.g. by fusing peptide tag and binding partner to each end of the enzyme and subsequently allowing the spontaneous formation of the isopeptide bond between the peptide tag and polypeptide (peptide tag binding partner). In this respect, cyclisation of enzymes has been shown to increase enzyme resilience.

In particular, cyclisation of enzymes or enzyme polymers (fusion proteins) may improve the thermostability of the protein or protein units in the enzyme polymer. In this respect, enzymes are valuable tools in many processes but are unstable and hard to recover. Enzyme polymers have greater stability to temperature, pH and organic solvents and there is an increased desire to use enzyme polymers in industrial processes. However, enzyme polymer generation commonly uses a glutaraldehyde non-specific reaction and this will damage or denature (i.e. reduce the activity of) many potentially useful enzymes. Site-specific linkage of proteins into chains (polymers) through isopeptide bonds using the peptide tag and polypeptide (peptide tag binding partner) of the present invention is expected to enhance enzyme resilience, such as in diagnostics or enzymes added to animal feed. In particularly preferred embodiments, enzymes may be stabilised by cyclisation, as discussed above.

The peptide tag and polypeptide (peptide tag binding partner) of the invention could also be used to link multiple enzymes into pathways to promote metabolic efficiency, as described in WO 2016/193746. In this respect, enzymes often come together to function in pathways inside cells and traditionally it has been difficult to connect multiple enzymes together outside cells (in vitro). Thus, the peptide tag and polypeptide (peptide tag binding partner) of the invention could be used to couple or conjugate enzymes to produce fusion proteins and therefore enhance activity of multi-step enzyme pathways, which could be useful in a range of industrial conversions and for diagnostics.

The peptide tag and polypeptide (peptide tag binding partner) of the invention will also find utility in the production of antibody polymers. In this respect, antibodies are one of the most important class of pharmaceuticals and are often used attached to surfaces. However, antigen mixing in a sample, and therefore capture of said antigen in said sample, are inefficient near surfaces. By extending chains of antibodies, it is anticipated that capture efficiency will be improved. This will be especially valuable in circulating tumour cell isolation, which at present is one of the most promising ways to enable early cancer diagnosis.

In a still further embodiment, the peptide tag and polypeptide (peptide tag binding partner) of the invention may find utility in the production of drugs for activating cell signalling. In this respect, many of the most effective ways to activate cellular function are through protein ligands. However, in nature a protein ligand will usually not operate alone but with a specific combination of other signalling molecules. Thus, the peptide tag and polypeptide (peptide tag binding partner) of the invention allows the generation of tailored fusion proteins (i.e. protein teams), which could give optimal activation of cellular signalling. These fusion proteins (protein teams) might be applied for controlling cell survival, division, or differentiation.

In yet further embodiments, the peptide tag and polypeptide (peptide tag binding partner) of the invention may find utility in the generation of hydrogels for growth of eukaryotic cells, e.g. neurons, stem cells, preparation of biomaterials, antibody functionalisation with dyes or enzymes and stabilising enzymes by cyclisation.

BRIEF DESCRIPTION OF THE DRAWINGS

The invention will now be described in more detail in the following non-limiting Example with reference to the following drawings:

FIG. 2 shows (A) a bar chart demonstrating the amount of SpyTag-phage recovered after selecting with the wild-type (WT) SpyCatcher bait, compared with the non-reactive SpyCatcher EQ, quantified as colony forming units (cfu) (mean±1 s.d., n=3); and (B) a table of selected sequences of SpyTag variants from the final rounds of selection of the N-terminal library (NLib1-3, SEQ ID NOs: 15-17) and the subsequent C-terminal library (CLib1-10, SEQ ID NOs: 18-27). WT refers to the sequence of SpyTag (SEQ ID NO: 6) and SpyTag002 refers to a variant with an improved reaction rate, SEQ ID NO: 3.

FIG. 4 shows (A) a cartoon of the phage display selection scheme for accelerated SpyCatcher variants. SpyCatcher mutants on M13 phage are panned against biotinylated AviTag-SpyTag-MBP bait, before TEV protease elution from streptavidin-beads; and (B) shows a bar chart demonstrating the amount of SpyCatcher-phage recovered after screening with the WT SpyTag-MBP or the non-reactive SpyTag DA-MBP control, quantified as cfu (mean±1 s.d., n=3).

FIG. 5 shows an alignment of amino acid sequences of selected variants from the final round of SpyCatcher library selections. * no change, very conservative change, conservative change, and gap indicates distant change. WT refers to SEQ ID NO: 7, L1C1 refers to SEQ ID NO:33, L1C4 refers to SEQ ID NO:34, L1C2 refers to SEQ ID NO:35, L2C1 refers to SEQ ID NO:36, L1C3 refers to SEQ ID NO:37, L1C6 refers to SEQ ID NO:38, L2C8 refers to SEQ ID NO:39, and SC002 refers to SEQ ID NO:40.

FIG. 9 shows (A) an SDS-PAGE gel depicting the characterisation of spontaneous isopeptide bond formation between SpyCatcher002 and SpyTag002. SpyCatcher002 and SpyTag002-MBP were mixed at 10 μM for 1 h in succinate-phosphate-glycine buffer at pH 7.0 and analysed after boiling by SDS-PAGE with Coomassie staining. Unreactive control proteins, SpyCatcher002 EQ and SpyTag002 DA-MBP were also shown; and (B) a graph of a time-course for reaction of SpyCatcher002-sfGFP with SpyTag002-MBP or reaction of SpyCatcher-sfGFP with SpyTag-MBP at 0.1 μM in succinate-phosphate-glycine buffer at pH 7.0. (mean of triplicate ±1 s.d.; some error bars are too small to be visible).

FIG. 10 shows graphs of time-courses for reaction of SpyCatcher002-sfGFP with SpyTag002-MBP or reaction of SpyCatcher-sfGFP with SpyTag-MBP at (A) 1 μM and (B) 10 μM in succinate-phosphate-glycine buffer at pH 7.0. (mean of triplicate ±1 s.d.; some error bars are too small to be visible) (B).

FIG. 15 shows graphs depicting a time course for 0.5 μM D5T SpyCatcher002 (SEQ ID NO: 40) reacting with (A) 0.5 μM SpyTag002-MBP (SEQ ID NO: 3-MBP) or SpyTag002 T3H-MBP (SEQ ID NO: 4-MBP); and (B) 0.5 μM SpyTag002-T3H-MBP (SEQ ID NO: 4-MBP) or SpyTag002 RG T3H-MBP (SEQ ID NO: 5-MBP). The reaction was performed in Phosphate Buffered Saline (PBS) pH 7.5 at 25° C. and analysed by SDS-PAGE and Coomassie staining with the data showing the mean of reactions carried out in triplicate ±1 s.d. The equations for the trend-line and the correlation coefficient are shown. The second-order rate constants for the reactions come from the slopes of the trend-lines and have units of $\mu M^{-1}$ $min^{-1}$.

EXAMPLES

Example 1—Phage Display Optimization of SpyTaq (SEQ ID NO: 6)

The SpyTag/SpyCatcher is an unconventional approach to peptide interactions and there are features of the interaction that cannot be predicted by rational design. Selection from phage libraries has been established for decades and the difficult thing is usually to detect weak interactions, rather than the challenge of screening for irreversible interactions. We initially established a model selection to work out efficient selection for isopeptide bond formation.

The first key feature we found to enable successful panning of SpyTag-phage was to capture SpyCatcher (SEQ ID NO: 7) bait in solution, rather than attaching SpyCatcher to a bead. Solution-capture allowed easy titration of bait concentration and reduced the background from non-specific binding of phage to beads (FIG. 1).

Figure 1:
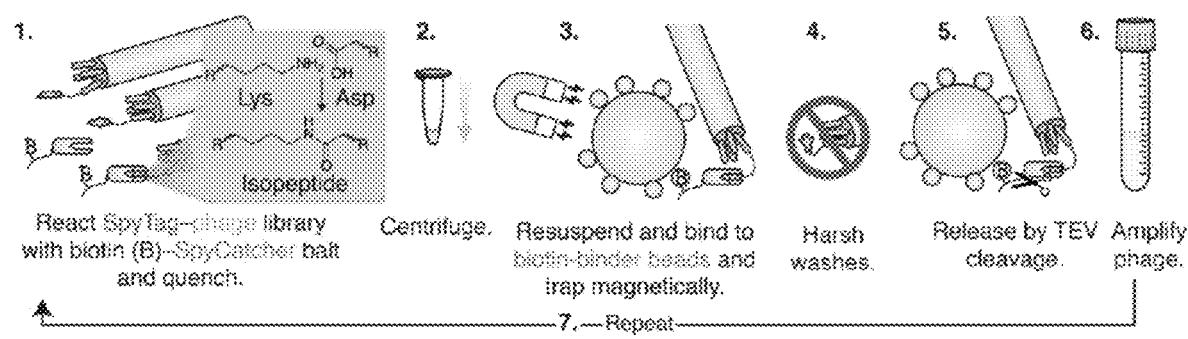
FIG. 1 shows a cartoon of the panning procedure to select for SpyTag variants displayed on pill of M13 phage.

The second key feature was the use of protease cleavage to elute the phage specifically from the streptavidin-beads, via a TEV protease site between the biotin and SpyCatcher (FIG. 1).

The third key feature was establishing conditions harsh enough to dissociate nearly all non-covalent interactions by the phage-peptide variant, but not so harsh that the phage infectivity was destroyed. We settled on the use of one wash with glycine-HCl pH 2.2, then four washes with 0.5% (v/v) Tween-20.

For the model selection we used M13 phage displaying SpyTag on pIII. The bait was site-specifically biotinylated through an AviTag, linked either to SpyCatcher or the negative control SpyCatcher EQ with a mutation in the glutamic acid essential for covalent bond formation. After precipitation to remove excess bait, streptavidin-bead capture, washing and TEV elution, recovered phage was measured by quantitative PCR (qPCR) detection of the DNA packaged in the phage. After our optimisation of panning conditions, this test showed 4 orders of magnitude enrichment for wt SpyCatcher over SpyCatcher EQ (FIG. 2A).

Figure 3:
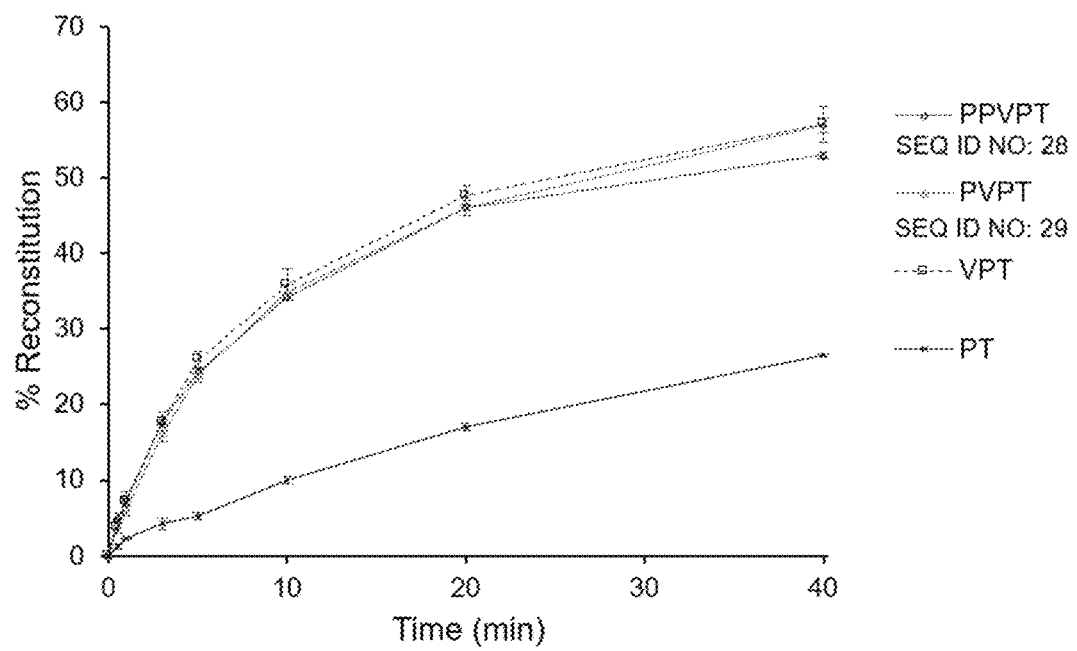
FIG. 3 shows a graph of the time-course of SpyCatcher reacting with deletion variants of the SpyTag N-terminal library's most reactive variant (NLib1-MBP). PPVPT refers to SEQ ID NO: 15, PVPT refers to SEQ ID NO: 30, VPT refers to SEQ ID NO: 31, and PT refers to SEQ ID NO: 32. The data show the mean of reactions carried out in triplicate ±1 s.d.; some error bars are too small to be visible.

Previous site-directed mutagenesis had shown a key role for the central β-strand residues in SpyTag, so we made two different libraries randomising residues at the N-terminal and C-terminal ends of SpyTag (FIG. 2B). With N-terminal randomisation and rounds of phage panning, NLib1 (PPVP-TIVMVDAYKPTK, SEQ ID NO:15) gave the fastest reaction. NLib1 was 3 residues longer than the parent SpyTag, so we tested how many of the extra N-terminal residues were important. NLib1 could be truncated at the N-terminus by two residues with little effect on rate, but truncation of the 3$^{rd}$ residue greatly reduced reaction (FIG. 3). Therefore VPT—was used thereafter at the N-terminus, while the C-terminus was randomised based on this lead. After rounds of phage library screening, the enriched hits CLib1-10 are shown (FIG. 2B). Of these variants, CLib1 was fastest for reaction with SpyCatcher and interestingly preserved the C-terminal YK sequence in SpyTag. However, the cysteine in CLib1 was undesirable because of the potential for dimerisation and so this residue was reverted to A (FIG. 2B). In addition we found that the terminal K of SpyTag (not present in the phage library) increased reaction rate. Therefore with this combination of phage selection and rational design, we arrived at an optimised tag, SpyTag002 (VP-TIVMVDAYKRYK, SEQ ID NO: 3) (FIG. 2B).

Example 2—Phage Display Optimisation of SpyCatcher (SEQ ID NO: 7)

Phage display selection of SpyCatcher was performed similarly to selection of SpyTag variants, although display of a split protein on the surface of phage provides a further challenge. Key features we found important for efficient selection were a TEV protease cleavage site between SpyCatcher and pIII on the phage (allowing specific elution of phage from the magnetic beads) and the use of a DsbA signal sequence for cotranslational translocation, which improved the display of SpyCatcher on pIII. The bait was biotinylated AviTag-SpyTag-MBP and SpyCatcher variants were made by error-prone PCR (FIG. 4A). We initially optimised a model selection with the desired bait (SpyTag) or a negative control, SpyTag DA, which binds non-covalently to SpyCatcher but does not react. This selection showed ~1,000-fold enhanced capture of wt SpyTag bait compared to SpyTag DA bait, as assessed by qPCR of recovered phage (FIG. 4B).

Figure 6:
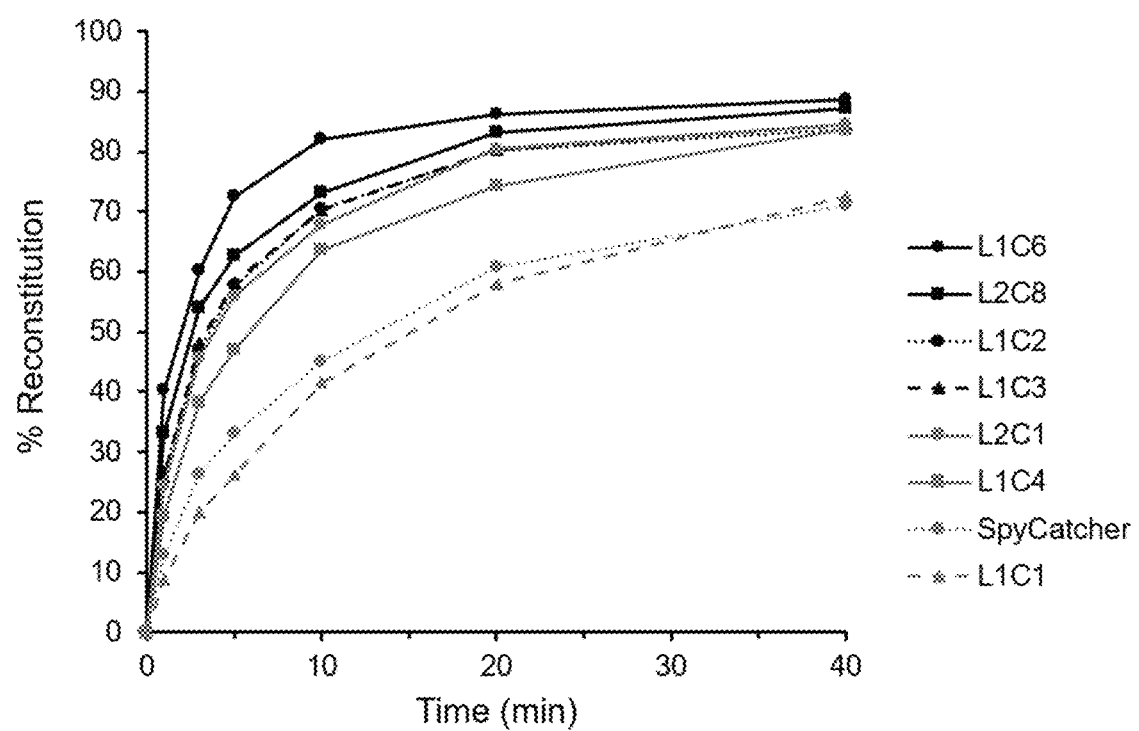
FIG. 6 shows a graph of reaction time-courses of phage-selected SpyCatcher variants. SpyTag-MBP was incubated with SpyCatcher and selected variants, with each protein at 1 μM at 25° C. in PBS pH 7.5. Reaction was analysed after boiling by SDS-PAGE with Coomassie staining. The data show the means of replicate reactions. SpyCatcher refers to SEQ ID NO: 7, L1C1 refers to SEQ ID NO:33, L1C4 refers to SEQ ID NO:34, L1C2 refers to SEQ ID NO:35, L2C1 refers to SEQ ID NO:36, L1C3 refers to SEQ ID NO:37, L1C6 refers to SEQ ID NO:38, and L2C8 refers to SEQ ID NO:39.

After rounds of panning with increasing stringency, the sequence of selected clones is indicated in FIG. 5. Mutations were widely distributed over the structure, with many mutated residues distant from the SpyTag binding site. Hits were expressed as soluble proteins in E. coli and evaluated for their speed of reaction with SpyTag-MBP. The best reacting sequence was L1C6 (FIG. 6).

Figure 7:
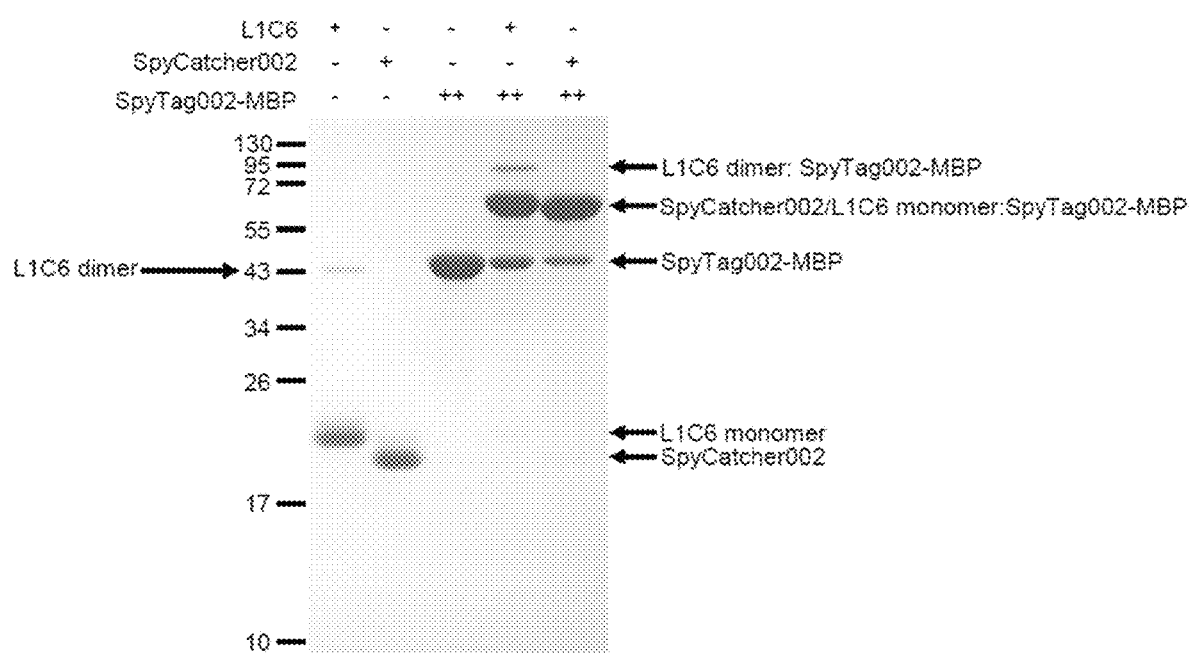
FIG. 7 shows (A) an SDS-PAGE gel showing that the self-reaction of L1C6 SpyCatcher variant was blocked in SpyCatcher002. L1C6 and SpyCatcher002 were analysed in isolation or after reaction with SpyTag002-MBP by SDS-PAGE with Coomassie staining. A small fraction of covalent L1C6 dimer is marked, as well as the product from L1C6 dimer reacting with SpyTag002-MBP. Reaction conditions: 10 μM (+) SpyCatcher variant, 13 μM (++) SpyTag002-MBP, PBS pH 7.5 at 25° C. for 1 h; and (B) an alignment of part of the amino acid sequence of SpyTag (SEQ ID NO:41) with the N-terminus of SpyCatcher L1C6 (SEQ ID NO:42). The N-terminus of L1C6 D5T (SEQ ID NO:43) prevented self-reaction.

During this process, a new band was identified on SDS-PAGE after recombinant expression of the L1C6 SpyCatcher variant (FIG. 7A). Since this band completely shifted upon mixing with SpyTag002-MBP and had a mobility approximately twice that of SpyCatcher, we were confident that the band represented a covalent SpyCatcher dimer. It was hypothesised that enhancing SpyCatcher reactivity had promoted the formation of this unintended self-reactivity. Looking in SpyCatcher for a sequence with similarly to SpyTag, we found the N-terminal GAMVDT (SEQ ID NO:42) of SpyCatcher resembled IVMVDA (SEQ ID NO:41) of SpyTag (FIG. 7B). We were pleased to see that mutating GAMVDT (SEQ ID NO:42) to GAMVTT (SEQ ID NO:43) in our accelerated variant (SpyCatcher002, FIG. 5) removed this side-reaction (FIG. 7A).

Figure 8:
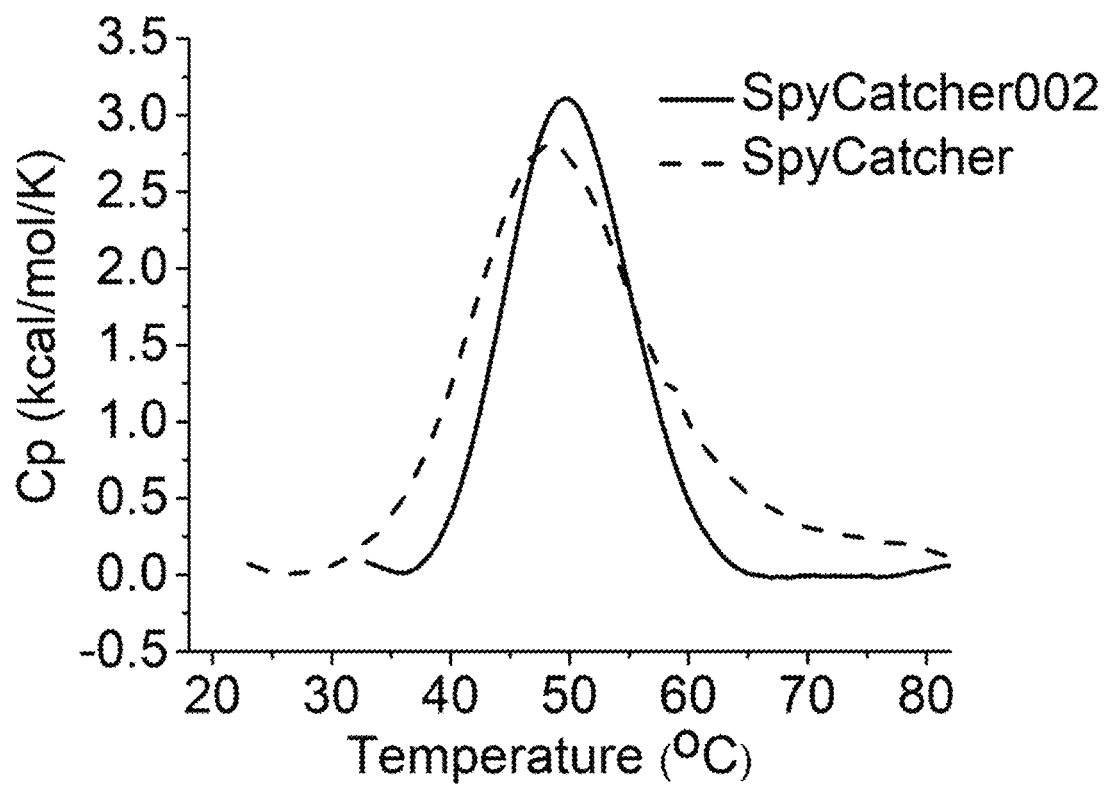
FIG. 8 shows a graph presenting differential scanning calorimetry of SpyCatcher overlaid with SpyCatcher002. Tm values are shown inset.

To explore the effect of the mutations on SpyCatcher folding, we tested the constructs by Differential Scanning Calorimetry (DSC). DSC showed that there was minimal change in the unfolding transition point between SpyCatcher (49.3° C.) and SpyCatcher002 (49.9° C.), so the mutagenesis had not damaged thermostability (FIG. 8).

Example 3—Validation of SpyTag002 and SpyCatcher002 Variant Rates

With SpyTag002 and SpyCatcher002 in hand, we carefully validated their reaction behaviour with each other. We confirmed the key role of putative reactive residues, by showing that single mutation in SpyTag002 (DA) or in SpyCatcher002 (EQ) abolished reaction (FIG. 9A).

Figure 11:
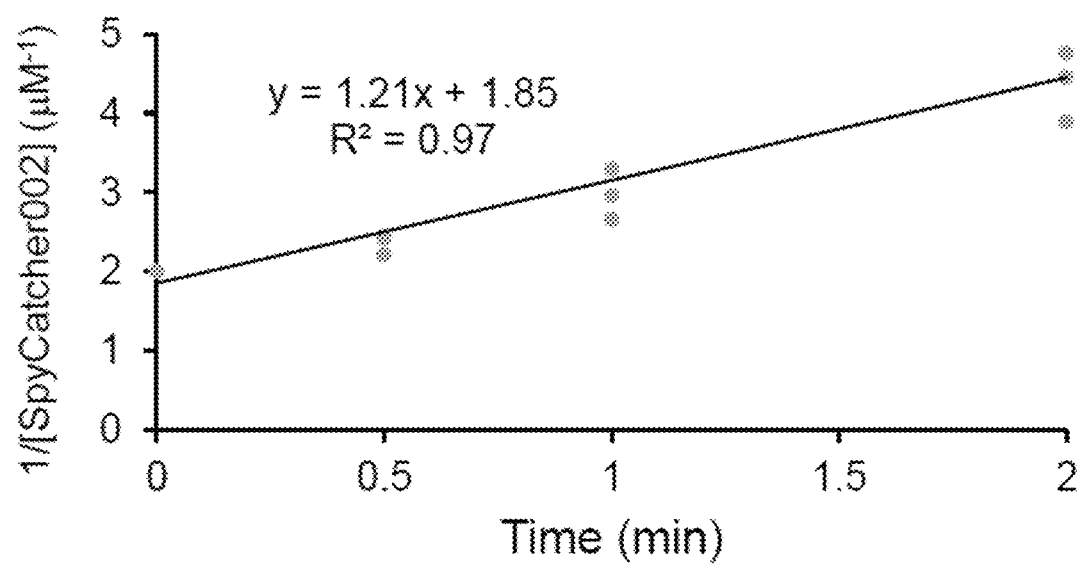
FIG. 11 shows a graph quantifying the rate constant for SpyCatcher002 reacting with SpyTag002-MBP, from triplicate measurements (each data-point shown). 0.5 μM of each protein was in succinate-phosphate-glycine buffer at pH 7.0, 25° C. The equation for the trend-line and the correlation coefficient are shown.

The SpyTag/SpyCatcher reaction is efficient at high concentrations. To analyse the reaction at low concentrations, we reacted with superfolder GFP (sfGFP) for fluorescent detection of covalent bond formation, after polyacrylamide electrophoresis. If samples are not boiled, sfGFP can remain folded and fluorescent even in the presence of SDS. This analysis showed the major enhancement of reaction rate with SpyTag002 and SpyCatcher002 compared to the parental versions (FIG. 9B). As expected, the difference was less marked as the concentrations of both partners increased to 1 μM and 10 μM, but the 002 versions were still faster at 10 μM (FIGS. 10A and B). The reaction rate was well fit to a second order reaction (FIG. 11). At 25° C. at pH 7.0, SpyTag002-MBP reacted with SpyCatcher002 with a rate constant of $2.0 \pm 0.2 \times 10^4 M^{-1} \cdot s^{-1}$ (12 times faster than SpyTag-MBP reacting with SpyCatcher). SpyTag002 and SpyCatcher002 both showed backwards-compatibility, reacting efficient with the parental versions (Table 2).

TABLE 2

Rate constants for the reactions of SpyCatcher or SpyCatcher002 with SpyTag-MBP or SpyTag002-MBP in succinate-phosphate-glycine buffer pH 7.0 at 25° C. (mean ± 1 s.d., n = 3).

| Rate constant ($M^{-1} \cdot s^{-1}$) | SpyTag-MBP | SpyTag002-MBP |
|---|---|---|
| SpyCatcher | 1,680 ± 440 | 10,300 ± 640 |
| SpyCatcher002 | 5,470 ± 30 | 20,220 ± 1,760 |

Figure 12:
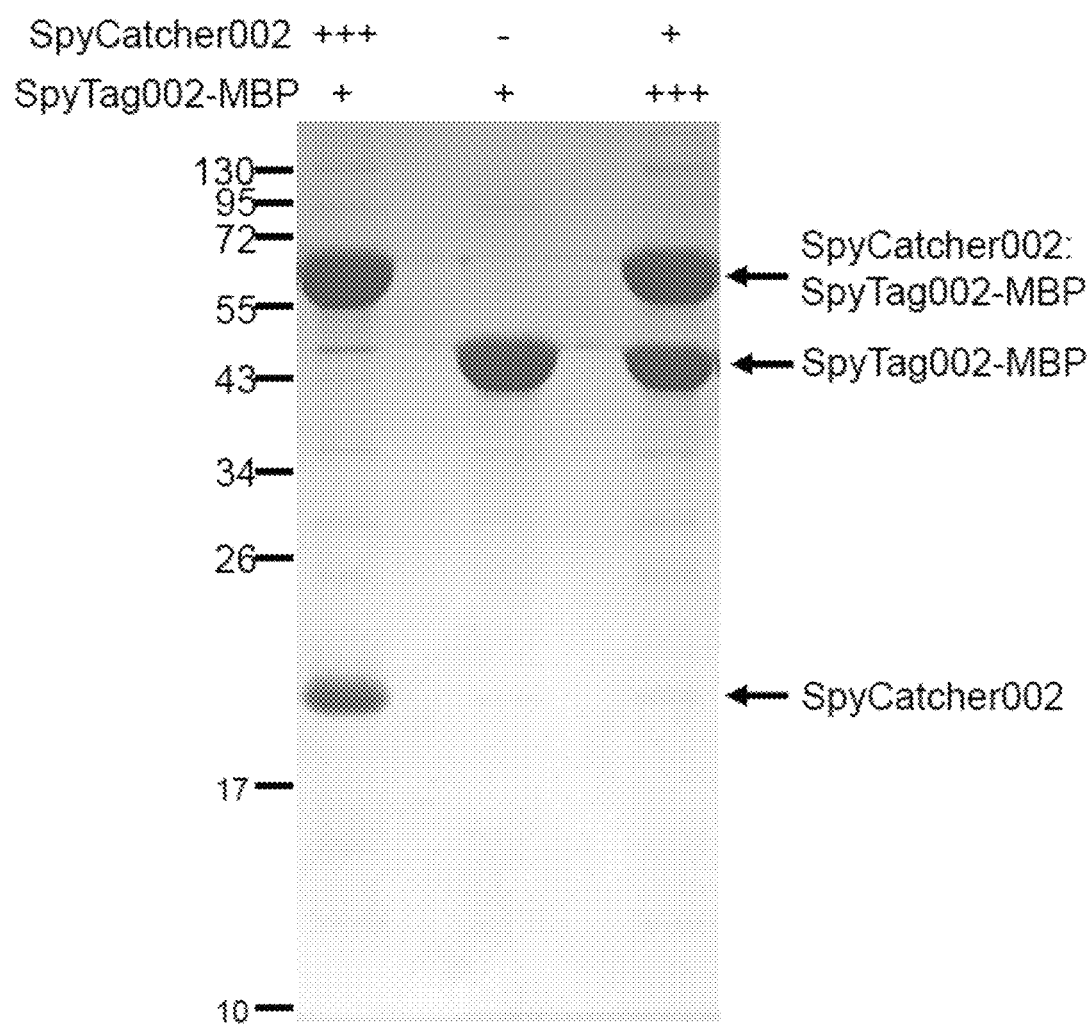
FIG. 12 shows an SDS-PAGE gel depicting the test of the reaction of SpyCatcher002/SpyTag002 to completion. SpyCatcher002 was incubated with SpyTag002-MBP in succinate-phosphate-glycine buffer pH 7.0 for 1 h at 25° C. before analysis by SDS-PAGE and Coomassie staining. Proteins were at 10 μM (+) or 20 μM (+++).

The SpyTag system has low intrinsic reactivity of the reactive groups (amine and carboxylic acid) and so has reduced chance of side-reactions, such as hydrolysis of esters or thioesters. Near quantitative yield is especially important with multiple sequential reactions, such as in solid-phase polyproteam synthesis or for clinical development, where uniformity is important. With two-fold excess of their partner, in 1 hour >99% SpyCatcher002 and >97% SpyTag002-MBP reacted (FIG. 12).

The isopeptide bond formation between SpyTag002 and SpyCatcher002 was also confirmed by electrospray ionization mass spectrometry, with the expected loss of $H_2O$ upon reaction.

Example 4—Validation of SpyTag002 and SpyCatcher002 Variant Reaction Conditions

Figure 13:
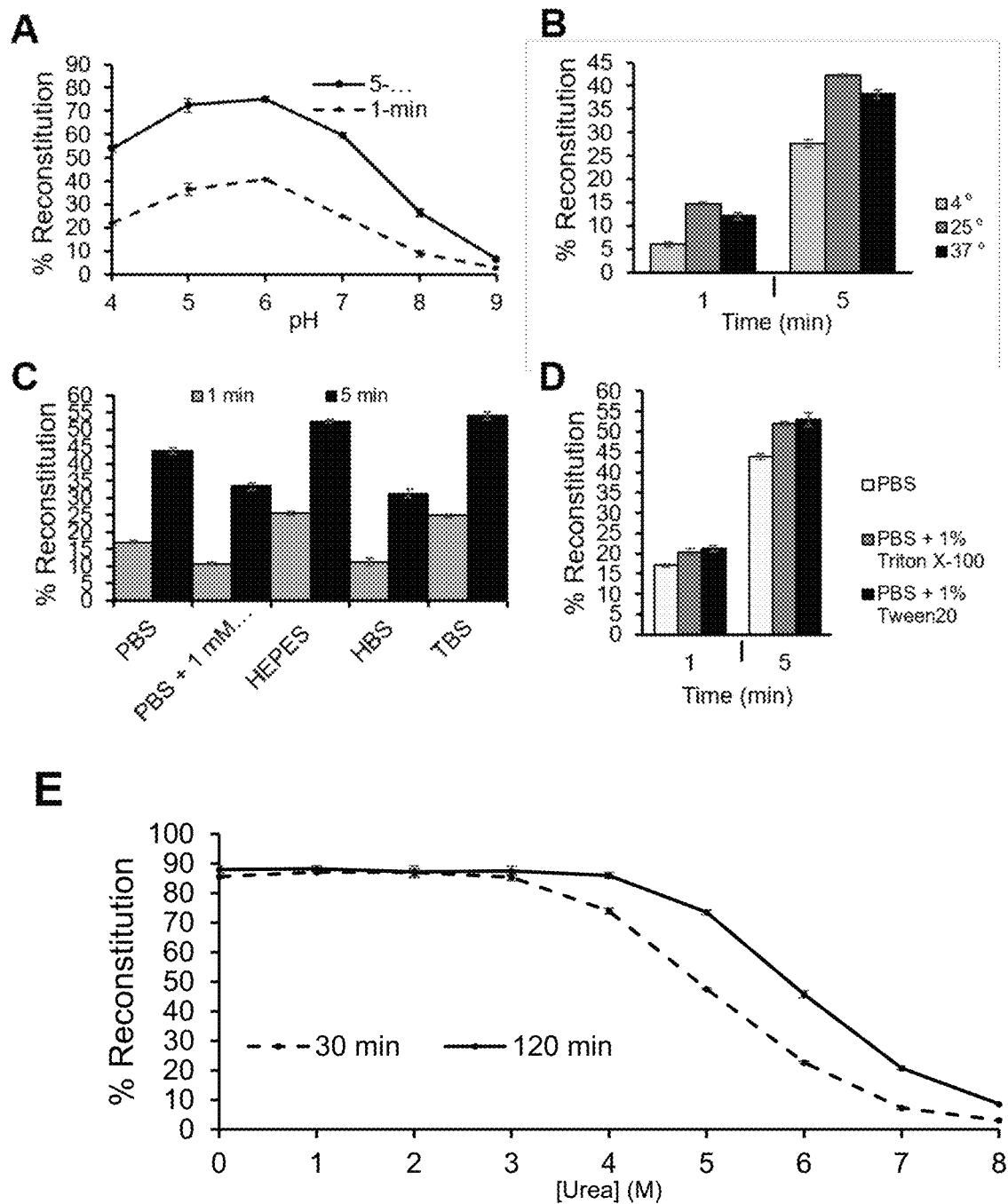
FIG. 13 shows (A) a graph depicting the pH-dependence of reaction of SpyCatcher002 with SpyTag002-MBP for 1 or 5 min at 25° C. in succinate-phosphate-glycine buffer, analysed by SDS-PAGE and Coomassie staining; (B) a bar-chart showing the temperature-dependence of reaction as in (A) in PBS pH 7.5; (C) a bar chart showing the buffer-dependence of reaction as in (A) at 25° C. and pH 7.5 with PBS, PBS+1 mM EDTA, 50 mM HEPES, 50 mM HEPES-buffered saline (HBS), or Tris-buffered saline (TBS); (D) a bar chart showing the detergent-dependence of reaction as in (A) in PBS pH 7.5 at 25° C. with no detergent (PBS), PBS with 1% Triton X-100, or PBS with 1% Tween-20; and (E) a graph depicting urea dependence of the reaction of SpyCatcher002 with SpyTag002-MBP at 25° C. and pH 7.5 in PBS for 30 or 120 min. All graphs show the mean of triplicate ±1 s.d.; some error bars are too small to be visible.

We tested the resilience of the reaction of SpyTag002 and SpyCatcher002 under a wide range of conditions. The above rate constants were calculated at pH 7, but reactivity was similar at pH 4 and slightly higher at pH 5 and 6 (FIG. 13A). Reaction was fast at 4, 25 and 37° C. (FIG. 13B). Reaction was relatively independent of buffer, with efficient reaction with phosphate, Tris or HEPES buffering, with relatively little dependence on specific monovalent or divalent anions or cations (FIG. 13C). Reaction of SpyTag002 and SpyCatcher002 tolerated well the presence of detergents Triton X-100 or Tween-20, giving a slight enhancement of reactivity (FIG. 13D). Reaction of SpyTag002 and SpyCatcher002 also tolerated over 3M urea (FIG. 13E).

Figure 14:
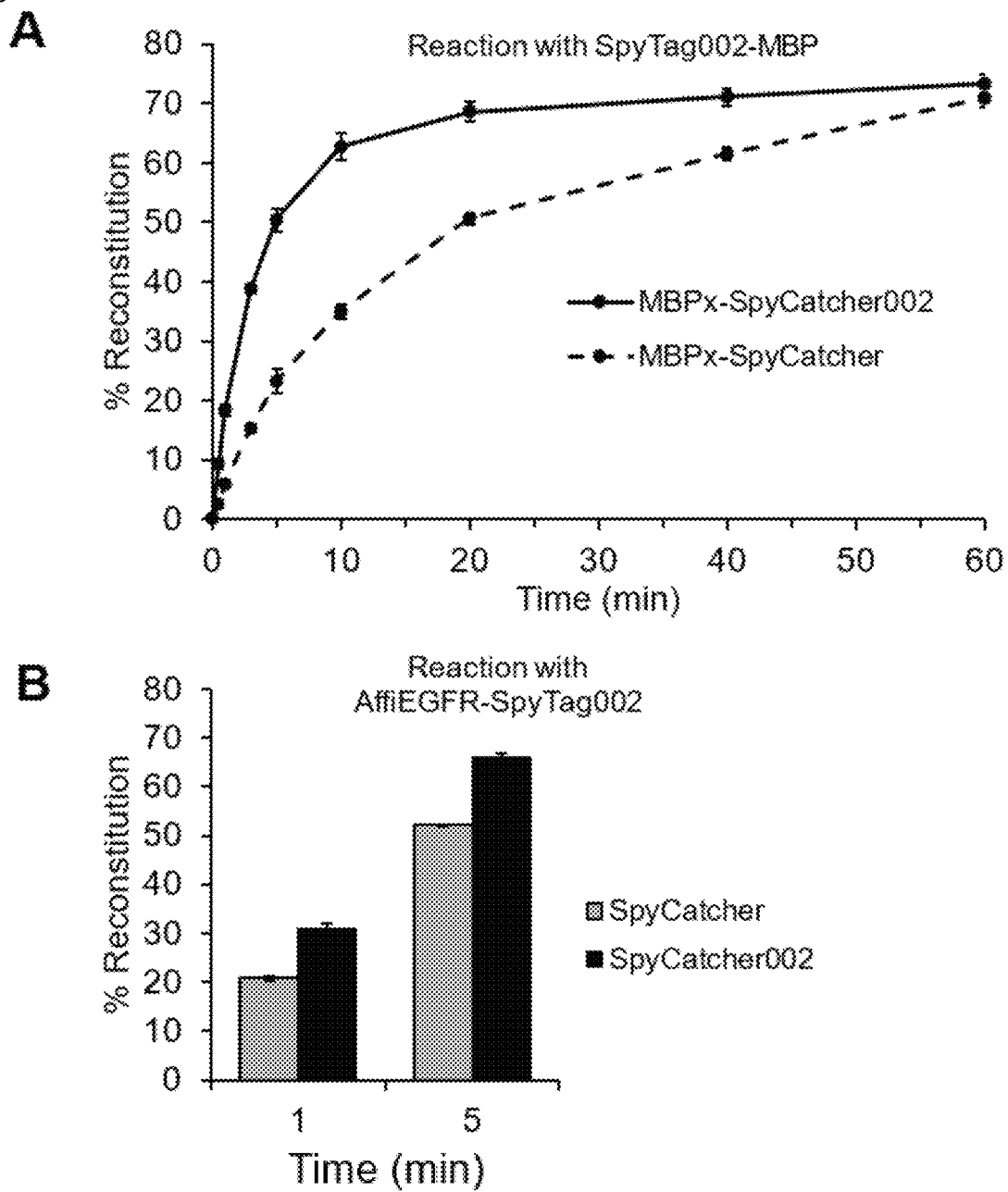
FIG. 14 shows (A) a graph showing a time-course of MBPx-SpyCatcher and MBPx-SpyCatcher002 reacting with SpyTag002-MBP, with each protein at 0.5 μM at 25° C. in PBS pH 7.5, analysed after boiling by SDS-PAGE with Coomassie staining and demonstrates that the improved reactivity of SpyCatcher002 over SpyCatcher was retained when a protein was fused to the N-terminus; and (B) a bar chart of the reactivity of AffiEGFR-SpyTag002 incubated with SpyCatcher or SpyCatcher002 for 1 or 5 min, with each protein at 2 μM at 25° C. in PBS pH 7.5 and analysed by SDS-PAGE with Coomassie staining. Data show the mean of reactions carried out in triplicate ±1 s.d.; some error bars are too small to be visible. This shows that the improved reactivity of SpyCatcher002 over SpyCatcher was retained when SpyTag002 was at the C-terminus.

SpyCatcher002 was selected on phage as an N-terminal fusion to pIII. We confirmed that SpyCatcher002 also behaved well as a C-terminal fusion, showing efficient reaction of MBPx-SpyCatcher002 with SpyTag002-MBP (FIG. 14A). We validated that SpyTag002 reacted efficiently when fused at the N-terminus as SpyTag002-MBP (FIG. 12) or at the C-terminus as AffiEGFR-SpyTag002 (FIG. 14B).

Example 5—Further Optimisation of SpyTag002

The SpyTag002-MBP fusion has a reaction rate of 0.40 $\mu M^{-1}$ $min^{-1}$ with SpyCatcher002. We surprisingly determined that the reaction rate could be further improved by introducing additional modifications to the SpyTag002 peptide.

Substitution of the threonine residue at position 3 of SpyTag002 (SEQ ID NO: 3) with histidine, i.e. reversion to the residue at the equivalent position in SpyTag, resulted in a peptide (SEQ ID NO: 4) with a reaction rate of 0.53-0.55 $\mu M^{-1}$ $min^{-1}$, i.e. about a 35% increase in activity (FIG. 15A).

Modification of the improved peptide to include arginine and glycine residues at the N-terminus (SEQ ID NO: 5) more than doubled the reaction rate to 1.21 $\mu M^{-1}$ $min^{-1}$ (FIG. 15B).

Example 6—Further Optimisation of SpyCatcher002

A variant of SpyCatcher002 containing an alanine residue at position 5 (SpyCatcher002D5A SEQ ID NO:44) has a reaction rate of 0.45 $\mu M^{-1}$ $min^{-1}$ with SpyTag002-MBP. We surprisingly determined that the reaction rate could be further improved by introducing additional modifications to the SpyCatcher002 polypeptide.

Figure 16:
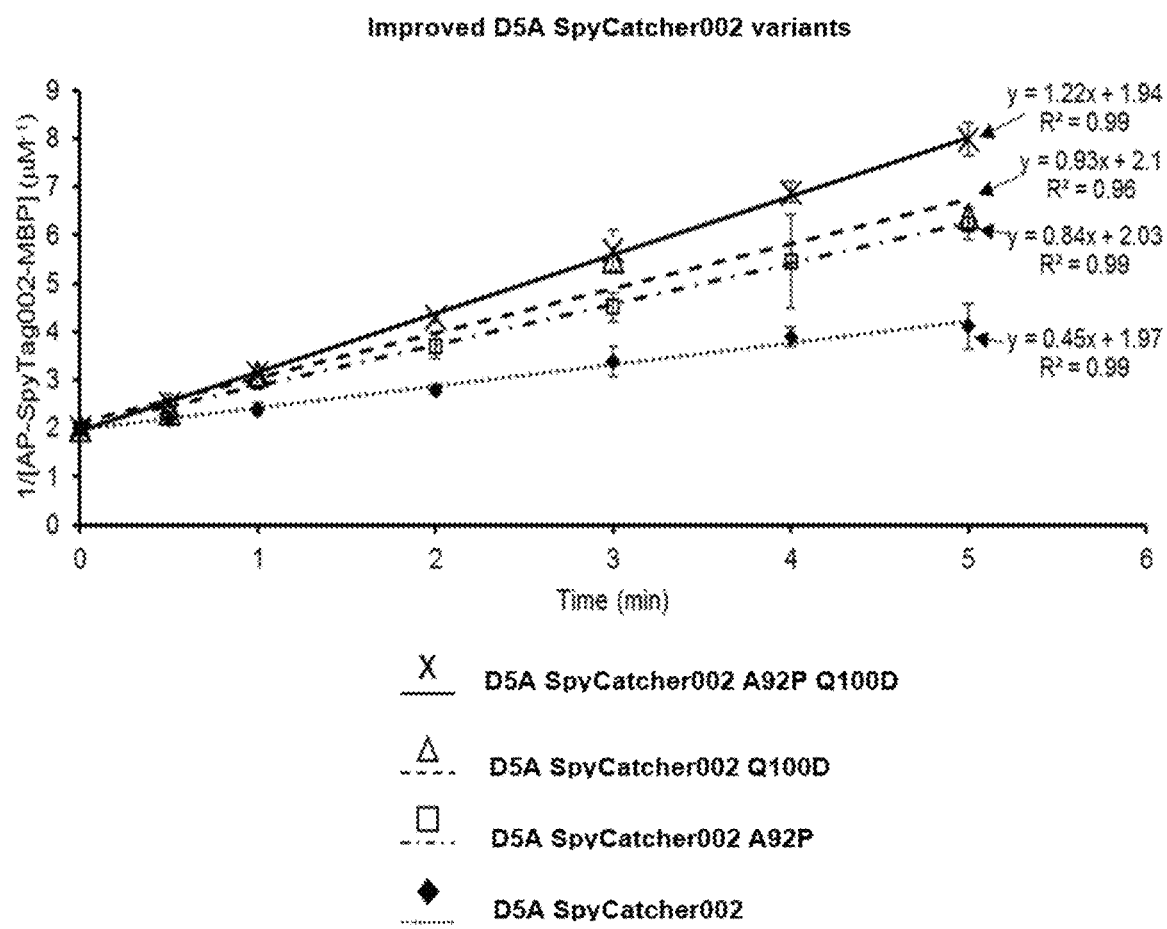
FIG. 16 shows a graph depicting the rate analysis for 0.5 μM D5A SpyCatcher002 variants (SEQ ID NOs: 44-47) reacting with 0.5 μM AP-SpyTag002-MBP (SEQ ID NO: 3-MBP) in Phosphate Buffered Saline (PBS) pH 7.5 at 25° C. All reactions were analysed by SDS-PAGE and Coomassie staining with the data showing the mean of reactions carried out in triplicate ±1 s.d. The equations for the trend-line and the correlation coefficient are shown. The second-order rate constants for the reactions come from the slopes of the trend-lines and have units of $\mu M^{-1}$ $min^{-1}$.

Substitution of the alanine residue at position 92 of the SpyCatcher002 variant (SEQ ID NO:44) with proline resulted in a polypeptide (peptide tag binding partner, SEQ ID NO:45) with a reaction rate of 0.84 $\mu M^{-1}$ $min^{-1}$, i.e. about an 85% increase in activity (FIG. 16).

Whilst not wishing to be bound by theory, it is postulated that the insertion of a proline residue at this position in the polypeptide reduces the flexibility in a loop of the polypeptide. In this respect, the phi angle of proline is fixed, whereas the phi angle of all other residues can vary substantially. Here we found that Ala had a suitable phi angle for replacement by proline and also judged that the increased side-chain size of proline would be sterically tolerated. Based on our work on crystallography of the SpyTag/SpyCatcher interaction, we also thought that this loop of SpyCatcher would be especially important for the interaction, because of the proximity of SpyTag. Therefore we hypothesised that this mutation would make the SpyCatcher variant conformation pre-oriented for SpyTag docking, thereby increasing reaction rate.

Similarly, substitution of the glutamine residue at position 100 of the SpyCatcher002 variant (SpyCatcher002D5A SEQ ID NO:44) with aspartic acid resulted in a polypeptide (peptide tag binding partner, SEQ ID NO:46) with a reaction rate of 0.93 $\mu M^{-1}$ $min^{-1}$, i.e. about a 105% increase in activity (FIG. 16). It is thought that the Aspartic acid at this position may form an electrostatic interaction with Lysine 111, so increasing the stability of interaction between two loops of the SpyCatcher variant. We hypothesised that this mutation would make the SpyCatcher conformation pre-oriented for SpyTag docking, thereby increasing reaction rate.

Combining the substitutions described above (SEQ ID NO:47) further improved the reaction rate to 1.22 $\mu M^{-1}$ $min^{-1}$, thereby showing that each mutation has a separate effect on the reaction rate. Notably, substitution of the alanine at position 5 of SEQ ID NO: 47 with threonine (i.e. resulting in SEQ ID NO: 2) further improves the reaction rate (FIG. 16).

METHODS

Cloning

Q5 High-Fidelity Polymerase (NEB) was used to perform all PCRs and site-directed mutagenesis. Gibson Assembly Master Mix (NEB) was used following the manufacturer's instructions. All constructs were initially cloned into chemically competent E. coli NEB5α cells (NEB).

Plasmids pET28a SpyTag-MBP (Addgene plasmid ID 35050), pET28A SpyTag-DA-MBP, pDEST14 SpyCatcher (GenBank JQ478411, Addgene plasmid ID 35044), and pDEST14 SpyCatcher EQ (Addgene plasmid ID 35045) have been described previously (Zakeri et al., 2012, Proc Natl Acad Sci USA 109, E690-697). pDEST14 AP-SpyCatcher (GenBank accession no. KU500645, Addgene plasmid ID 72326) both as WT and EQ versions, containing a peptide tag (AP) for site specific biotinylation at the N-terminus, was constructed from pDEST14 SpyCatcher (WT/EQ) using SLIM PCR using primers 5'-GATTACGA-CATCCCAACGACCGAAAACCTG (SEQ ID NO:48), 5'-GCCTGAACGATATTTTTGAAGCGCAGAAAATT-GAATGGCATGAAGGCGATTAC GACATCC-CAACGACCGAAAACCTG (SEQ ID NO:49), 5'-GT-GATGGTGATGGTGATGGTAGTACGACATATG (SEQ ID NO:50) and 5'-TGCCATTCAATTTTCTGCGCTT-CAAAAATATCGTTCAGGCCGCTGCCGTGATG GTGATGGTGATGGTAGTACGACATATG (SEQ ID NO:51). pET28a AP-SpyTag-MBP and AP-SpyTag DA-MBP were constructed by inserting the same biotinylation tag N-terminal (but without the TEV protease cleavage site) into pET28a SpyTag(WT/DA)-MBP using 5'-ATTA-CATATGGGTCTGAATGATATTTT CGAAGCGCAGAAAATTGAATGGCAT-GAAGGTAGCGGAGCCCACATCGTGATG GTG (SEQ ID NO:52) and 5'-GGGGAAGCTTT-TACGAGCTCGAATTAGTCTG (SEQ ID NO:53). The insert was digested with HindIII (NEB) and NdeI (NEB) and ligated into pET28a.

Individual SpyTag variants (including SpyTag002 DA-MBP) were created using QuikChange PCR with pET28a SpyTag-MBP as template and transformed in to NEB5α cells. Individual SpyCatcher variants were cloned from the pFab5cHis phagemid vector in to pDEST14 for the expression of soluble protein by PCR amplification of the SpyCatcher gene using forward (5'-CCGAAAACCTGTATTTT CAGGGCGCCATG (SEQ ID NO:54)) and reverse (5'-GCATCAACCATTTAGCTACCACTGGATCC (SEQ ID NO:55)) primers. The reverse primer retains the GSGGS peptide linker of pFab5cHis that comes C-terminal to the SpyCatcher protein to allow subsequent overlap with the pDEST14 vector. Additional point mutations in selected SpyCatcher variants (including the SpyCatcher002 EQ inactive version) were introduced by QuikChange PCR mutagenesis. All mutations and constructs were verified by sequencing.

Plasmid pJ404-SpyCatcher-sfGFP encoding SpyCatcher fused to superfolder GFP (sfGFP) was a kind gift from Karl Brune (University of Oxford) and was produced in a three-part Gibson Assembly. The SpyCatcher gene (including the His-tag and TEV protease cleavage site) was amplified from the pDEST14 SpyCatcher plasmid using forward (5'-GTT-TAACTTTAATAAGGAGATA TACCATGTCGTACTAC-CATCACCATCACC (SEQ ID NO:56)) and reverse (5'-CTTTACGGCCTGAACCACCAATATGAGCGTCACCTT-TAGTTGC (SEQ ID NO:57)) primers. The sfGFP preceded by a GGSG linker was amplified with forward (5'-GGTGGTTCAGGCCGTAAAGG (SEQ ID NO:58)) and reverse (5'-CCTTGGGGCTCGAGTTATCATTTGTA-CAGTTCATCCATACCATGC (SEQ ID NO:59)) primers from the pJ404-sfGFP plasmid (DNA2.0). The plasmid backbone was amplified using forward (5'-CATGGTATATCTCCTTATTAAAGTTAAACAAAATTAT-TTCTACAGGG (SEQ ID NO:60)) and reverse (5'-TGA-TAACTCGAGCCCCAAGG (SEQ ID NO:61)) primers. The three PCR products were then linked by Gibson Assembly. Plasmid pJ404-SpyCatcher002-sfGFP was created by amplifying the SpyCatcher002 gene from pDEST14-SpyCatcher002 using forward (5'-CATGGTATATCTCCTTAT-TAAAGTTAAACAAAATTATTTCTACAGGG(SEQ ID NO:62)) and reverse (5'-TGATAACTCGAGCCCCAAGG (SEQ ID NO:63)) primers. The vector backbone was amplified in two parts using four primers (5'-GGTGGTTCAGGCCGTAAAGGCGAAGAGCTG (SEQ ID NO:64); 5'-CGCGATTTGCTGGTGACC-CAATGCGACCAGATGCTCCACGCCCAGTCGCGTA CCGTCCTC (SEQ ID NO:65); 5'-GCCCTGAAAATA-CAGGTTTTCGGTCGTTGGG (SEQ ID NO:66); and 5'-GAGGACGGTACGCGACTGGGCGTGGAG-CATCTGGTCGCATTGGGTCAC CAGCAAATCGCG (SEQ ID NO:67)) and Gibson Assembled to produce the final construct.

pET21 MBPx-SpyCatcher (N-terminal His6 tag-MBPmt-spacer-MBPmt-spacer-SpyCatcher) (GenBank accession no. KU361183, Addgene plasmid ID 72327) was previously described (Veggiani et al., 2016 Proc Natl Acad Sci USA 113, 1202-1207). pET21 MBPx-SpyCatcher002 was generated via a 3-part Gibson assembly. SpyCatcher002 was amplified from pDEST14-SpyCatcher002 using forward (5'-CGAGCTCGGGTTCGGGCGGTAGTGGTGCC ATGGTAACCACCTTATCAGGTTTATCAGGTG (SEQ ID NO:68)) and reverse (5'-GTGGTGGTGCTCGAGTG CGGCCGCAAGCTTCTATTAAGTATGAGCGT-CACCTTTAGTTGC (SEQ ID NO:69)) primers. The template backbone was generated in two parts from the plasmid pET21 MBPx-SpyCatcher using four primers (5'-GGTTTCGCCACCTCTGACTTGAGCGTCG (SEQ ID NO:70); 5'-CATGGCACCAC-TACCGCCCGAACCCGAGCTCG (SEQ ID NO:71), 5'-AAGCTTGCGGCCGCACTCGAGCACCACCAC-CACCACCACTGAGATCCGGC (SEQ ID NO:72); 5'-CGACGCTCAAGTCAGAGGTGGCGAAACC (SEQ ID NO:73)) and Gibson Assembled to yield the final product.

pET28a AffiEGFR-SpyTag002 was generated via a 2-part Gibson assembly using four primers (5'-GGCAGCATT-GAATTTATTAAAGTGAACAAAGGCAGTGGT-GAGTCG GGATCCGGAGCTAGC (SEQ ID NO:74); 5'-GTTTATTATTTATAGCGTTTGTAGGCGTCCACCAT-AACAATAG TAGGAACACCGGAACCTTCCCCG-GATCCCTCGAGGCC (SEQ ID NO:75); 5'-GGACGCC-TACAAACGCTATA AATAATAAACTCTAGCACCACT-GAGATCCGGCTGCTAAC (SEQ ID NO:76); 5'-ACTGCCTTTGTTCACTTTA ATAAATT-CAATGCTGCCCAGTTTCCCCATATGGCTGCCGCG (SEQ ID NO:77)) using plasmid pET28a SnoopTag-AffiEGFR-SpyTag (GenBank accession no. KU296973) as the template.

pET28a His-MBP was created by cloning the maltose binding protein gene from the pMAL vector (NEB) in to the pET28a vector as previously described by Zakeri et al (2012, supra).

pRK793 encoding MBP-Hiss-TEV protease containing an S219V mutation to reduce the rate of autolysis and was further modified to prevent self-cleavage of the TEV protease from the MBP by mutation of the TEV recognition site to inhibit cleavage.

The phagemid plasmid was a variant of pFab5c.His which encodes a PelB leader sequence, a cloning site and only the part of gene III encoding the final C-terminal domain of the M13 phage pIII. The SpyTag phagemid plasmid (pFab5cHis-PelB-SpyTag-gIII) was created by inserting DNA encoding SpyTag between the PelB leader and gIII. The pFab5cHis plasmid was digested with XhoI (NEB) and NotI (NEB). Primers 5'-TCGAGGGCGGCGCCCACATCGT-GATGGTGGACGCCTACAAGCCGACG AAGGGCGC (SEQ ID NO:78) and 5'-GGCCGCCTTCGTCGGCTTGTAGGCGTCCACCAT-CACGATGTGGGCGC CGCCC (SEQ ID NO:79) were annealed and ligated into pFab5cHis. To generate pFab5cHis SpyTag DA, pFab5cHis was digested with XhoI and NotI. Primers 5'-TCGAGGGCGGCGCCCACATCG TGATGGTGGCCGCCTACAAGCCGACGAAGGGCGC (SEQ ID NO:80) and 5'-GGCCGCCTTCGTCGGCTTGTAGCGGCCACCAT-CACGATGTGGGCGCCGCCC (SEQ ID NO:81) were annealed and ligated into pFab5cHis. The pFab5cHis-DsbA-SpyCatcher-GSSGS-TEV protease cleavage site-gill was constructed in a two-step process. In the first step SpyCatcher followed by the sequence GSSGSENLYFQGSG was cloned in-frame with the PelB leader and gill by amplification. SpyCatcher was amplified from pDEST14 SpyCatcher using 5'-TAATCTCGAGATCAGGGCGC- CATG GTTGATACCTTATC (SEQ ID NO:82) and 5'-ATATGCGGCCGCTCCACTCCCCTG-GAAGTAGAGGTTTTC (SEQ ID NO:83). The insert and vector were digested using XhoI and NotI and then ligated. In the second step, the PelB signal sequence was replaced with DsbA signal sequence by SLIM PCR using 5'-GCGTT-TAGCGCATCGGCGGGCAGCTACCCATAC-GATGTTCCAGATTACGCTG GTGCAGCTGCAGGTCG (SEQ ID NO:84), 5'-CGCC-GATGCGCTAAACGCTAAAACTAAACCAGCCAGCG CCAGCCAAATC TTTTTCATAGCTGTTTCCTGTGT-GAAATTG (SEQ ID NO:85), 5'-GGTGCAGCTGCAGGTCG (SEQ ID NO:86), and 5'-TTTCATA GCTGTTTCCTGTGTGAAATTG (SEQ ID NO:87).

Generation of a Randomised N-Terminal Library of SpyTaq

The library was assembled from one PCR-amplified fragment of the phagemid pFab5cHis-PelB-SpyTag-gIII and one restriction-digested vector by ligation. The insert was amplified by PCR using forward (5'-ACCTCGAGATNNKNNKNNKNNKNNKATCGT-GATGGTGGACGCCTACAAGCC (SEQ ID NO:88)) and reverse (5'-ATTCATATGGTTTACCAGCGCCAAA-GACAAAAGGG (SEQ ID NO:89)) primers flanking the SpyTag gene facing inwards that add XhoI and NdeI restriction sites. DpnI was added to the insert PCR mixture following thermal cycling and incubated at 37° C. for 1 h and heat inactivated at 80° C. for 20 min. Vector DNA was digested with XhoI and NdeI in CutSmart buffer (NEB) at 37° C. for 1.5 h and heat inactivated at 65° C. for 20 min. Total insert and vector reaction mixtures were mixed with 6×DNA loading dye and separated by agarose gel electrophoresis. DNA bands corresponding to the vector and insert were purified by gel extraction. Insert DNA was digested with XhoI and NdeI in CutSmart buffer at 37° C. for 1 h and heat-inactivated at 65° C. for 20 min. Digested insert was cleaned and concentrated using a Thermo Scientific spin column and eluted in MilliQ water. Ligation was performed at the optimized vector:insert molar ratio of 1:7 (1:1 weight) with 627 ng DNA of each fragment in a total volume of 150 μL. DNA and water were heated to 65° C. for 5 min, cooled, T4 DNA ligase (NEB) and buffer were added and the mix was incubated at 25° C. for 1 h. DNA was concentrated on a spin-filter and transformed into electro-competent ER2738 amber stop codon suppressor cells (Lucigen) by electroporation. Transformants were recovered by addition of 950 μL SOC medium at 37° C. for 1 h and plated on LB agar, containing ampicillin at 100 μg/mL and tetracycline at 25 μg/mL. Plates were incubated at 37° C. for 16 h. To harvest the library, 5 mL LB was added to the plate surface and cells were scraped with a plastic spreader, pipetted into a 50 mL Falcon tube and repeated with another 5 mL. After collecting from all plates, the cells were pelleted at 2,500×g for 10 min at 4° C., resuspended in 10 mL LB containing ampicillin (100 μg/mL), tetracycline (25 μg/mL) and 22% (v/v) glycerol. Aliquots were flash-frozen and stored at −80° C.

Generation of a Randomised C-Terminal SpyTaq Library

The library was assembled from two PCR-amplified fragments of the phagemid pFab5cHis-PelB-SpyTag-gIII. In the first PCR, the forward primer (5'-CGACCTCGAGATGTGCCTACTA TCGT-GATGGTGGACNNKNNKNNKNNKGCGGCCGCA GGCTCTAAAGATAT CAGACC (SEQ ID NO:90)) converts the N-terminus of the SpyTag to start VPT instead of AH, in addition to introducing the C-terminal mutations, and a reverse primer priming from the Ampicillin resistance gene (5'-GATCGTTGTCAGAAGTAAGTTGGCC (SEQ ID NO:91)). In the second PCR reaction, the forward primer primed from the ampicillin gene (5'-GGCCAACT-TACTTCTGACAACGATC (SEQ ID NO:92)) and the reverse primer (5'-GTCCACCATCACGATAGTAGGCA-CATCTCGAGGTCGACCTGC (SEQ ID NO:93)) was from the start of the VPT-SpyTag immediately prior to the region being mutated. The two PCR products were digested with DpnI as above, mixed with DNA loading dye and separated by agarose gel electrophoresis. DNA bands were purified by gel extraction and joined by Gibson Assembly. DNA was cleaned, concentrated, and transformed into electro-competent ER2738 cells.

Generation of Libraries of SpyCatcher Variants by Error-Prone PCR

The libraries were assembled from two PCR-amplified fragments from the phagemid pFab5cHis-DsbA-SpyCatcher variant-GSSGS-TEV protease cleavage site-gill by Gibson assembly. The vector was amplified using KOD polymerase with oligonucleotide primers flanking the SpyCatcher gene facing outwards (forward primer: 5'-GGATCCAGTGGTAGCGAAAACC (SEQ ID NO:94); reverse primer: 5'-AACCATGGCGCCCTGATCTCG (SEQ ID NO:95)). The insert was amplified with Taq polymerase under error-prone conditions (0.4 mM $MnCl_2$; unbalanced dNTPs, 0.24 mM dGTP, 0.2 mM dATP/dCTP/dTTP final concentrations) with oligonucleotide primers flanking SpyCatcher and facing inwards (forward primer: 5'-CCTCGAGATCAGGGCGCCATGG (SEQ ID NO:96); reverse primer: 5'-GAAGTAGAGGTTTTCGCTAC-CACTGGATC (SEQ ID NO:97)) for 18-23 cycles, with the number of cycles varied to alter the mutational load on the SpyCatcher. DpnI was added following thermal cycling and incubated at 37° C. for 1 h and heat-inactivated at 80° C. for 20 min. Total reaction mixtures were mixed with 6×DNA loading dye and separated by agarose gel electrophoresis. DNA bands for the vector and insert were purified by gel extraction (Thermo Scientific) and linked by Gibson Assembly (NEB). DNA was cleaned, concentrated, and transformed into electrocompetent XL1 Blue amber stop codon suppressor cells (Agilent Technologies).

Production of Phaqe

Libraries of SpyCatcher in XL1 Blue and SpyTag in ER2738 cells were converted to phage-displayed protein libraries by infection. For the first panning round, a larger phage grow-up was required using 250 mL 2×TY with ampicillin (100 μg/mL), tetracycline (25 μg/mL) with 0.2% (v/v) glycerol also included for production of SpyCatcher phage. This media was inoculated with 100 μL of −80° C. library culture stock for the cells produced from the initial libraries produced as described above. For subsequent panning rounds, 600 μL of −80° C. library culture stock (produced as described below) was used to inoculate 100 mL of the growth medium. For purification of monoclonal phage variants, overnight starter cultures (grown in the growth medium) were used to inoculate (at a 1:100 dilution) 15 mL of growth medium. In all cases, cultures were grown at 37° C. at 200 rpm until an OD600 of 0.5 was reached (~3-4 h) and infected with $10^{12}$ R408 helper phage and incubated with slow mixing (80 rpm) at 37° C. for 30 min. Expression of the SpyCatcher/SpyTag-pIII proteins was induced with IPTG (0.42 mM for SpyTag phage production and 0.1 mM for SpyCatcher phage production) and incubated for 18-20 h at 200 rpm at 25° C. (SpyTag phage) or 18° C. (SpyCatcher phage).

Purification of Phaqe by Precipitation

Infected bacterial cultures were centrifuged at 15,000×g for 10 min at 4° C. to remove the bacterial cells. One volume of precipitation buffer [sterile, 20% (w/v) PEG8000, 2.5M NaCl] was added to 4 volumes of supernatant. The supernatants were mixed and incubated at 4° C. for 3-4 h. Phage were pelleted by centrifugation at 15,000×g for 30 min at 4° C. and the supernatant was removed. Phage pellets were resuspended in PBS pH 7.5 (2 mL per 100 mL culture) and centrifuged at 15,000×g for 10 min at 4° C. to clear any residual cells, before the supernatant was transferred to a new tube. The mixture was precipitated again as previously, but this time resuspended in 0.25 mL PBS per 100 mL culture. Samples were centrifuged at 15,000×g for 10 min at 4° C. to clear any residual cells and phage were precipitated a third time and resuspended in a final volume of 0.25 mL PBS per 100 mL culture. Samples were stored short-term (1-2 weeks) at 4° C., or long-term at −80° C. Typically, a 100 mL culture gave 250 µL of ~$10^{12}$ phage/mL.

Phaqe Quantification

Purified phage were quantified by qPCR of lysed phage (by boiling at 95° C. for 7 min in PBS) using primers specific to the gill gene (5'-GTCTGACCTGCCTCAACCTC (SEQ ID NO:98) and 5'-TCACCGGAACCAGAGCCAC (SEQ ID NO:99)). 5 µL phage lysate was added to 10 µL qPCR master mix (Bioline) in qPCR tubes (Qiagen) to give final concentrations of 1× SensiMix buffer (Bioline) and 0.25 µM of each primer. Standards of known phage concentration at $10^4$ to $10^9$ phage/mL were tested to create a standard curve and a water+buffer master mix sample was included as a negative control. Samples were run in duplicate using: 45 cycles with initial denaturation 95° C., 10 min (first cycle only); denaturation 95° C., 10 s; annealing 60° C., 10 s; extension 72° C., 15 min. Gain; green 10 yellow 5, HRM 7 on a Rotor-Gene Q qPCR machine (Qiagen). Data were analysed using the manufacturer's software using an upper threshold of 0.2 and slope correcting just above the background noise of the curves to give count (Ct) values. The standards were used to produce a plot of phage number versus Ct.

Panning of Library Variants

Biotinylated AP-SpyCatcher (WT/EQ) and AP-SpyTag (WT/DA)-MBP were used as bait to react with the SpyTag and SpyCatcher phage libraries, respectively. The non-reactive bait variants (SpyCatcher EQ and SpyTag-DA-MBP) were included in parallel selections to assess the efficiency of the subsequent washing. Reactions were carried out in PBS pH 7.5 with 3% (w/v) BSA and supplemented with 25 µM Hiss-MBP (for SpyCatcher phage selections to counter-select for SpyCatcher-phage variants that bind to MBP rather than SpyTag) at 25° C. In the first panning round, 1×$10^{12}$ phage were included at a bait concentration (0.5 µM bio-AP-SpyCatcher for SpyTag-phage panning; and 0.5 µM bio-AP-SpyTag-MBP for SpyCatcher-phage panning) into the reaction and reacted for either 5 h (SpyTag-phage) or 18 h (SpyCatcher-phage). Two subsequent rounds (0.2 µM bio-AP-SpyCatcher and 30 min reaction in round 2, and 0.2 µM bio-AP-SpyCatcher and 10 min reaction in round 3) of panning were carried out for SpyTag-phage with the round 3 reaction carried out with the modification of the addition of 10 mM DTT. For SpyCatcher-phage three subsequent selection rounds were carried out (0.2 µM bio-AP-SpyTag and 30 min reaction in round 2, 0.2 µM bio-AP-SpyTag and 10 min reaction in round 3; 0.05 µM bio-AP-SpyTag and 10 min reaction in round 4). In each case, the time of reaction was controlled by the addition of excess (50-100 µM) bait protein without an AP-tag and consequently non-biotinylated (SpyCatcher for the SpyTag-phage panning, and SpyTag-MBP for the SpyCatcher-phage). Phage were purified from unreacted biotinylated bait using PEG/NaCl precipitation, with the supernatant discarded. The pellet containing the phage-biotinylated bait adduct was resuspended in 200-800 µL PBS pH 7.5 0.1% (v/v) Tween20, as appropriate for the selection round (earlier rounds with longer reaction times and higher biotinylated bait concentrations were expected to require a greater number of beads to ensure all variants were bound). 25 µl Biotin-Binder Dynabeads (ThermoFisher Scientific) per well were added to a 96-well low bind Nunc plate that had been pre-blocked for 2 h at 25° C. with 3% (w/v) BSA in PBS pH 7.5+0.1% (v/v) Tween-20. The beads were captured using a 96-well microtitre plate magnetic separation rack (NEB) and washed 4 times with 200 µL/well PBS pH 7.5+0.1% (v/v) Tween-20. For each well in the microtitre plate, beads were resuspended in 200 µL of the PBS pH 7.5 0.1% (v/v) Tween-20 containing the phage-biotinylated bait adduct and incubated with shaking at 800 rpm for 1 h at 25° C. To remove weakly bound phage, beads were washed once with 150 µL glycine-HCl pH 2.2, then four times with 150 µL TBS with 0.5% (v/v) Tween-20. Phage were eluted from beads by TEV protease digestion at 34° C. for 2 h with shaking at 1,000 rpm in 50 mM Tris pH 8.0 with 0.5 mM EDTA using 50 µL 0.72 mg/mL MBP-TEV protease. Eluted phage were rescued by infection of 1 mL of mid-log ($OD_{600}$=0.5) cultures of ER2738 (for SpyTag-phage) or XL-1 Blue (for SpyCatcher-phage) grown in LB supplemented with 25 µg/mL tetracycline with shaking at 37° C. at 80 rpm for 30 min. The cells were then diluted into 100 mL 2×TY (supplemented with 1% (v/v) glucose, 100 µg/mL ampicillin and 25 µg/mL tetracycline) and grown for 12-16 h with shaking at 200 rpm until the cells were in stationary phase. After addition of glycerol to a final concentration of 20% (v/v), cell aliquots were flash frozen and stored at −80° C. The number of phage eluted was quantified by plating serial dilutions.

In Vitro 'On-Phaqe' Kinetic Validation of Improved Variants

Prior to cloning sequenced monoclonal phage variants into bacterial expression vectors, the variants were pre-screened for being able to react better than the equivalent wild-type phage. After expression and purification of the phage (described above), their reactivity with their baits were assayed using an adapted version of the panning protocol after normalisation of the phage concentration for the batch produced (with the wild-type variant included each time) typically to a value of 2×$10^{12}$ phage/mL. The reaction conditions used were PBS pH 7.5+2.5% (w/v) BSA at 25° C. with 200-500 µM biotin-AP-bait (AP-SpyTag-MBP or AP-SpyCatcher). To initiate the reaction, 2 µL phage was added to 6 µL of the reaction buffer in PCR tubes. After the required reaction time (typically 15 min), reactions were quenched with non-biotinylated bait (100 µM final concentration) for 20 min at 25° C. Subsequently, 7 µL phage precipitation buffer was added and incubated for 1 h at 4° C. PCR tubes were centrifuged at 15,000×g for 30 min, supernatant discarded and phage pellet resuspended in 200 µL PBS+0.1% (v/v) Tween20. The phage were then added to Biotin-Bind Dynabeads as described previously for the phage panning with the beads. After washing the beads once with 150 µL/well Glycine-HCl pH 2.2, then four times with 150 µL/well TBS-Tween20 (0.5% v/v), the beads were finally resuspended in 150 µL PBS and 50 µL was removed into a fresh PCR tube, and phage were lysed by boiling at 95° C. for 7 min. Beads were captured with a MagRack 6 magnet (GE) and supernatant was quantified for phage number by qPCR, as above.

Expression and Purification of Variants of SpyCatcher and SpyTag

SpyCatcher variants (including SpyCatcher002-EQ) were expressed in E. coli C41 DE3 (a gift from Anthony Watts (University of Oxford)) and SpyTag-MBP variants (including SpyTag002-DA-MBP) were expressed in E. coli BL21 DE3 RIPL (Stratagene). Single colonies were picked into 10 mL LB containing either ampicillin (pDEST14) or kanamycin (pET28a) and grown overnight. 1 L LB supplemented with 0.8% (w/v) glucose and appropriate antibiotic in high-yield baffled flasks was inoculated with 1/100 dilution of the saturated overnight culture and grown at 37° C. with shaking at 200 rpm. After reaching $OD_{600}$ 0.5-0.6, the cultures were inoculated with 0.42 mM IPTG and incubated at 30° C. with shaking at 200 rpm for 4-5 h. Cells were harvested and lysed in TBS containing mixed protease inhibitors (Complete mini EDTA-free protease inhibitor cocktail; Roche) and 1 mM PMSF by sonication and purified by Ni-NTA (Qiagen). Proteins were dialyzed into PBS with three buffer changes. Expression and purification of AP-SpyCatcher (WT/EQ), AP-SpyTag (WT/DA)-MBP, SpyCatcher-sfGFP, SpyCatcher002-sfGFP, MBPx-SpyCatcher, $His_6$-MBP, MBP-x-SpyCatcher002 were also carried out using the same procedure. $NH_2$-MBP-$His_6$-TEV protease was expressed and purified in a similar manner, with the procedure modified such that the protein was dialysed three times in to 50 mM Tris HCl pH 8.0+0.5 mM EDTA.

Isopeptide Bond Reconstitution Experiments

Isopeptide bond formation was monitored as previously described (Zakeri et al., 2012, supra). Buffers used were: HEPES [50 mM 4-(2-hydroxyethyl)-1-piperazine pH 7.5], HBS (50 mM HEPES+150 mM NaCl pH 7.5), TBS [50 mM tris-hydroxymethyl aminomethane+150 mM NaCl pH 7.5), PBS, PBS+1 mM EDTA (ethylenediamine tetraacetic acid) pH 7.5. Time-points were quenched by addition of 6×SDS-PAGE loading dye (0.23M Tris HCl pH 6.8, 24% (v/v) glycerol, 120 μM bromophenol blue, 0.23M SDS), followed by heating at 95° C. in a Bio-Rad C1000 thermal cycler for 6 min. Reactions were analysed using SDS-PAGE on 16% polyacrylamide gels with staining using InstantBlue (Expedeon) Coomassie and band intensities quantified using a Gel Doc XR imager and Image Lab 5.0 software (Bio-Rad). Percentage isopeptide reconstitution was calculated by dividing the intensity of the band for the covalent complex by the intensity of all the bands in the lane and multiplying by 100. The second-order rate constant for SpyCatcher: SpyTag-MBP covalent complex formation was determined by monitoring the reduction in intensity of the band for the SpyCatcher relative to a control not incubated with SpyTag-MBP, to give the concentration of unreacted SpyCatcher. Time-points were analysed during the linear portion of the reaction progress curve. 1/[SpyCatcher] was plotted against and time and analysed by linear regression using Excel.

When assays were carried out at 0.1 μM (FIG. 9B), SpyCatcher-sfGFP and SpyCatcher002-sfGFP was used. The reaction was quenched at the lower temperature of 50° C. after addition of SDS-loading buffer to retain the fluorescence of sfGFP. Reactions were run on 16% SDS-PAGE and the unreacted SpyCatcher-sfGFP and SpyTag-MBP:SpyCatcher-sfGFP covalent product bands were quantified using a Fluorescent Image Analyzer FLA-3000 (FujiFilm) and ImageGauge version 4.21 software.

Temperature-dependence of the reaction was measured in PBS pH 7.5 (since its pH has only a small variation with temperature) with 0.5 μM for each protein. For pH-dependence, each protein was mixed at 0.5 μM and 25° C. in succinate-phosphate-glycine buffer (12.5 mM succinic acid, 43.75 mM $NaH_2PO_4$, 43.75 mM glycine; pH was adjusted using HCl or NaOH), enabling suitable buffering over a broad pH range.

Buffer-dependence was measured in PBS (±EDTA), HBS, HEPES, or TBS at pH 7.5 with 0.5 μM for each protein at 25° C. Detergent-dependence was measured with 0.5 μM for each protein at 25° C. in PBS pH 7.5 supplemented with 1% (v/v) Tween 20 or 1% (v/v) Triton X-100.

Assays to test if SpyCatcher002 and SpyTag002 react to completion were carried out in succinate-phosphate-glycine buffer at pH 7.0 for 1 h at 25° C. To test if SpyCatcher002 reacts to completion, 10 μM SpyCatcher002 was reacted with 20 μM SpyTag002-MBP. To test if SpyTag002-MBP reacts to completion, 10 μM SpyTag002-MBP was reacted with 20 μM SpyCatcher002.

Assays to test SpyCatcher002 reaction with SpyTag002-MBP in increasing concentrations of urea were carried out in PBS including the required concentration of urea (from 0-8M), which was subsequently adjusted to pH 7.5 using HCl. All reactions were carried out using freshly prepared urea-containing buffer solutions at 2 μM of each protein in triplicate at 25° C. The extent of reaction was analyzed after 30 min and 120 min.

SpyCatcher002-EQ and SpyTag002-DA-MBP mutants were constructed by QuikChange site-directed mutagenesis. Assays were carried out with each protein at 10 μM in succinate-phosphate-glycine buffer at pH 7.0 for 1 h at 25° C.

Quantification of Protein Concentration

Protein concentrations were determined by absorbance at 280 nm using the extinction coefficients calculated by ProtParam.

Mass Spectrometry.

95 μM SpyCatcher002 was reacted with 220 μM peptide containing SpyTag002 (KGVPTIVMVDAYKRYK (SEQ ID NO:100), solid-phase synthesized by Insight Biotechnology at >95% purity) for 3 h at 25° C. in PBS pH 7.5. The reaction was dialysed against 10 mM ammonium acetate pH 7.5 using 3.5 kDa cut-off Spectra/Por dialysis tubing (Spectrum labs) three times each for 3 h at 4° C. Mass spectrometry was performed using a Waters LCT Premier XE (Waters Corporation) equipped with electrospray interface after the sample had been passed through a Merck Chromolith C18 2×5 mm guard column. The software used to analyse the data and convert the m/z spectrum to a molecular mass profile was MassLynx 4.1 (with OpenLynx open access) (Waters Corporation). The predicted molecular mass of the covalent complex was calculated using ExPASy ProtParam, taking into account the cleavage of N-terminal fMet and subtracting 18 Da for isopeptide bond formation.

Sequence Alignments

Multiple sequence alignments were generated using Clustal Omega.

The invention claimed is:

1. A nucleic acid molecule comprising a nucleotide sequence which encodes a peptide capable of spontaneously forming an isopeptide bond with a polypeptide comprising an amino acid sequence as set forth in SEQ ID NO: 2, said peptide comprising an amino acid sequence as set forth in SEQ ID NO: 1, wherein:
   (i) X at position 1 is arginine or no amino acid;
   (ii) X at position 2 is glycine or no amino acid;
   (iii) X at position 5 is histidine or threonine;
   (iv) X at position 11 is alanine, glycine or valine; and
   (v) X at position 14 is arginine or lysine, wherein when X at position 1 is no amino acid, X at position 2 is no amino acid;
   and wherein said isopeptide bond forms between the aspartic acid residue at position 10 of SEQ ID NO: 1 and the lysine residue at position 34 of SEQ ID NO: 2.

2. The nucleic acid molecule of claim 1, wherein the encoded peptide comprises one or more of the following:
   1) histidine at position 5;
   2) alanine at position 11; or
   3) arginine at position 14.

3. The nucleic acid molecule of claim 1, wherein the encoded peptide comprises an amino acid sequence as set forth in any one of SEQ ID NOs: 3-5.

4. The nucleic acid molecule of claim 1, wherein the nucleic acid molecule comprises:
(i) a nucleotide sequence as set forth in any one of SEQ ID NOs: 11-13; or
(ii) a nucleotide sequence with at least 80% sequence identity to a nucleotide sequence as set forth in any one of SEQ ID NOs: 11-13.

5. The nucleic acid molecule of claim 1, wherein the nucleic acid molecule encodes a recombinant polypeptide comprising: (i) a polypeptide; and (ii) said peptide.

6. A vector comprising the nucleic acid molecule of claim 1.

7. A vector comprising the nucleic acid molecule of claim 5.

8. A cell comprising:
(i) a nucleic acid molecule of claim 1;
(ii) a nucleic acid molecule of claim 1, wherein the nucleic acid molecule encodes a recombinant polypeptide comprising: (i) a polypeptide; and (ii) said peptide as defined in claim 1;
(iii) a vector comprising a nucleic acid molecule of claim 1; or
(iv) a vector comprising a nucleic acid molecule of claim 1, wherein the nucleic acid molecule encodes a recombinant polypeptide comprising: (i) a polypeptide; and (ii) said peptide as defined in claim 1.

9. A process for producing or expressing a recombinant polypeptide capable of being encoded by a nucleic acid molecule of claim 1, wherein the recombinant polypeptide comprises (i) a polypeptide; and (ii) said peptide as defined in claim 1, the process comprising the steps of:
a) transforming or transfecting a host cell with a vector comprising a nucleic acid molecule of claim 1, wherein the nucleic acid molecule encodes a recombinant polypeptide comprising: (i) a polypeptide; and (ii) said peptide as defined in claim 1;
b) culturing the host cell under conditions which allow the expression of the recombinant polypeptide; and optionally
c) isolating the recombinant polypeptide.

10. A nucleic acid molecule comprising a nucleotide sequence which encodes a polypeptide comprising:
i) an amino acid sequence as set forth in SEQ ID NO: 2; or
ii) a portion of (i) comprising an amino acid sequence as set forth in SEQ ID NO: 101; or
iii) an amino acid sequence with at least 80% sequence identity to a sequence as set forth in SEQ ID NO: 2, wherein said amino acid sequence comprises a lysine at position 34, a glutamic acid at position 80 and two or more of the following:
1) threonine at position 5;
2) proline at position 16;
3) arginine at position 40;
4) histidine at position 65;
5) proline at position 92;
6) aspartic acid at position 100:
7) glutamic acid at position 108; or
8) threonine at position 116,
wherein the specified amino acid residues are at positions equivalent to the positions in SEQ ID NO: 2; or
iv) a portion of (iii) comprising an amino acid sequence with at least 80% sequence identity to a sequence as set forth in SEQ ID NO: 101, wherein the amino acid sequence comprises a lysine at position 10, a glutamic acid at position 56 and one or more of the following:
1) arginine at position 16;
2) histidine at position 41;
3) proline at position 68; or
4) aspartic acid at position 76,
wherein the specified amino acid residues are at positions equivalent to the positions in SEQ ID NO: 101,
and wherein said polypeptide is capable of spontaneously forming an isopeptide bond with a peptide comprising an amino acid sequence as set forth in SEQ ID NO: 5, wherein said isopeptide bond forms between the aspartic acid residue at position 10 of SEQ ID NO: 5 and the lysine residue at position 34 of SEQ ID NO: 2 or position 10 of SEQ ID NO: 101.

11. The nucleic acid molecule of claim 10, wherein the encoded polypeptide comprises an amino acid sequence with at least 80% sequence identity to a sequence as set forth in SEQ ID NO: 2, wherein said amino acid sequence comprises a lysine at position 34, a glutamic acid at position 80 and all of the following:
1) threonine at position 5;
2) proline at position 16;
3) arginine at position 40;
4) histidine at position 65;
5) proline at position 92;
6) glutamic acid at position 108; and
7) threonine at position 116,
wherein the specified amino acid residues are at positions equivalent to the positions in SEQ ID NO: 2.

12. The nucleic acid molecule of claim 10, wherein the encoded polypeptide comprises an amino acid sequence with at least 80% sequence identity to a sequence as set forth in SEQ ID NO: 2, wherein said amino acid sequence comprises a lysine at position 34, a glutamic acid at position 80 and all of the following:
1) threonine at position 5;
2) proline at position 16;
3) arginine at position 40;
4) histidine at position 65;
5) proline at position 92;
6) aspartic acid at position 100:
7) glutamic acid at position 108; and
8) threonine at position 116,
wherein the specified amino acid residues are at positions equivalent to the positions in SEQ ID NO: 2.

13. The nucleic acid molecule of claim 10, wherein the encoded polypeptide comprises one or more of the following:
1) glycine at position 12; and
2) threonine at position 22,
wherein the specified amino acid residues are at positions equivalent to the positions in SEQ ID NO: 2.

14. The nucleic acid molecule of claim 10, wherein the encoded polypeptide comprises an amino acid sequence as set forth in SEQ ID NO: 2 or SEQ ID NO: 101.

15. The nucleic acid molecule of claim 10, wherein the nucleic acid molecule comprises:
(i) a nucleotide sequence as set forth in SEQ ID NO: 14; or
(ii) a nucleotide sequence with at least 80% sequence identity to a nucleotide sequence as set forth in SEQ ID NO: 14.

16. The nucleic acid molecule of claim 10, wherein the nucleic acid molecule encodes a recombinant polypeptide comprising: (i) a polypeptide; and (ii) said polypeptide as defined in claim 10.

17. A vector comprising the nucleic acid molecule of claim 10.

18. A vector comprising the nucleic acid molecule of claim 16.

19. A cell comprising:
(i) a nucleic acid molecule of claim 10;
(ii) a nucleic acid molecule of claim 10, wherein the nucleic acid molecule encodes a recombinant polypeptide comprising: (i) a polypeptide; and (ii) said polypeptide as defined in claim 10;
(iii) a vector comprising a nucleic acid molecule of claim 10; or
(iv) a vector comprising a nucleic acid molecule of claim 10, wherein the nucleic acid molecule encodes a recombinant polypeptide comprising: (i) a polypeptide; and (ii) said polypeptide as defined in claim 10.

20. A process for producing or expressing a recombinant polypeptide as defined in claim 16 comprising the steps of:
a) transforming or transfecting a host cell with a vector comprising a nucleic acid molecule of claim 10, wherein the nucleic acid molecule encodes a recombinant polypeptide comprising: (i) a polypeptide; and (ii) said polypeptide as defined in claim 10;
b) culturing the host cell under conditions which allow the expression of the recombinant polypeptide; and optionally
c) isolating the recombinant polypeptide.

* * * * *